US009605008B2

(12) United States Patent
Vakalopoulos et al.

(10) Patent No.: US 9,605,008 B2
(45) Date of Patent: Mar. 28, 2017

(54) BENZYL-1H-PYRAZOLO[3,4-B]PYRIDINES AND USE THEREOF

(71) Applicant: BAYER PHARMA AKTIENGESELLSCHAFT, Berlin (DE)

(72) Inventors: Alexandros Vakalopoulos, Hilden (DE); Alexey Gromov, Erkrath (DE); Markus Follmann, Köln (DE); Damian Brockschnieder, Haan (DE); Johannes-Peter Stasch, München (DE); Tobias Marquardt, Wuppertal (DE); Adrian Tersteegen, Wuppertal (DE); Frank Wunder, Wuppertal (DE); Gorden Redlich, Bochum (DE); Dieter Lang, Velbert (DE); Volkhart Min-Jian Li, Velbert (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 14/903,347

(22) PCT Filed: Jul. 8, 2014

(86) PCT No.: PCT/EP2014/064547
§ 371 (c)(1),
(2) Date: Jan. 7, 2016

(87) PCT Pub. No.: WO2015/004105
PCT Pub. Date: Jan. 15, 2015

(65) Prior Publication Data
US 2016/0145271 A1    May 26, 2016

(30) Foreign Application Priority Data

| Jul. 10, 2013 | (EP) | 13175889 |
| Jul. 10, 2013 | (EP) | 13175890 |
| Jul. 10, 2013 | (EP) | 13175892 |
| Jul. 10, 2013 | (EP) | 13175894 |
| Jul. 10, 2013 | (EP) | 13175895 |
| Jul. 10, 2013 | (EP) | 13175896 |
| Jul. 10, 2013 | (EP) | 13175898 |
| Jul. 10, 2013 | (EP) | 13175899 |
| Jul. 10, 2013 | (EP) | 13175903 |
| Jul. 10, 2013 | (EP) | 13175904 |

(51) Int. Cl.
| A61K 31/53 | (2006.01) |
| C07D 519/00 | (2006.01) |
| C07D 519/04 | (2006.01) |
| A61K 45/06 | (2006.01) |

(52) U.S. Cl.
CPC .......... *C07D 519/00* (2013.01); *A61K 31/53* (2013.01); *A61K 45/06* (2013.01); *C07D 519/04* (2013.01)

(58) Field of Classification Search
CPC .............................. A61K 31/53; C07D 519/00
See application file for complete search history.

(56) References Cited

U.S. PATENT DOCUMENTS

| 4,833,246 | A | 5/1989 | Adachi et al. |
| 5,976,523 | A | 11/1999 | Awaya et al. |
| 6,166,027 | A | 12/2000 | Straub et al. |
| 6,180,656 | B1 | 1/2001 | Furstner et al. |
| 6,451,805 | B1 | 9/2002 | Straub et al. |
| 6,743,798 | B1 | 6/2004 | Straub et al. |
| 6,833,364 | B1 | 12/2004 | Straub et al. |
| 6,903,089 | B1 | 6/2005 | Stasch et al. |
| 7,173,037 | B2 | 2/2007 | Alonso-Alija et al. |
| 7,323,472 | B2 | 1/2008 | Adams et al. |
| 7,410,973 | B2 | 8/2008 | Feurer et al. |
| 7,414,136 | B2 | 8/2008 | Matsumura et al. |
| 7,528,132 | B2 | 5/2009 | Chan et al. |
| 7,541,367 | B2 | 6/2009 | Chiu et al. |
| 8,058,282 | B2 | 11/2011 | Adams et al. |
| 8,242,272 | B2 | 8/2012 | Jimenez et al. |
| 8,293,900 | B2 | 10/2012 | Jian et al. |
| 8,309,551 | B2 | 11/2012 | Schirok et al. |
| 8,420,656 | B2 | 4/2013 | Follmann et al. |
| 8,741,910 | B2 | 6/2014 | Brockunier et al. |
| 8,765,769 | B2 | 7/2014 | Follmann et al. |
| 8,859,569 | B2 | 10/2014 | Follmann et al. |
| 9,023,849 | B2 | 5/2015 | Follmann et al. |

(Continued)

FOREIGN PATENT DOCUMENTS

| CA | 2 804 470 A1 | 1/2012 |
| CA | 2 809 911 A1 | 3/2012 |

(Continued)

OTHER PUBLICATIONS

F. Wunder et al., 339 Analytical Biochemistry, 104-112 (2005).*
T.L. Poulos et al., Current Opinion in Structural Biology (2006).*
A.J. Hobbs, 136 British Journal of Pharmacology (2002).*
R. Dumitrascu et al., 113 Circulation, 286-295 (2006).*
International Search Report (PCT/ISA/210) issued on Oct. 2, 2014, by the European Patent Office as the International Searching Authority for International Application No. PCT/EP2014/064547.
Written Opinion (PCT/ISA/237) issued on Oct. 2, 2014, by the European Patent Office as the International Searching Authority for International Application No. PCT/EP2014/064547.

(Continued)

*Primary Examiner* — Alexander R Pagano
(74) *Attorney, Agent, or Firm* — Buchanan Ingersoll & Rooney PC

(57) ABSTRACT

The present application relates to novel benzyl-1H-pyrazolo[3,4-b]pyridines, to processes for their preparation, to their use alone or in combinations for the treatment and/or prophylaxis of diseases, and to their use for producing medicaments for the treatment and/or prophylaxis of diseases, in particular for the treatment and/or prophylaxis of cardiovascular disorders.

24 Claims, No Drawings

(56) References Cited

U.S. PATENT DOCUMENTS

| | | | |
|---|---|---|---|
| 9,040,538 B2 | 5/2015 | Attardo et al. | |
| 9,090,609 B2 | 7/2015 | Follmann et al. | |
| 9,090,610 B2* | 7/2015 | Follmann | A61K 45/06 |
| 9,096,592 B2 | 8/2015 | Follmann et al. | |
| 9,133,191 B2 | 9/2015 | Follmann et al. | |
| 9,216,978 B2* | 12/2015 | Follmann | A61K 45/06 |
| 9,266,885 B2 | 2/2016 | Follmann et al. | |
| 2004/0235863 A1 | 11/2004 | Feurer et al. | |
| 2012/0029002 A1 | 2/2012 | Straub et al. | |
| 2012/0053146 A1 | 3/2012 | Parker et al. | |
| 2013/0072492 A1 | 3/2013 | Raghavan et al. | |
| 2013/0158028 A1 | 6/2013 | Stasch et al. | |
| 2013/0178475 A1 | 7/2013 | Moore et al. | |
| 2013/0211090 A1 | 8/2013 | Follmann et al. | |
| 2014/0100229 A1* | 4/2014 | Follmann | A61K 45/06 514/243 |
| 2014/0171434 A1 | 6/2014 | Follmann et al. | |
| 2014/0228366 A1* | 8/2014 | Follmann | C07D 519/00 514/243 |
| 2014/0249168 A1 | 9/2014 | Follmann et al. | |
| 2014/0350020 A1* | 11/2014 | Follmann | A61K 45/06 514/243 |
| 2014/0357637 A1* | 12/2014 | Follmann | C07D 519/00 514/243 |
| 2015/0025090 A1 | 1/2015 | Follmann et al. | |
| 2015/0274754 A1* | 10/2015 | Follmann | C07D 519/00 514/243 |
| 2016/0002267 A1 | 1/2016 | Follmann et al. | |
| 2016/0176880 A1 | 6/2016 | Vakalopoulos et al. | |

FOREIGN PATENT DOCUMENTS

| | | |
|---|---|---|
| CA | 2 834 901 A1 | 11/2012 |
| CA | 2 840 886 A1 | 1/2013 |
| CN | 1613849 A | 5/2005 |
| EP | 0634413 A1 | 1/1995 |
| ES | 8601208 A1 | 2/1986 |
| WO | 89/03833 A1 | 5/1989 |
| WO | 96/34866 A1 | 11/1996 |
| WO | WO 00/06568 A1 | 2/2000 |
| WO | WO 00/06569 A1 | 2/2000 |
| WO | WO 01/83490 A1 | 11/2001 |
| WO | WO 03/095451 A1 | 11/2003 |
| WO | WO 2004/009590 A1 | 1/2004 |
| WO | WO 2007/041052 A2 | 4/2007 |
| WO | WO 2009/145814 A2 | 12/2009 |
| WO | WO 2010/065275 A1 | 6/2010 |
| WO | 2011/161099 A1 | 12/2011 |
| WO | WO 2011/149921 A1 | 12/2011 |
| WO | WO 2012/004258 A1 | 1/2012 |
| WO | WO 2012/004259 A1 | 1/2012 |
| WO | WO 2012/028647 A1 | 3/2012 |
| WO | WO 2012/143510 A1 | 10/2012 |
| WO | WO 2012/152629 A1 | 11/2012 |
| WO | 2012/165399 A1 | 12/2012 |
| WO | WO 2013/030138 A1 | 3/2013 |
| WO | 2013/104597 A1 | 7/2013 |
| WO | WO 2013/104703 A1 | 8/2013 |

OTHER PUBLICATIONS

International Search Report (PCT/ISA/210/210) mailed on Apr. 28, 2014, by the European Patent Office as the International Searching Authority for International Application No. PCT/EP2014/053585.
Written Opinion (PCT/ISA/237) mailed on Apr. 28, 2014, by the European Patent Office as the International Searching Authority for International Application No. PCT/EP2014/053585.
Badesch et al., "Prostanoid Therapy for Pulmonary Arterial Hypertension," Journal of the American College of Cardiology, Jun. 16, 2004, 43:56S-61S.
Banholzer et al.,"Zum Mechanisums der thermischen Decarbonylierung von Oxalessigestern," Helv. Chim. Acta., 1959, 42: 2584-2597.
Becker et al.,"NO-Independent Regulatory Site of Direct sGC Stimulators like YC-1 and BAY 41/2272," BMC Pharmacology, 2001, 1(13):1-12.
Cheng et al.,"Potential Purine Antagonists VII. Synthesis of 6-Alkylpyrazolo-[3,4-d]pyrimidines," J. Org. Chem., 1958, 23:191-200.
Daley et al., The First Complete Identification of a Diastereomeric Catalyst-Substrate (Alkoxide) Species in an Enantioselective Ketone Hydrogenation. Mechanistic Investigations J. Am. Chem. Soc. 2002, 124(14):3680-3691.
Dermer, G. B., "Another Anniversary for the War on Cancer," Bio/Technology, 1994, 12:320.
Dumitrascu et al., "Activation of Soluble Guanylate Cyclase Reverses Experimental Pulmonary Hypertension and Vascular Remodeling," 113(2) Circulation 286, 286-95 (Jan. 2006).
Evgenov et al.,"NO-independent stimulators and activators of soluble guanylate cyclase: discovery and therapeutic potential," Nat. Rev. Drug. Disc, Sep. 2006, 5:755-768.
Freshney, R. Ian., "Culture of animal cells," A Manual of Basic Technique, Alan R. Liss, Inc., 1983, New York, p. 4.
Glass et al., "Stimulation of Human Platelet Guanylate Cyclase by Fatty Acids," J. Biol. Chem., Feb. 25, 1977, 252(4):1279-1285.
Greene et al.,"The Role of Protective Groups in Organic Synthesis," Greene's Protective Groups in Organic Synthesis, 2007, Fourth Edition, 1-15.
Ghofrani et al., "Soluble guanylate cyclase stimulation: an emerging option in pulmonary hypertension therapy," Eur. Respir. Rev., 2009, 18(111):35-41.
Grassetti et al., "Syntheis of some homologs of fluoropyruvic acid and their effect on the carbohydrate metabolism of Elrich Ascites Tumor and on Lactate Dehydrogenase," J. Med. Chem. Jan. 1966, 9:149-151.
Hackam, et al. "Translation of Research Evidence from Animals to Humans," JAMA, 296(14), 2006, 1731-1732.
Hassan et al.,"Aryl-Aryl Bond Formation One Century after the Discovery of the Ullmann Reaction," Chem. Rev. 2002, 102: 1359-1469.
Herdemann et al.,"Identification of potent ITK inhibitors through focused compound library design including structural Information," Bioorganic & Medicinal Chemistry Letters, 2010, 20: 6998-7003.
Hobbs, "Soluble guanylate cyclase: an old therapeutic target revisited," 136 British J. Pharmacology 637, 637-40 (2002).
Hughes,"Progress in the Mitsunobu Reaction. A Review," Org. Prep. Procedures Int., 1996, 28(2):127-164.
Jordan, Tamoxifen: "A Most Unlikely Pioneering Medicine," Nature Reviews: Drug Discovery, 2, 2003, 205.
Ko et al., "YC-1, a Novel Activator of Platelet Guanylate Cyclase," Blood, Dec. 1994, 84(12): 4226-4233.
Kozo, O., International Review of Experimental Pathology, University of Bristol Medical School, Bristol, England, "Spontaneous Hypertension in Rats," 1969, 7:227-270.
Kelley et al., "Synthesis and Anticonvulsant Activity of N-Benzylpyrrolo[2,3-d]-, -pyrazolo[3,4-d]-, and -triazolo[4,5-d]pyrimidines: Imidazole Ring-Modified Analogues of 9-(2-Fluorobenzyl)-6-(methylamino)-9H-purine," J. Med. Chem, 1995, 38:3884-3888.
Maarten van den Buuse,"Circadian Rythyms of Blood Pressure, Heart Rate, and Locomotor Activity in Spontaneously Hypertensive Rats as Measured with Radio-Telemetry," Physiology & Behavior, 1994, 55(4):783-787.
T.A. Michel, "Treatment of Myocardial Ischemia," in Goodman & Gilman's: The Pharmacological Basis of Therapeutics, 823-844 (L.L. Brunton et al., eds. 11th ed., 2006).
Mittendorf et al., "Discovery of Riociguat (BAY 63/2521): A Potent, Oral Stimulator of Soluble Guanylate Cyclase for the Treatment of Pulmonary Hypertension," Chem. Med. Chem., 2009, 4: 853-865.
Mülsch et al., "Effect of YC-1, an NO-independent, superoxide-sensitive stimulator of soluble guanylyl cyclase, on smooth muscle responsiveness to nitrovasodilators," Brit. J. Pharm., 1997, 120:681-689.
Olah et al., "Synthesis and Investigation of Organic Fluorine Compounds. XXIII. Preparation of Aromatic Fluorinated Esters as Local Anesthetics," J. Organic Chem. 1957, vol. 22, pp. 879-881.

(56) References Cited

OTHER PUBLICATIONS

Oudot et al., "Combination of BAY 60-4552 and Vardenafil Exerts Proerectile Facilitator Effects in Rats With Cavernous Nerve Injury: A Proof of Concept Study for the Treatment of Phosphodiesterase Type 5 Inhibitor Failure," European Urology, 2011, 60:1020-1026.
Palacios et al. "A New and Efficient Synthesis of Imidazo[1,5-a]pyridine Derivatives by a Tandem Aza-Wittig/Electrocyclic Ring Closure of N-vinylic phosphazenes," Tetrahedron, 1995, 51(12): 3683-3690.
Pettibone et al., "A Structurally Novel Stimulator of Guanylate Cyclase with Long-Lasting Hypotensive Activity in the Dog," Euro. J. of Pharmacology, 1985, 116: 307-312.
Poulos, "Soluble Guanylate Cyclase," Current Opinion in Structural Biology, 736-743 (2006).
Reichardt et al., "Darstellung von Fluor- und Jodmalondialdehyd," Justus Liebigs Annalen der Chemie, 1970, 737:99-107.
Robins, Roland K., "Potential Purine Antagonists. I. Synthesis of Some 4,6-Substituted Pyrazolo [3,4-d] pyrimidines," J. Am. Chem. Soc., 1956, 78: 784-790.
Rocaboy et al.,"Syntheses and Reactivities of Disubstituted and Trisubstituted Fluorous Pyridines with High Fluorous Phase Affinities: Solid State, Liquid Ctystal, and Ionic Liquid-Phase Properties," J. Org. Chem, 2002, 67(20): 6836-6870.
Saenz de Tejada et al., Int J of Impotence Res 2001, 13:282-290.
Sard et al., "Preparation of 4,5-Disubstituted Pyrimidines: Ring Substitution of 5-Mesyloxymethylpyrimidines," J. Org. Chem. 2000, 65:9261-9264.
Sharkovska et al.,"Nitric oxide-independent stimulation of soluble guanylate cyclase reduces organ damage in experimental low-renin and high-renin models," J. Hypertnesion, 2010, 28(8):1666-1675.
Stasch et al.,"Soluble Guanylate Cyclase as an Emerging Therapeutic Target in Cardiopulmonary Disease," Circulation, May 2011, 123: 2263-2273.
Straub et al., "NO-Independent Stimulators of Soluble Guanylate Cyclase," Bioorg. Med. Chem. Lett., 2001, 11:781-784.
Toche et al., "Synthesis of Pyrazolopyridine 3-Carboxylates by Friedlander Condensation," J. Heterocyclic Chem., 2010, 47:287.
Tyutin et al., "Synthesis of Esters of 3,3-Dicyano-2-(Trifluoromethyl) Acrylic Acid and Their Reactions With Arylamines" Journal of Fluorine Chemistry, 1991, 51:323-334.
Wilson et al.,"Development of a Scaleable Synthesis of a Partial Nicotinic Acid Receptor Agonist," Organic Process Research & Development, 2009, 13: 543-547.
Winn et al., "2-(Alkylamino)nicotinic Acid and Analogs. Potent Angiotensin II Antagonists," J. Med. Chem 1993, 36: 2676-2688.
Witte et al.,"Experimental heart failure in rats: effects on cardiovascular circadian rhythms and on myocardial β-adrenergic signaling," Cardiovascular Research, 2000, 47: 350-358.
Wu et al., "YC-1 inhibited human platelet aggregation through NO-independent activation of soluble guanylate cyclase," Br J. Pharmacol. Oct. 1995, 116(3):1973-1978.
Wunder et al., "A cell-based cGMP assay useful for ultra-high-throughput screening and identification of modulators of the nitric oxide/cGMP pathway," Anal. Biochem., 2005, 339:104-112.
Wunder et al., "Characterization of the First Potent and Selective PDE9 Inhibitor Using a cGMP Reporter Cell Line," Molecular Pharmacology 2005, vol. 68, No. 6, 1775-1781.
Yu et al., "Vasorelaxant Effect of Isoliquiritigenin, A novel soluble guanylate cyclase activator, in rat aorta," Brit. J. of Pharmacology, 1995, 114: 1587-1594.
Albersen et al., "Synergistic Effects of BAY 60/4552 and Vardenafil on Relaxation of Corpus Cavernosum Tissue of Patients with Erectile Dysfunction and Clinical Phosphodiesterase Type 5 Inhibitor Failure," The Journal of Sexual Medicine, (May 2013), vol. 10, Issue 5, pp. 1268-1277.
Deng et al., "Studies on Phosphoroheterocycle Chemistry II: A Simple and New Route to 1,3,2-Diazaphospholidine-4-thione 2-sulfide Derivatives," Synthesis, (2001)), No. 16, pp. 2445-2449.
Healthgrades Editorial Staff, "Ischemia—Causes" Ischemia—Symptoms, Causes, Treatments—Causes, (2013), http://www.healthgrades.com/conditions/ischemia-Causes, 2 pages.
Hjørringgaard et al., "An Automatic Solid-Phase Synthesis of Peptaibols," The Journal of Organic Chemistry, (2009), vol. 74, No. 3, pp, 1329-1332.
Hoenicka et al., "Purified Soluble Guanylyl Cyclase Expressed in a Baculovirus/Sf9 System: Stimulation by YC-1, Nitric Oxide, and Carbon Monoxide," Journal of Molecular Medicine, (Jan. 1999), vol. 77, No. 1, pp. 14-23.
Mayo Clinic, "Diseases and Conditions Heart Failure," http://www.mayoclinic.org/diseases-conditions/heart-failure/basics/prevention/con-20029801, Heart Failure Prevention—Mayo Clinic, (2015), 3 pages.
Mayo Clinic, "Diseases and Conditions Pulmonary Fibrosis," http://www.mayoclinic.org/diseases-conditions/pulmonary-fibrosis/basics/treatment/con-20029091, Pulmonary Fibrosis Treatments and Drugs—Mayo Clinic, (2016), 3 pages.
NIH, Prevention of High Blood Pressure, (2015), http://www.nhlbi.nih.gov/health/health-topics/topics/hbp/prevention, 1 page.
Nossaman et al., "Nitrates and Nitrites in the Treatment of Ischemic Cardiac Disease," Cardiol Rev., (Jul.-Aug. 2010), vol. 18, No. 4, pp. 190-197.
Ogrel et al., "Synthesis of 15N-Labelled D-Isovaline and α-Aminoisobutyric Acid," European Journal of Organic Chemistry, (Mar. 2000), vol. 2000, Issue 5, pp. 857-859.
PubMed Health, Angina (2014) http://www.ncbi.nlm.hih.gov/pubmedhealth/PMH0062934_nhlbisec-prevention, 11 pages.
Stasch et al., "Cardiovascular Actions of a Novel NO-Independent Guanylyl Cyclase Stimulator, BAY 41/8543: in vivo Studies," British Journal of Pharmacology, (2002), vol. 135, No. 2, pp. 344-355.
Stasch et al., "Pharmacological Actions of a Novel NO-Independent Guanylyl Cyclase Stimulator, BAY 41/8543: in vitro Studies," British Journal of Pharmaclolgy, (2002), vol. 135, No. 2, pp. 333-343.
WebMD, "How to Prevent Deep Vein Thrombosis (DVT)," (2016), http://www.webmd.com/dvt/deep-vein-thrombosis-prevent-dvt, 2 pages.
WebMD, Heart Disease Health Center the Heart and Vascular Disease, (2016), http://www.webmd.com/heart-disease/vascular-disease, Types of Vascular Disease, 6 pages.
WebMD, "Understanding Kidney Disease-Prevention," (2015), http://www.webmd.com/a-to-z-guides/understanding-kidney-disease-prevention, 2 pages.
Wermuth, "Molecular Variations Based on Isosteric Replacements," The Practice of Medical Chemistry, (1996), pp. 203-237.
Wu et al., "YC-1, a Novel Activator of Platelet Guanylate Cyclase", Blood, 1994, p. 4226-4233. vol. 84, No. 12.

* cited by examiner

BENZYL-1H-PYRAZOLO[3,4-B]PYRIDINES AND USE THEREOF

This application is a national stage entry under 35 U.S.C. §371 for International Application No. PCT/EP2014/064547, filed Jul. 8, 2014, which claims priority to European Patent Application Nos. 13175889.8, 13175904.5, 13175903.7, 13175899.7, 13175898.9, 13175896.3, 13175895.5, 13175894.8, 13175892.2, and 13175890.6, all filed Jul. 10, 2013, the contents of which are incorporated herein by reference for all purposes.

The present application relates to novel benzyl-1H-pyrazolo[3,4-b]pyridines, to processes for their preparation, to their use alone or in combinations for the treatment and/or prophylaxis of diseases, and to their use for producing medicaments for the treatment and/or prophylaxis of diseases, in particular for the treatment and/or prophylaxis of cardiovascular disorders.

One of the most important cellular transmission systems in mammalian cells is cyclic guanosine monophosphate (cGMP). Together with nitrogen monoxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family known to date can be divided into two groups either according to structural features or according to the type of ligands: the particulate guanylate cyclases which can be stimulated by natriuretic peptides, and the soluble guanylate cyclases which can be stimulated by NO. The soluble guanylate cyclases consist of two subunits and very probably contain one haem per heterodimer, which is part of the regulatory centre. This is of central importance for the activation mechanism. NO can bind to the iron atom of haem and thus markedly increase the activity of the enzyme. Haem-free preparations cannot, by contrast, be stimulated by NO. Carbon monoxide (CO) is also able to bind to the central iron atom of haem, but the stimulation by CO is much less than that by NO.

By forming cGMP, and owing to the resulting regulation of phosphodiesterases, ion channels and protein kinases, guanylate cyclase plays an important role in various physiological processes, in particular in the relaxation and proliferation of smooth muscle cells, in platelet aggregation and platelet adhesion and in neuronal signal transmission, and also in disorders which are based on a disruption of the aforementioned processes. Under pathophysiological conditions, the NO/cGMP system can be suppressed, which can lead, for example, to hypertension, platelet activation, increased cell proliferation, endothelial dysfunction, arteriosclerosis, angina pectoris, heart failure, myocardial infarction, thromboses, stroke and sexual dysfunction.

Owing to the expected high efficiency and low level of side effects, a possible NO-independent treatment for such disorders by targeting the influence of the cGMP signal pathway in organisms is a promising approach.

Hitherto, for the therapeutic stimulation of the soluble guanylate cyclase, use has exclusively been made of compounds such as organic nitrates whose effect is based on NO. The latter is formed by bioconversion and activates soluble guanylate cyclase by attack at the central iron atom of haem.

In addition to the side effects, the development of tolerance is one of the crucial disadvantages of this mode of treatment.

Some years ago, a number of substances have been described which stimulate soluble guanylate cyclase directly, i.e. without prior release of NO, such as, for example, 3-(5'-hydroxymethyl-2'-furyl)-1-benzylindazole [YC-1; Wu et al., Blood 84 (1994), 4226; Mülsch et al., Brit. J. Pharmacol. 120 (1997), 681]. The more recent stimulators of soluble guanylate cyclase include among others BAY 41-2272, BAY 41-8543 and riociguat (BAY 63-2521) (see, for example, Stasch J.-P. et al., Nat. Rev. Drug Disc. 2006; 5: 755-768; Stasch J.-P. et al., ChemMedChem 2009; 4: 853-865. Stasch J.-P. et al., Circulation 2011; 123: 2263-2273). Interestingly, some of these sGC stimulators, for example YC-1 or BAY 41-2272, also exhibit PDE5-inhibitory action in addition to direct guanylate cyclase stimulation. In order to maximize the cGMP pathway, it is pharmacologically desirable to stimulate the synthesis of cGMP and simultaneously to inhibit degradation via PDE-5. This dual principle is particularly advantageous in pharmacological terms (for example, Oudout et al., Eur. Urol. 2011; 60, 1020-1026; Albersen et al., J Sex Med. 2013; 10, 1268-1277).

The dual principle is fulfilled in the context of the present invention when the inventive compounds exhibit an effect on recombinant guanylate cyclase reporter cell lines according to the study in B-2 as the minimal effective concentration (MEC) of ≤3 µM and exhibit inhibition of human phosphodiesterase-5 (PDE5) according to the study in B-3 as $IC_{50}$<100 nM.

Phosphodiesterase-5 (PDE5) is the name of one of the enzymes which cleave the phosphoric ester bond in cGMP, forming 5'-guanosine monophosphate (5'-GMP). In humans, phosphodiesterase-5 occurs predominantly in the smooth musculature of the corpus cavernosum penis and the pulmonary arteries. Blockage of cGMP degradation by inhibition of PDE5 (with, for example, sildenafil, vardenafil or tadalafil) leads to increased signals of the relaxation signalling pathways and specifically to increased blood supply in the corpus cavernosum penis and lower pressure in the pulmonary blood vessels. They are used for treatment of erectile dysfunction and of pulmonary arterial hypertension. As well as PDE5, there are further cGMP-cleaving phosphodiesterases (Stasch et al. Circulation 2011; 123, 2263-2273).

As stimulators of soluble guanylate cyclase, WO 00/06568 and WO 00/06569 disclose fused pyrazole derivatives, and WO 03/095451 discloses carbamate-substituted 3-pyrimidinylpyrazolopyridines. 3-Pyrimidinylpyrazolopyridines with phenylamide substituents are described in E. M. Becker et al., BMC Pharmacology 1 (13), 2001. WO 2004/009590 describes pyrazolopyridines with substituted 4-aminopyrimidines for the treatment of CNS disorders. WO 2010/065275 and WO 2011/149921 disclose substituted pyrrolo- and dihydropyridopyrimidines as sGC activators. As sGC stimulators, WO 2012/004259 describes fused aminopyrimidines, and WO 2012/004258, WO 2012/143510 and WO 2012/152629 fused pyrimidines and triazines. WO 2012/28647 discloses pyrazolopyridines with various azaheterocycles for treatment of cardiovascular disorders.

It was an object of the present invention to provide novel substances which act as stimulators of soluble guanylate cyclase and also as stimulators of soluble guanylate cyclase and phosphodiesterase-5 inhibitors (dual principle) and have an identical or improved therapeutic profile compared to the compounds known from the prior art, for example with respect to their in vivo properties, for example their pharmacokinetic and pharmacodynamic characteristics and/or their metabolic profile and/or their dose-activity relationship.

The present invention provides compounds of the general formula (I)

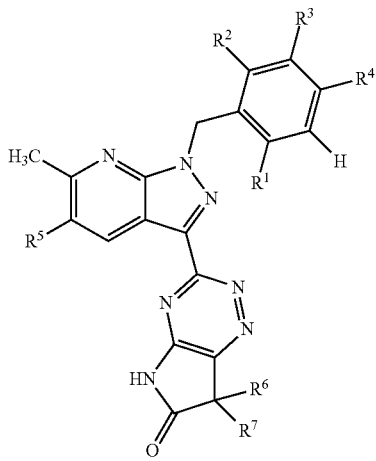

in which
$R^1$ represents hydrogen or fluorine,
$R^2$ represents hydrogen or fluorine,
$R^3$ represents hydrogen, chlorine or fluorine,
$R^4$ represents hydrogen, chlorine, fluorine or methyl,
with the proviso that at least two of the radicals $R^1$, $R^2$, $R^3$ or $R^4$ are different from hydrogen,
$R^5$ represents hydrogen or fluorine,
$R^6$ represents methyl,
$R^7$ represents methyl,
or
$R^6$ and $R^7$ together with the carbon atom to which they are attached form a cyclopropyl ring,
and the N-oxides, salts, solvates, salts of the N-oxides and solvates of the N-oxides or salts thereof.

Compounds according to the invention are the compounds of the formula (I) and their salts, solvates and solvates of the salts, the compounds, comprised by formula (I), of the formulae mentioned below and their salts, solvates and solvates of the salts and the compounds comprised by formula (I), mentioned below as working examples, and their salts, solvates and solvates of the salts, if the compounds, comprised by formula (I), mentioned below are not already salts, solvates and solvates of the salts.

Preferred salts in the context of the present invention are physiologically acceptable salts of the compounds according to the invention. Also encompassed are salts which are not themselves suitable for pharmaceutical applications but can be used, for example, for isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates refer to those forms of the compounds according to the invention which, in the solid or liquid state, form a complex by coordination with solvent molecules. Hydrates are a specific form of solvates in which the coordination is with water. Preferred solvates in the context of the present invention are hydrates.

Where the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulphur, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound according to the invention, especially those in which one or more radioactive isotopes have been incorporated, may be beneficial, for example, for the examination of the mechanism of action or of the active ingredient distribution in the body; due to comparatively easy preparability and detectability, especially compounds labelled with $^{3}H$ or $^{14}C$ isotopes are suitable for this purpose. Furthermore, the incorporation of isotopes, for example of deuterium, can lead to particular therapeutic advantages as a consequence of greater metabolic stability of the compound, for example an extension of the half-life in the body or a reduction in the active dose required; such modifications of the compounds according to the invention may therefore, in some cases, also constitute a preferred embodiment of the present invention. Isotopic variants of the compounds according to the invention can be prepared by the processes known to those skilled in the art, for example by the methods described below and the procedures described in the working examples, by using corresponding isotopic modifications of the respective reagents and/or starting compounds.

Moreover, the present invention also encompasses prodrugs of the compounds according to the invention. Here, the term "prodrugs" refers to compounds which for their part can be biologically active or inactive, but are converted (for example metabolically or hydrolytically) into compounds according to the invention during their dwell time in the body.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" or "preclusion" are used synonymously in the context of the present invention and refer to the avoidance or reduction of the risk of contracting, experiencing, suffering from or having a disease, a condition, a disorder, an injury or a health problem, or a development or progression of such states and/or the symptoms of such states.

The treatment or prevention of a disease, a condition, a disorder, an injury or a health problem may be partial or complete.

In the context of the present invention, preference is given to compounds of the general formula (I)

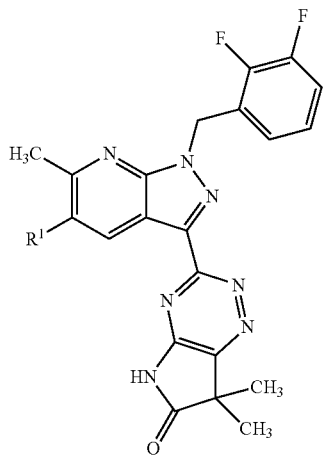

(I)

in which
R¹ represents hydrogen or fluorine,
and the N-oxides, salts, solvates, salts of the N-oxides and solvates of the N-oxides or salts thereof.

In the context of the present invention, preference is given to the compound having the systematic name 3-[1-(2,3-difluorobenzyl)-5-fluoro-6-methyl-1H-pyrazolo[3,4-b]pyridin-3-yl]-7,7-dimethyl-5,7-dihydro-6H-pyrrolo[2,3-e][1,2,4]triazin-6-one and the structural formula (I-A)

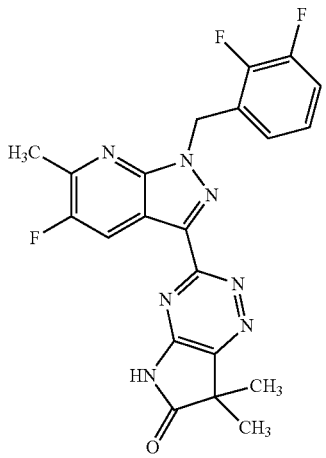

(I-A)

and the N-oxides, salts, solvates, salts of the N-oxides and solvates of the N-oxides or salts thereof.

In the context of the present invention, preference is given to the compound having the systematic name 3-[1-(2,3-difluorobenzyl)-6-methyl-1H-pyrazolo[3,4-b]pyridin-3-yl]-7,7-dimethyl-5,7-dihydro-6H-pyrrolo[2,3-e][1,2,4]triazin-6-one and the structural formula (I-B)

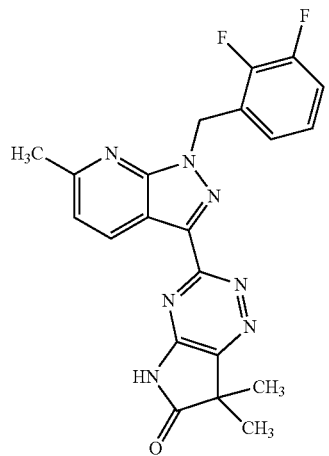

(I-B)

and the N-oxides, salts, solvates, salts of the N-oxides and solvates of the N-oxides or salts thereof.

In the context of the present invention, preference is given to the compound having the systematic name 3-[5-fluoro-1-(2-fluoro-4-methylbenzyl)-6-methyl-1H-pyrazolo[3,4-b]pyridin-3-yl]-7,7-dimethyl-5,7-dihydro-6H-pyrrolo[2,3-e][1,2,4]triazin-6-one and the structural formula (I-C)

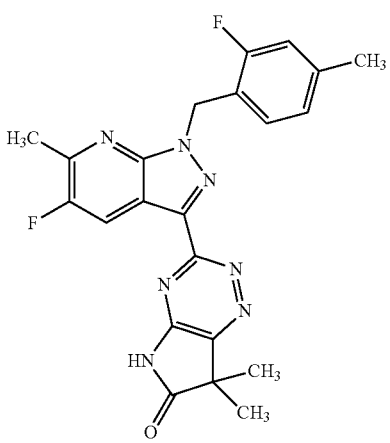

(I-C)

and the N-oxides, salts, solvates, salts of the N-oxides and solvates of the N-oxides or salts thereof.

In the context of the present invention, preference is given to the compound having the systematic name 3-[1-(2-fluoro-4-methylbenzyl)-6-methyl-1H-pyrazolo[3,4-b]pyridin-3-yl]-7,7-dimethyl-5,7-dihydro-6H-pyrrolo[2,3-e][1,2,4]triazin-6-one and the structural formula (I-D)

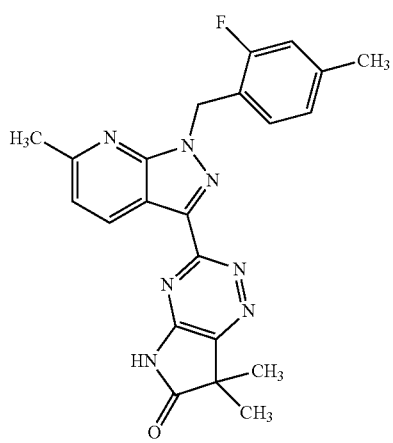

(I-D)

and the N-oxides, salts, solvates, salts of the N-oxides and solvates of the N-oxides or salts thereof.

In the context of the present invention, preference is given to the compound having the systematic name 3-[1-(2,4-difluorobenzyl)-5-fluoro-6-methyl-1H-pyrazolo[3,4-b]pyridin-3-yl]-7,7-dimethyl-5,7-dihydro-6H-pyrrolo[2,3-e][1,2,4]triazin-6-one and the structural formula (I-E)

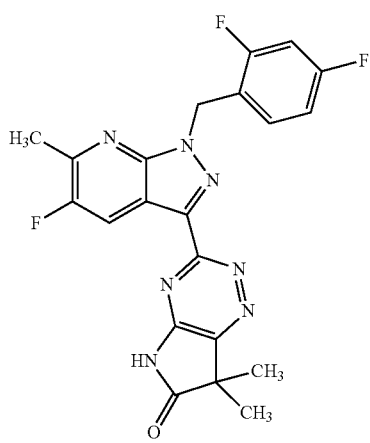

(I-E)

and the N-oxides, salts, solvates, salts of the N-oxides and solvates of the N-oxides or salts thereof.

In the context of the present invention, preference is given to the compound having the systematic name 3-[1-(2,4-difluorobenzyl)-6-methyl-1H-pyrazolo[3,4-b]pyridin-3-yl]-7,7-dimethyl-5,7-dihydro-6H-pyrrolo[2,3-e][1,2,4]triazin-6-one and the structural formula (I-F)

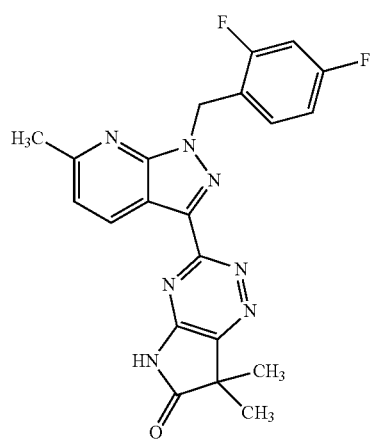

(I-F)

and the N-oxides, salts, solvates, salts of the N-oxides and solvates of the N-oxides or salts thereof.

In the context of the present invention, preference is given to the compound having the systematic name 3-[1-(4-chloro-2-fluorobenzyl)-5-fluoro-6-methyl-1H-pyrazolo[3,4-b]pyridin-3-yl]-7,7-dimethyl-5,7-dihydro-6H-pyrrolo[2,3-e][1,2,4]triazin-6-one and the structural formula (I-G)

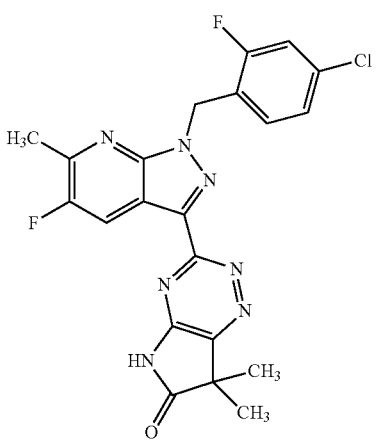

(I-G)

and the N-oxides, salts, solvates, salts of the N-oxides and solvates of the N-oxides or salts thereof.

In the context of the present invention, preference is given to the compound having the systematic name 3-[1-(4-chloro-2-fluorobenzyl)-6-methyl-1H-pyrazolo[3,4-b]pyridin-3-yl]-7,7-dimethyl-5,7-dihydro-6H-pyrrolo[2,3-e][1,2,4]triazin-6-one and the structural formula (I-H)

(I-H)

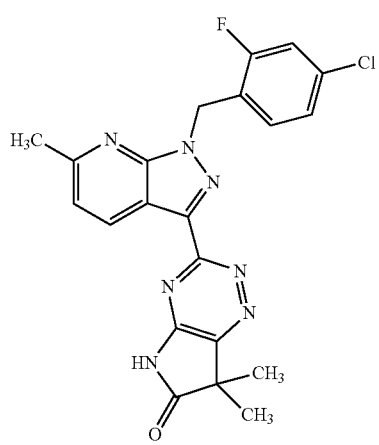

and the N-oxides, salts, solvates, salts of the N-oxides and solvates of the N-oxides or salts thereof.

In the context of the present invention, preference is given to the compound having the systematic name 3-[5-fluoro-6-methyl-1-(2,3,6-trifluorobenzyl)-1H-pyrazolo[3,4-b]pyridin-3-yl]-7,7-dimethyl-5,7-dihydro-6H-pyrrolo[2,3-e][1,2,4]triazin-6-one and the structural formula (I-I)

(I-I)

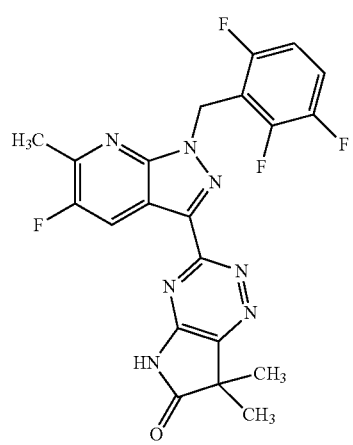

and the N-oxides, salts, solvates, salts of the N-oxides and solvates of the N-oxides or salts thereof.

In the context of the present invention, preference is given to the compound having the systematic name 7,7-dimethyl-3-[6-methyl-1-(2,3,6-trifluorobenzyl)-1H-pyrazolo[3,4-b]pyridin-3-yl]-5,7-dihydro-6H-pyrrolo[2,3-e][1,2,4]triazin-6-one and the structural formula (I-J)

(I-J)

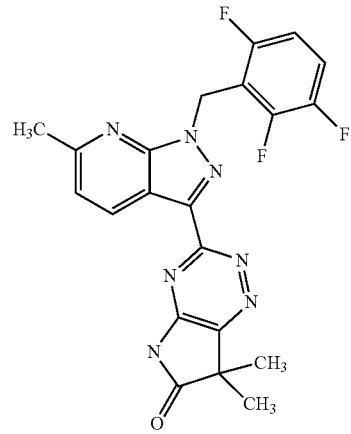

and the N-oxides, salts, solvates, salts of the N-oxides and solvates of the N-oxides or salts thereof.

In the context of the present invention, preference is given to the compound having the systematic name 3-[1-(3-chloro-2-fluorobenzyl)-5-fluoro-6-methyl-1H-pyrazolo[3,4-b]pyridin-3-yl]-7,7-dimethyl-5,7-dihydro-6H-pyrrolo[2,3-e][1,2,4]triazin-6-one and the structural formula (I-K)

(I-K)

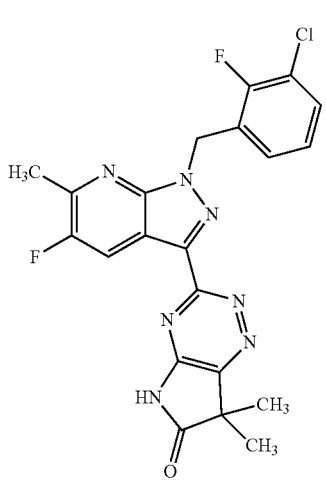

and the N-oxides, salts, solvates, salts of the N-oxides and solvates of the N-oxides or salts thereof.

In the context of the present invention, preference is given to the compound having the systematic name 3-[1-(3-chloro-2-fluorobenzyl)-6-methyl-1H-pyrazolo[3,4-b]pyridin-3-yl]-7,7-dimethyl-5,7-dihydro-6H-pyrrolo[2,3-e][1,2,4]triazin-6-one and the structural formula (I-L)

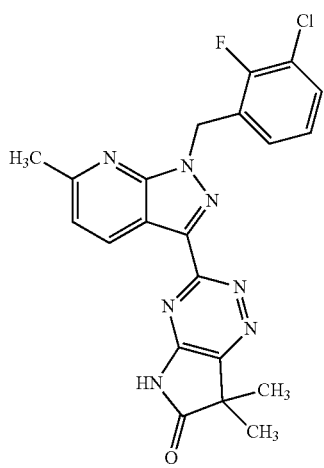

(I-L)

and the N-oxides, salts, solvates, salts of the N-oxides and solvates of the N-oxides or salts thereof.

In the context of the present invention, preference is given to the compound having the systematic name 3-[1-(2,6-difluorobenzyl)-5-fluoro-6-methyl-1H-pyrazolo[3,4-b]pyridin-3-yl]-7,7-dimethyl-5,7-dihydro-6H-pyrrolo[2,3-e][1,2,4]triazin-6-one and the structural formula (I-M)

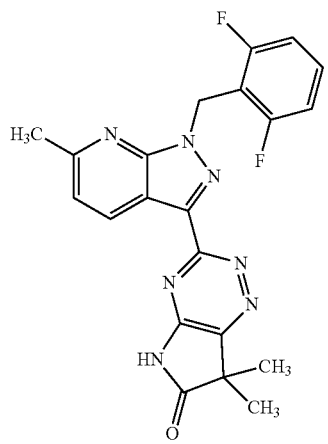

(I-N)

and the N-oxides, salts, solvates, salts of the N-oxides and solvates of the N-oxides or salts thereof.

In the context of the present invention, preference is given to the compound having the systematic name 3-[5-fluoro-1-(3-fluoro-4-methylbenzyl)-6-methyl-1H-pyrazolo[3,4-b]pyridin-3-yl]-7,7-dimethyl-5,7-dihydro-6H-pyrrolo[2,3-e][1,2,4]triazin-6-one and the structural formula (I-O)

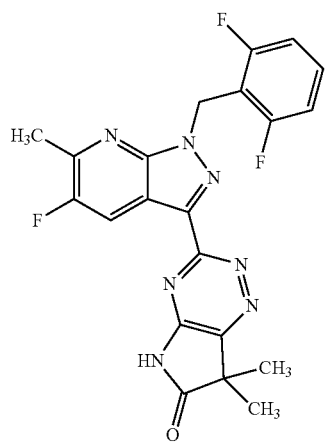

(I-M)

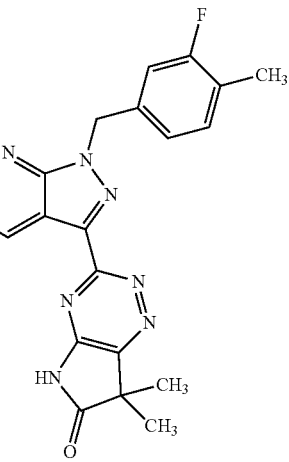

(I-O)

and the N-oxides, salts, solvates, salts of the N-oxides and solvates of the N-oxides or salts thereof.

In the context of the present invention, preference is given to the compound having the systematic name 3-[1-(2,6-difluorobenzyl)-6-methyl-1H-pyrazolo[3,4-b]pyridin-3-yl]-7,7-dimethyl-5,7-dihydro-6H-pyrrolo[2,3-e][1,2,4]triazin-6-one and the structural formula (I-N)

and the N-oxides, salts, solvates, salts of the N-oxides and solvates of the N-oxides or salts thereof.

In the context of the present invention, preference is given to the compound having the systematic name 3-[1-(3-fluoro-4-methylbenzyl)-6-methyl-1H-pyrazolo[3,4-b]pyridin-3-yl]-7,7-dimethyl-5,7-dihydro-6H-pyrrolo[2,3-e][1,2,4]triazin-6-one and the structural formula (I-P)

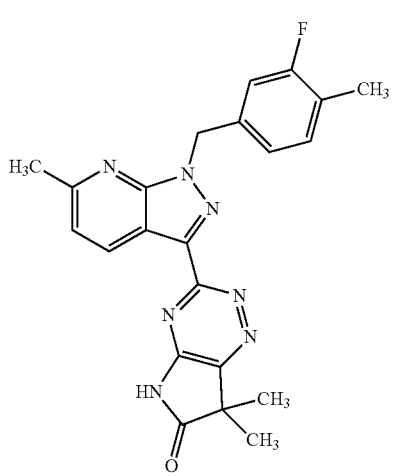

(I-P)

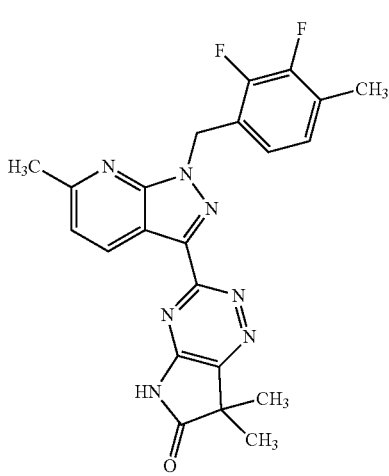

(I-R)

and the N-oxides, salts, solvates, salts of the N-oxides and solvates of the N-oxides or salts thereof.

In the context of the present invention, preference is given to the compound having the systematic name 3-[1-(2,3-difluoro-4-methylbenzyl)-5-fluoro-6-methyl-1H-pyrazolo[3,4-b]pyridin-3-yl]-7,7-dimethyl-5,7-dihydro-6H-pyrrolo[2,3-e][1,2,4]triazin-6-one and the structural formula (I-Q)

and the N-oxides, salts, solvates, salts of the N-oxides and solvates of the N-oxides or salts thereof.

In the context of the present invention, preference is given to the compound having the systematic name 3'-[1-(2,3-difluoro-4-methylbenzyl)-5-fluoro-6-methyl-1H-pyrazolo[3,4-b]pyridin-3-yl]spiro-[cyclopropane-1,7'-pyrrolo[2,3-e][1,2,4]triazin]-6'(5'H)-one and the structural formula (I-S)

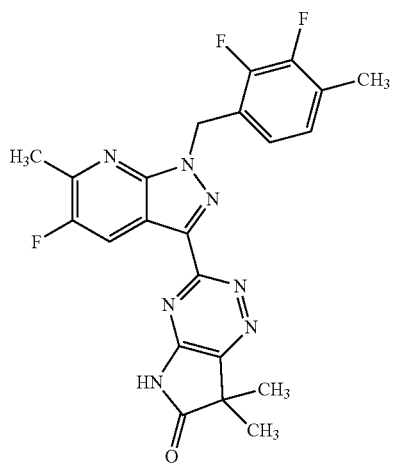

(I-Q)

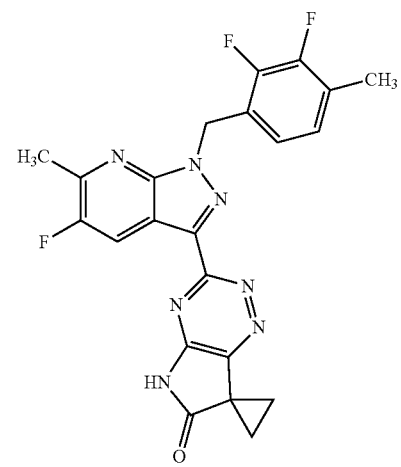

(I-S)

and the N-oxides, salts, solvates, salts of the N-oxides and solvates of the N-oxides or salts thereof.

In the context of the present invention, preference is given to the compound having the systematic name 3-[1-(2,3-difluoro-4-methylbenzyl)-6-methyl-1H-pyrazolo[3,4-b]pyridin-3-yl]-7,7-dimethyl-5,7-dihydro-6H-pyrrolo[2,3-e][1,2,4]triazin-6-one and the structural formula (I-R)

and the N-oxides, salts, solvates, salts of the N-oxides and solvates of the N-oxides or salts thereof.

In the context of the present invention, preference is given to the compound having the systematic name 3'-[1-(2,3-difluoro-4-methylbenzyl)-6-methyl-1H-pyrazolo[3,4-b]pyridin-3-yl]spiro-[cyclopropane-1,7'-pyrrolo[2,3-e][1,2,4]triazin]-6'(5'H)-one and the structural formula (I-T)

(I-T)

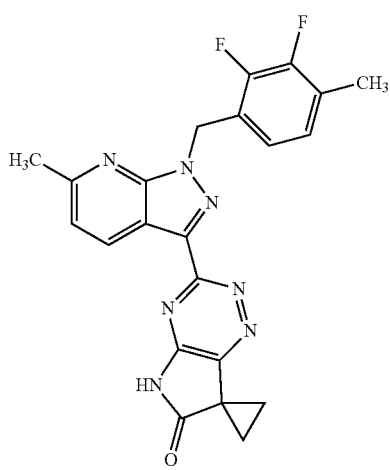

and the N-oxides, salts, solvates, salts of the N-oxides and solvates of the N-oxides or salts thereof.

In the context of the present invention, preference is given to the compound having the systematic name 3'-[5-fluoro-1-(2-fluoro-4-methylbenzyl)-6-methyl-1H-pyrazolo[3,4-b]pyridin-3-yl]spiro-[cyclopropane-1,7'-pyrrolo[2,3-e][1,2,4]triazin]-6'(5'H)-one and the structural formula (I-U)

(I-U)

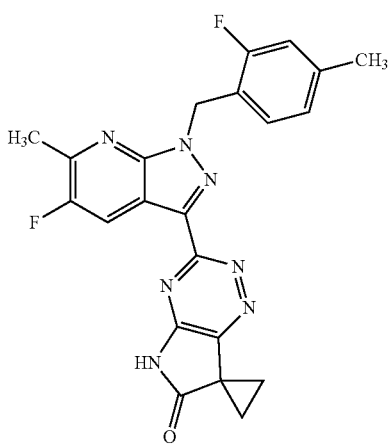

and the N-oxides, salts, solvates, salts of the N-oxides and solvates of the N-oxides or salts thereof.

In the context of the present invention, preference is given to the compound having the systematic name 3'-[1-(2-fluoro-4-methylbenzyl)-6-methyl-1H-pyrazolo[3,4-b]pyridin-3-yl]spiro[cyclopropane-1,7'-pyrrolo[2,3-e][1,2,4]triazin]-6'(5'H)-one and the structural formula (I-V)

(I-V)

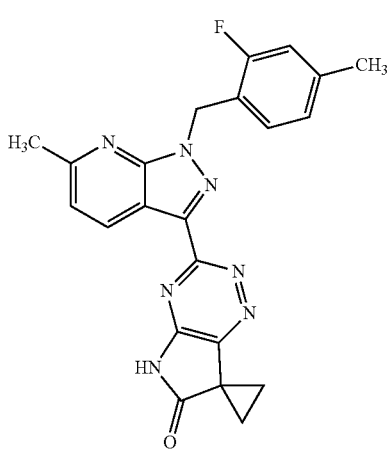

and the N-oxides, salts, solvates, salts of the N-oxides and solvates of the N-oxides or salts thereof.

In the context of the present invention, preference is given to the compound having the systematic name 3'-[1-(2,3-difluorobenzyl)-5-fluoro-6-methyl-1H-pyrazolo[3,4-b]pyridin-3-yl]spiro[cyclopropane-1,7'-pyrrolo[2,3-e][1,2,4]triazin]-6'(5'H)-one and the structural formula (I-W)

(I-W)

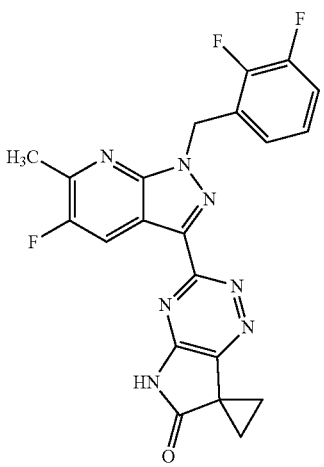

and the N-oxides, salts, solvates, salts of the N-oxides and solvates of the N-oxides or salts thereof.

In the context of the present invention, preference is given to the compound having the systematic name 3'-[1-(2,3-difluorobenzyl)-6-methyl-1H-pyrazolo[3,4-b]pyridin-3-yl]spiro[cyclopropane-1,7'-pyrrolo[2,3-e][1,2,4]triazin]-6'(5'H)-one and the structural formula (I-X)

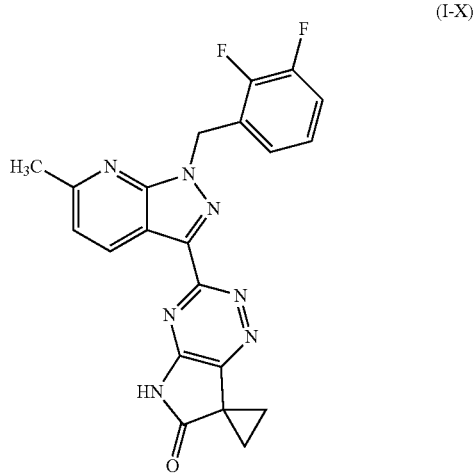 [SMILES: Cc1ccc2c(-c3nnc4c(n3)NC(=O)C43CC3)nn(Cc3cccc(F)c3F)c2n1]

(I-X)

and the N-oxides, salts, solvates, salts of the N-oxides and solvates of the N-oxides or salts thereof.

The compounds according to the invention act as potent stimulators of soluble guanylate cyclase and inhibitors of phosphodiesterase-5, have useful pharmacological properties and have an improved therapeutic profile, for example with respect to the in vivo properties thereof and/or the pharmacokinetic characteristics and/or metabolic profile thereof. They are therefore suitable for the treatment and/or prophylaxis of diseases in humans and animals.

The compounds according to the invention bring about vasorelaxation and inhibition of platelet aggregation, and lead to a decrease in blood pressure and to a rise in coronary blood flow. These effects are mediated by a direct stimulation of soluble guanylate cyclase and an intracellular rise in cGMP. In addition, the compounds according to the invention enhance the action of substances which increase the cGMP level, for example EDRF (endothelium-derived relaxing factor), NO donors, protoporphyrin IX, arachidonic acid or phenylhydrazine derivatives.

The compounds according to the invention are suitable for the treatment and/or prophylaxis of cardiovascular, pulmonary, thromboembolic and fibrotic disorders.

Accordingly, the compounds according to the invention can be used in medicaments for the treatment and/or prophylaxis of cardiovascular disorders such as, for example, hypertension, resistant hypertension, acute and chronic heart failure, coronary heart disease, stable and unstable angina pectoris, peripheral and cardiac vascular disorders, arrhythmias, atrial and ventricular arrhythmias and impaired conduction such as, for example, atrioventricular blocks degrees I-III (AB block I-III), supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes, AV-nodal re-entry tachycardia, Wolff-Parkinson-White syndrome, of acute coronary syndrome (ACS), autoimmune cardiac disorders (pericarditis, endocarditis, valvolitis, aortitis, cardiomyopathies), shock such as cardiogenic shock, septic shock and anaphylactic shock, aneurysms, boxer cardiomyopathy (premature ventricular contraction (PVC)), for the treatment and/or prophylaxis of thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, to prevent restenoses, for example after thrombolysis therapies, percutaneous transluminal angioplasties (PTA), transluminal coronary angioplasties (PTCA), heart transplants and bypass operations, and also micro- and macrovascular damage (vasculitis), increased levels of fibrinogen and of low-density lipoprotein (LDL) and increased concentrations of plasminogen activator inhibitor 1 (PAI-1), and also for the treatment and/or prophylaxis of erectile dysfunction and female sexual dysfunction.

In the context of the present invention, the term "heart failure" encompasses both acute and chronic forms of heart failure, and also more specific or related types of disease, such as acute decompensated heart failure, right heart failure, left heart failure, global failure, ischaemic cardiomyopathy, dilated cardiomyopathy, hypertrophic cardiomyopathy, idiopathic cardiomyopathy, congenital heart defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, diastolic heart failure and systolic heart failure, and acute phases of worsening of existing chronic heart failure (worsening heart failure).

In addition, the compounds according to the invention can also be used for the treatment and/or prophylaxis of arteriosclerosis, impaired lipid metabolism, hypolipoproteinaemias, dyslipidaemias, hypertriglyceridaemias, hyperlipidaemias, hypercholesterolaemias, abetalipoproteinaemia, sitosterolaemia, xanthomatosis, Tangier disease, adiposity, obesity and of combined hyperlipidaemias and metabolic syndrome.

The compounds according to the invention can additionally be used for the treatment and/or prophylaxis of primary and secondary Raynaud's phenomenon, of microcirculation impairments, claudication, peripheral and autonomic neuropathies, diabetic microangiopathies, diabetic retinopathy, diabetic ulcers on the extremities, gangrene, CREST syndrome, erythematosis, onychomycosis, rheumatic disorders and for promoting wound healing. The compounds according to the invention are also suitable for the treatment of muscular dystrophy, such as Becker-Kiener muscular dystrophy (BMD) and Duchenne muscular dystrophy (DMD).

The compounds according to the invention are furthermore suitable for treating urological disorders such as, for example, benign prostate syndrome (BPS), benign prostate hyperplasia (BPH), benign prostate enlargement (BPE), bladder outlet obstruction (BOO), lower urinary tract syndromes (LUTS, including Feline Urological Syndrome (FUS)), disorders of the urogenital system including neurogenic overactive bladder (OAB) and (IC), incontinence (UI) such as, for example, mixed urinary incontinence, urge urinary incontinence, stress urinary incontinence or overflow urinary incontinence (MUI, UUI, SUI, OUI), pelvic pain, benign and malignant disorders of the organs of the male and female urogenital system.

The compounds according to the invention are furthermore suitable for the treatment and/or prophylaxis of kidney disorders, in particular of acute and chronic renal insufficiency and acute and chronic renal failure. In the context of the present invention, the term renal insufficiency comprises both acute and chronic manifestations thereof, as well as underlying or related kidney diseases such as renal hypoperfusion, intradialytic hypotension, obstructive uropathy, glomerulopathies, glomerulonephritis, acute glomerulonephritis, glomerulosclerosis, tubulointerstitial diseases, nephropathic diseases such as primary and congenital kidney disease, nephritis, immunological kidney diseases such as kidney graft rejection and immunocomplex-induced kidney diseases, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome, which can be characterized diagnostically for example by abnormally reduced creatinine and/or water excretion, abnormally raised blood concentrations of urea, nitrogen, potassium and/or creatinine, altered activity of renal enzymes such as, for example, glutamyl synthetase, altered urine osmolarity or urine volume, increased microalbuminuria, macroalbuminuria, lesions on glomerulae and arterioles, tubular dilatation, hyperphosphataemia and/or need for dialysis. The present invention also encompasses the use of the compounds according to the invention for the treatment and/or prophylaxis of sequelae of renal insufficiency, for example pulmonary oedema, heart failure, uraemia, anaemia, electrolyte disturbances (for example hyperkalaemia, hyponatraemia) and disturbances in bone and carbohydrate metabolism.

Furthermore, the compounds according to the invention are also suitable for the treatment and/or prophylaxis of asthmatic disorders, pulmonary arterial hypertension (PAH) and other forms of pulmonary hypertension (PH) including left-heart disease, HIV, sickle cell anaemia, thromboembolisms (CTEPH), sarcoidosis, COPD or pulmonary fibrosis-associated pulmonary hypertension, chronic-obstructive pulmonary disease (COPD), acute respiratory distress syndrome (ARDS), acute lung injury (ALI), alpha-1-antitrypsin deficiency (AATD), pulmonary fibrosis, pulmonary emphysema (for example pulmonary emphysema induced by cigarette smoke) and cystic fibrosis (CF). In addition, the compounds mentioned can be used as bronchodilators.

The compounds described in the present invention are also active compounds for control of central nervous system disorders characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelinization, multiple sclerosis, thalamic degeneration, Creutzfeld-Jacob dementia, HIV dementia, schizophrenia with dementia or Korsakoff's psychosis. They are also suitable for the treatment and/or prophylaxis of central nervous system disorders such as states of anxiety, tension and depression, CNS-related sexual dysfunctions and sleep disturbances, and for controlling pathological disturbances of the intake of food, stimulants and addictive substances.

Furthermore, the compounds according to the invention are also suitable for regulating cerebral blood flow and are thus effective agents for control of migraine. They are also suitable for the prophylaxis and control of sequelae of cerebral infarction (cerebral apoplexy) such as stroke, cerebral ischaemia and craniocerebral trauma. The compounds according to the invention can likewise be employed for controlling states of pain and tinnitus.

In addition, the compounds according to the invention have antiinflammatory action and can therefore be used as antiinflammatory agents for the treatment and/or prophylaxis of sepsis (SIRS), multiple organ failure (MODS, MOF), inflammatory disorders of the kidney, chronic intestinal inflammations (IBD, Crohn's disease, UC), pancreatitis, peritonitis, rheumatoid disorders, inflammatory skin diseases and inflammatory eye diseases.

Furthermore, the compounds according to the invention can also be used for the treatment and/or prophylaxis of autoimmune diseases.

The compounds according to the invention are furthermore suitable for the treatment and/or prophylaxis of fibrotic disorders of the internal organs such as, for example, the lung, the heart, the kidney, the bone marrow and in particular the liver, and also dermatological fibroses and fibrotic eye disorders. In the context of the present invention, the term fibrotic disorders includes in particular the following terms: hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy, proliferative vitroretinopathy and disorders of the connective tissue (for example sarkoidosis).

The compounds according to the invention are furthermore suitable for controlling postoperative scarring, for example as a result of glaucoma operations.

The compounds according to the invention can also be used cosmetically for ageing and keratinized skin.

Moreover, the compounds according to the invention are suitable for the treatment and/or prophylaxis of hepatitis, neoplasms, osteoporosis, glaucoma and gastroparesis.

The present invention further provides for the use of the compounds according to the invention for the treatment and/or prophylaxis of disorders, in particular the disorders mentioned above.

The present invention further provides for the use of the compounds according to the invention for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides the compounds according to the invention for use in a method for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides for the use of the compounds according to the invention for producing a medicament for the treatment and/or prophylaxis of disorders, in particular the disorders mentioned above.

The present invention further provides for the use of the compounds according to the invention for producing a medicament for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis.

The present invention further provides a method for the treatment and/or prophylaxis of disorders, in particular the disorders mentioned above, using an effective amount of at least one of the compounds according to the invention.

The present invention further provides a method for the treatment and/or prophylaxis of heart failure, angina pectoris, hypertension, pulmonary hypertension, ischaemias, vascular disorders, renal insufficiency, thromboembolic disorders, fibrotic disorders and arteriosclerosis using an effective amount of at least one of the compounds according to the invention.

The compounds according to the invention can be employed alone or, if required, in combination with other active compounds. The present invention further provides medicaments comprising at least one of the compounds according to the invention and one or more further active compounds, especially for the treatment and/or prophylaxis of the aforementioned disorders. Preferred examples of suitable active compound combinations include:

organic nitrates and NO donors, for example sodium nitroprusside, nitroglycerin, isosorbide mononitrate, isosorbide dinitrate, molsidomine or SIN-1, and inhaled NO;

compounds which inhibit the breakdown of cyclic guanosine monophosphate (cGMP), for example inhibitors of phosphodiesterases (PDE) 1, 2 and/or 5, especially PDE 5 inhibitors such as sildenafil, vardenafil and tadalafil;

antithrombotic agents, by way of example and with preference from the group of the platelet aggregation inhibitors, the anticoagulants or the profibrinolytic substances;

hypotensive active compounds, by way of example and with preference from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics; and/or active compounds which alter lipid metabolism, for example and with preference from the group of the thyroid receptor agonists, cholesterol synthesis inhibitors such as, by way of example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists.

Antithrombotic agents are preferably understood to mean compounds from the group of the platelet aggregation inhibitors, the anticoagulants or the profibrinolytic substances.

In a preferred embodiment of the invention, the compounds according to the invention are administered in combination with a platelet aggregation inhibitor, by way of example and with preference aspirin, clopidogrel, ticlopidin or dipyridamole.

In a preferred embodiment of the invention, the compounds according to the invention are administered in combination with a thrombin inhibitor, by way of example and with preference ximelagatran, dabigatran, melagatran, bivalirudin or clexane.

In a preferred embodiment of the invention, the compounds according to the invention are administered in combination with a GPIIb/IIIa antagonist such as, by way of example and with preference, tirofiban or abciximab.

In a preferred embodiment of the invention, the inventive compounds are administered in combination with a factor Xa inhibitor, preferred examples being rivaroxaban, DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, alpha-receptor blockers, beta-receptor blockers, mineralocorticoid receptor antagonists, and the diuretics.

In a preferred embodiment of the invention, the compounds according to the invention are administered in combination with a calcium antagonist, by way of example and with preference nifedipine, amlodipine, verapamil or diltiazem.

In a preferred embodiment of the invention, the compounds according to the invention are administered in combination with an alpha-1-receptor blocker, by way of example and with preference prazosin.

In a preferred embodiment of the invention, the compounds according to the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, by way of example and with preference losartan, candesartan, valsartan, telmisartan or embusartan.

In a preferred embodiment of the invention, the compounds according to the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds according to the invention are administered in combination with an endothelin antagonist, by way of example and with preference bosentan, darusentan, ambrisentan or sitaxsentan.

In a preferred embodiment of the invention, the compounds according to the invention are administered in combination with a renin inhibitor, by way of example and with preference aliskiren, SPP-600 or SPP-800.

In a preferred embodiment of the invention, the compounds according to the invention are administered in combination with a mineralocorticoid receptor antagonist, by way of example and with preference spironolactone or eplerenone.

In a preferred embodiment of the invention, the compounds according to the invention are administered in combination with a loop diuretic, for example furosemide, torasemide, bumetanide and piretanide, with potassium-sparing diuretics, for example amiloride and triamterene, with aldosterone antagonists, for example spironolactone, potassium canreonate and eplerenone, and also thiazide diuretics, for example hydrochlorothiazide, chlorthalidone, xipamide and indapamide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein(a) antagonists.

In a preferred embodiment of the invention, the compounds according to the invention are administered in combination with a CETP inhibitor, by way of example and with preference dalcetrapib, BAY 60-5521, anacetrapib or CETP vaccine (CETi-1).

In a preferred embodiment of the invention, the compounds according to the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, by way of example and with preference BMS-188494 or TAK-475.

In a preferred embodiment of the invention, the compounds according to the invention are administered in combination with an ACAT inhibitor, by way of example and with preference avasimibe, melinamide, pactimibe, eflucimibe or SMP-797.

In a preferred embodiment of the invention, the compounds according to the invention are administered in combination with an MTP inhibitor, by way of example and with preference implitapide, BMS-201038, R-103757 or JTT-130.

In a preferred embodiment of the invention, the compounds according to the invention are administered in combination with a PPAR-gamma agonist, by way of example and with preference pioglitazone or rosiglitazone.

In a preferred embodiment of the invention, the compounds according to the invention are administered in combination with a PPAR-delta agonist, by way of example and with preference GW 501516 or BAY 68-5042.

In a preferred embodiment of the invention, the compounds according to the invention are administered in combination with a cholesterol absorption inhibitor, by way of example and with preference ezetimibe, tiqueside or pamaqueside.

In a preferred embodiment of the invention, the compounds according to the invention are administered in combination with a lipase inhibitor, a preferred example being orlistat.

In a preferred embodiment of the invention, the compounds according to the invention are administered in combination with a polymeric bile acid adsorbent, by way of example and with preference cholestyramine, colestipol, colesolvam, CholestaGel or colestimide.

In a preferred embodiment of the invention, the compounds according to the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds according to the invention are administered in combination with a lipoprotein(a) antagonist, by way of example and with preference gemcabene calcium (CI-1027) or nicotinic acid.

The present invention further provides medicaments which comprise at least one compound according to the invention, typically together with one or more inert, nontoxic, pharmaceutically suitable excipients, and for the use thereof for the aforementioned purposes.

The compounds according to the invention may act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in administration forms suitable for these administration routes.

Administration forms which function according to the prior art, release the compounds according to the invention rapidly and/or in a modified manner and contain the compounds according to the invention in crystalline and/or amorphized and/or dissolved form are suitable for oral administration, such as e.g. tablets (non-coated or coated tablets, for example with enteric coatings or coatings that dissolve in a delayed manner or are insoluble and control the release of the compound according to the invention), tablets or films/oblates, films/lyophilisates or capsules which disintegrate rapidly in the oral cavity (for example hard or soft gelatine capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e.g. intramuscularly, subcutaneously, intracutaneously, percutaneously or intraperitoneally). Suitable administration forms for parenteral administration include injection and infusion formulations in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Preference is given to oral or parenteral administration, especially oral administration.

The compounds according to the invention can be converted to the administration forms mentioned. This can be done in a manner known per se, by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavour and/or odour correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration, the dose is about 0.001 to 2 mg/kg, preferably about 0.001 to 1 mg/kg, of body weight.

It may nevertheless be necessary where appropriate to deviate from the stated amounts, specifically as a function of the body weight, route of administration, individual response to the active compound, nature of the preparation and time or interval over which administration takes place. For instance, in some cases, less than the aforementioned minimum amount may be sufficient, while in other cases the upper limit mentioned must be exceeded. In the case of administration of greater amounts, it may be advisable to divide them into several individual doses over the day.

The working examples which follow illustrate the invention. The invention is not limited to the examples.

The percentages in the tests and examples which follow are, unless indicated otherwise, percentages by weight; parts are parts by weight. Solvent ratios, dilution ratios and concentration figures for liquid/liquid solutions are each based on volume.

A. EXAMPLES

Abbreviations and Acronyms abs. absolute
aq. aqueous solution
calc. calculated
br. s broad singlet (in NMR)
DCI direct chemical ionization (in MS)
DMF dimethylformamide
DMSO dimethyl sulphoxide
eq. equivalent(s)
ESI electrospray ionization (in MS)
Et ethyl
h hour(s)
HPLC high-pressure, high-performance liquid chromatography
HRMS high-resolution mass spectrometry
conc. concentrated
LC-MS liquid chromatography-coupled mass spectrometry
Me methyl
min minute(s)
MS mass spectrometry
NMR nuclear magnetic resonance spectrometry
$PdCl_2(dppf)CH_2Cl_2$ 1,1'-bis(diphenylphosphino)ferrocenepalladium(II) dichloride/dichloromethane complex
Ph phenyl
RT room temperature
$R_t$ retention time (in HPLC)
SFC supercritical fluid chromatography
THF tetrahydrofuran
UV ultraviolet spectrometry
v/v ratio by volume (of a solution)

The purity is the purity according to LCMS unless another method is specifically mentioned.

LC/MS and MS Methods:

Method 1 (LC-MS):

Instrument: Waters ACQUITY SQD UPLC System; column: Waters Acquity UPLC HSS T3 1.8μ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; oven: 50° C.; flow rate: 0.40 ml/min; UV detection: 208-400 nm.

Method 2 (LC-MS):

MS instrument: Waters (Micromass) Quattro Micro; HPLC instrument: Agilent 1100 series; column: YMC-Triart C18 3μ 50×3 mm; mobile phase A: 1 l of water+0.01 mol of ammonium carbonate, mobile phase B: 1 l of acetonitrile; gradient: 0.0 min 100% A→2.75 min 5% A→4.5 min 5% A; oven: 40° C.; flow rate: 1.25 ml/min; UV detection: 210 nm.

Method 3 (LC-MS):

MS instrument: Waters (Micromass) QM; HPLC instrument: Agilent 1100 series; column: Agilent ZORBAX Extend-C18 3.0×50 mm 3.5 micron; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 4 (LC-MS):

Instrument: Waters ACQUITY SQD UPLC System; column: Waters Acquity UPLC HSS T3 1.8μ 50×1 mm; mobile phase A: 1 l of water+0.25 ml of 99% strength formic acid, mobile phase B: 1 l of acetonitrile+0.25 ml of 99% strength formic acid; gradient: 0.0 min 95% A→6.0 min 5% A→7.5 min 5% A; oven: 50° C.; flow rate: 0.35 ml/min; UV detection: 210-400 nm.

Method 5 (LC-MS):

Instrument: Micromass Quattro Premier with Waters UPLC Acquity; column: Thermo Hypersil GOLD 1.9μ 50×1 mm; mobile phase A: 1 l of water+0.5 ml of 50% strength formic acid, mobile phase B: 1 l of acetonitrile+0.5 ml of 50% strength formic acid; gradient 0.0 min 97% A→0.5 min 97% A→3.2 min 5% A→4.0 min 5% A; oven: 50° C.; flow rate: 0.3 ml/min; UV detection: 210 nm.

Method 6 (LC-MS):

MS instrument: Waters (Micromass) Quattro Micro; HPLC instrument: Agilent 1100 series; column: YMC-Triart C18 3μ 50×3 mm; mobile phase A: 1 l of water+0.01 mol of ammonium carbonate, mobile phase B: 1 l of acetonitrile; gradient: 0.0 min 100% A→2.75 min 5% A→4.5 min 5% A; oven: 40° C.; flow rate: 1.25 ml/min; UV detection: 210 nm.

Method 7 (LC-MS):

MS instrument: Waters (Micromass) QM; HPLC instrument: Agilent 1100 series; column: Agilent ZORBAX Extend-C18 3.0×50 mm 3.5 micron; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm.

Method 8 (GC-MS):

Instrument: Thermo DFS, Trace GC Ultra; column: Restek RTX-35, 15 m×200 μm×0.33 μm; constant helium flow rate: 1.20 ml/min; oven: 60° C.; inlet: 220° C.; gradient: 60° C., 30° C./min→300° C. (maintained for 3.33 min).

Starting Materials and Intermediates:

Example 1A

5-Fluoro-6-methyl-1H-pyrazolo[3,4-b]pyridine-3-amine

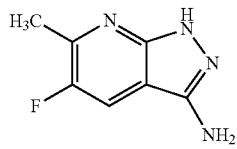

58 g (340.027 mmol) of 2-chloro-5-fluoro-6-methylnicotinonitrile (preparation described in WO2007/41052, Example U-2, page 80) were initially charged in 1,2-ethanediol (580 ml), and hydrazine hydrate (24.813 ml) and 56.091 ml (340.027 mmol) of diisopropylethylamine were then added. With stirring, the mixture was heated at 80° C. for 16 h and then at 120° C. for 6 h. After cooling, water (2.5 l) and ethyl acetate (2.5 l) were added, and the mixture was filtered off with suction. The solid obtained was dried. This gave 28.4 g (47% of theory) of the target compound.

LC-MS (Method 2): $R_t$=1.77 min
MS (ESIpos): m/z=167 (M+H)$^+$

Example 2A

5-Fluoro-3-iodo-6-methyl-1H-pyrazolo[3,4-b]pyridine

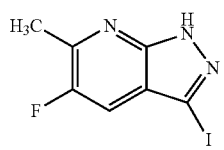

28 g (168.5 mmol) of 5-fluoro-6-methyl-1H-pyrazolo[3,4-b]pyridine-3-amine from Example 1A were initially charged in 1.32 l of THF, and the mixture was cooled to 0° C. 41.45 ml (337.03 mmol) of boron trifluoride diethyl ether complex were then added slowly. The reaction mixture was cooled to −10° C. A solution of 25.66 g (219.07 mmol) of isopentyl nitrite in 166 ml of THF was then added slowly, and the mixture was stirred for a further 30 min. The reaction solution was concentrated such that 75% of the THF were removed. 988 ml of acetone were added, and the solution was cooled to 0° C. A solution of 32.84 g (219.07 mmol) of sodium iodide in 412 ml of acetone was added dropwise to this solution, and the mixture was stirred at RT for 2 h. The reaction mixture was poured into 5 l of ice-water and extracted three times with in each case 750 ml of ethyl acetate. The combined organic phases were washed with 750 ml of saturated aqueous sodium chloride solution, dried and then concentrated under reduced pressure. The crude product was purified by silica gel chromatography (cyclohexane/ethyl acetate gradient: 9:1 to 1:1). This gave 14.90 g (32% of theory) of the title compound.

LC-MS (Method 1): $R_t$=0.84 min
MS (ESIpos): m/z=278 (M+H)$^+$

Example 3A 1-(2,3-Difluorobenzyl)-5-fluoro-3-iodo-6-methyl-1H-pyrazolo[3,4-b]pyridine

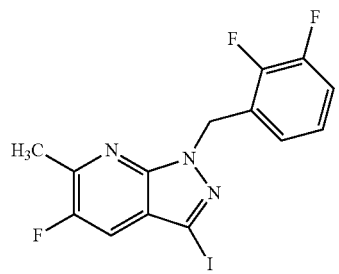 [SMILES: Cc1nc2c(cc1F)c(I)nn2Cc1cccc(F)c1F]

2.60 g (9.37 mmol) of 5-fluoro-3-iodo-6-methyl-1H-pyrazolo[3,4-b]pyridine from Example 2A were initially charged in 35 ml of DMF. 3.67 g (11.26 mmol) of caesium carbonate and 1.94 g (9.37 mmol) of 1-(bromomethyl)-2,3-difluorobenzene, dissolved in 10 ml of DMF, were then added and the mixture was stirred at RT overnight. The reaction mixture was added to 200 ml of water and extracted twice with ethyl acetate. The combined organic phases were dried over sodium sulphate, filtered and concentrated. The residue was chromatographed on silica gel (mobile phase: petroleum ether/ethyl acetate=10/1) and the product fractions were concentrated. The product was purified further by chromatography: column: Sunfire C18, 5 μm, 250×20 mm; mobile phase: 12% water+85% methanol+3% 1% strength aqueous TFA solution; flow rate: 25 ml/min; temperature: 40° C.; wavelength: 210 nm. This gave 2.67 g (71% of theory) of the title compound.

LC-MS (Method 1): $R_t$=1.29 min
MS (ESIpos): m/z=404 (M+H)$^+$

Example 4A 1-(2,3-Difluorobenzyl)-5-fluoro-6-methyl-1H-pyrazolo[3,4-b]pyridine-3-carbonitrile

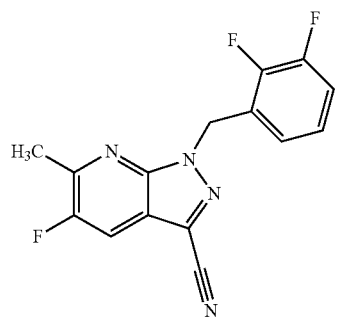 [SMILES: Cc1nc2c(cc1F)c(C#N)nn2Cc1cccc(F)c1F]

Variant A:
A mixture of 2.47 g (6.13 mmol) of 1-(2,3-difluorobenzyl)-5-fluoro-3-iodo-6-methyl-1H-pyrazolo[3,4-b]pyridine from Example 3A and 0.576 g (6.43 mmol) of copper(I) cyanide was initially charged in 12.1 ml of abs. DMSO in a flask which had been dried by heating, and the mixture was stirred at 150° C. for 3 h. Ethyl acetate was added to the cooled reaction solution, and the mixture was washed three times with a mixture of semisaturated ammonium chloride solution and concentrated ammonia solution (3/1). The organic phase was dried over sodium sulphate, filtered and concentrated. The crude product was purified by flash chromatography (mobile phase: cyclohexane/ethyl acetate gradient: 15/1 to 10/1; then dichloromethane/methanol: 10/1). This gave 780 mg of the target compound (42% of theory).

Variant B:

650 mg (1.56 mmol; purity 77%) of 1-(2,3-difluorobenzyl)-5-fluoro-6-methyl-1H-pyrazolo[3,4-b]pyridine-3-carboxamide of the compound obtained in Example 5A were initially charged in 2.7 ml of THF, and 0.49 ml (6.0 mmol) of pyridine were added. With stirring, 0.85 ml (6.0 mmol) of trifluoroacetic anhydride was then slowly added dropwise, and the mixture was then stirred at RT for 3 h. Water was added, and the reaction solution was extracted three times with ethyl acetate. The organic phases were combined, washed once with saturated aqueous sodium bicarbonate solution, once with 1 N aqueous hydrochloric acid and once with saturated aqueous sodium chloride solution, then dried over sodium sulphate, concentrated and dried under high vacuum overnight. The crude product was purified by flash chromatography (mobile phase: cyclohexane/ethyl acetate gradient 15/1 to 10/1; then dichloromethane/methanol=10/1). This gave 180 mg of the target compound (37% of theory).

LC-MS (Method 1): $R_t$=1.19 min

MS (ESIpos): m/z=303 (M+H)$^+$ $^1$H NMR (400 MHz, DMSO-d$_6$): δ [ppm]=2.65 (d, 3H), 5.87 (s, 2H), 7.10-7.25 (m, 2H), 7.39-7.48 (m, 1H), 8.41 (d, 1H).

Example 5A 1-(2,3-Difluorobenzyl)-5-fluoro-6-methyl-1H-pyrazolo[3,4-b]pyridine-3-carboxamide

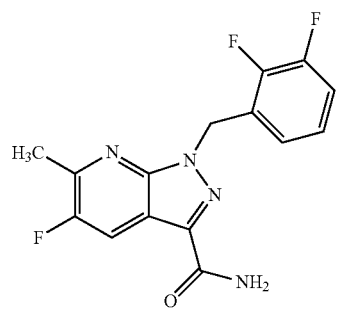 [SMILES: Cc1nc2c(cc1F)c(C(N)=O)nn2Cc1cccc(F)c1F]

The target compound was formed as a minor component during the preparation of starting material 4A. Flash chromatography gave 650 mg (26% of theory; purity 77%) of the target compound.

LC-MS (Method 1): $R_t$=0.98 min

MS (ESIpos): m/z=321 (M+H)$^+$

Example 6A 1-(2,3-Difluorobenzyl)-5-fluoro-6-methyl-1H-pyrazolo[3,4-b]pyridine-3-carboximidamide

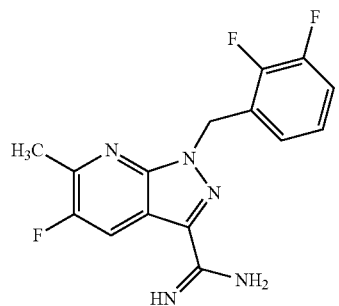 [SMILES: Cc1nc2c(cc1F)c(C(=N)N)nn2Cc1cccc(F)c1F]

960 mg (3.18 mmol) of 1-(2,3-difluorobenzyl)-5-fluoro-6-methyl-1H-pyrazolo[3,4-b]pyridine-3-carbonitrile from Example 4A were initially charged in 9.47 ml of methanol. 0.69 ml (3.18 mmol) of sodium methoxide in methanol was added, and the mixture was stirred at RT for 1 h. Another 10 ml of methanol were then added, and the reaction mixture was stirred at 60° C. for 1 h. 204 mg (3.81 mmol) of ammonium chloride and 0.71 ml (12.39 mmol) of acetic acid were added and the reaction mixture was stirred under reflux for 7 h. The solvent was concentrated and the residue was stirred with 38 ml of 1 N aqueous sodium hydroxide solution at room temperature for 1 h. The precipitate was then filtered off and washed with water. This gave 1.0 g of the target compound (90% of theory; purity 90%).

LC-MS (Method 1): $R_t$=0.68 min

MS (ESIpos): m/z=320 (M+H)$^+$ $^1$H NMR (400 MHz, DMSO-d$_6$): δ [ppm]=2.60 (d, 3H), 5.77 (s, 2H), 6.62 (br. s, 3H), 6.91-6.98 (m, 1H), 7.11-7.20 (m, 1H), 7.34-7.44 (m, 1H), 8.29 (d, 1H).

Example 7A 1-(2,3-Difluorobenzyl)-5-fluoro-6-methyl-1H-pyrazolo[3,4-b]pyridine-3-carboximidohydrazide

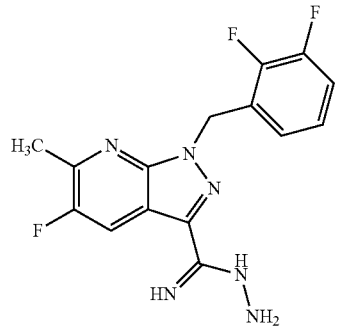 [SMILES: Cc1nc2c(cc1F)c(C(=N)NN)nn2Cc1cccc(F)c1F]

1.0 g (2.84 mmol; purity 90%) of 1-(2,3-difluorobenzyl)-5-fluoro-6-methyl-1H-pyrazolo[3,4-b]pyridine-3-carboximidamide from Example 6A were initially charged in 13.9 ml of ethanol, and 1.58 ml (11.38 mmol) of triethylamine and 0.19 ml (3.13 mmol) of hydrazine hydrate (80%) were added at 0° C. The mixture was stirred at RT for 4 h and then added to 28 ml of a 10% strength aqueous sodium chloride solution and extracted twice with ethyl acetate. The combined organic phases were washed with 10% strength aqueous sodium chloride solution, dried over sodium sulphate and concentrated on a rotary evaporator at RT. The residue was stirred with diethyl ether and filtered off, and the precipitate was dried under high vacuum. This gave 864 mg (89% of theory) of the title compound. The filtrate was concentrated and dried under high vacuum. This gave an additional 144 mg (10% of theory, purity 69%) of the title compound.

LC-MS (Method 3): $R_t$=2.36 min

MS (EIpos): m/z=335 [M+H]$^+$.

Example 8A

Methyl 2-{3-[1-(2,3-difluorobenzyl)-5-fluoro-6-methyl-1H-pyrazolo[3,4-b]pyridin-3-yl]-5-hydroxy-1,2,4-triazin-6-yl}-2-methylpropanoate

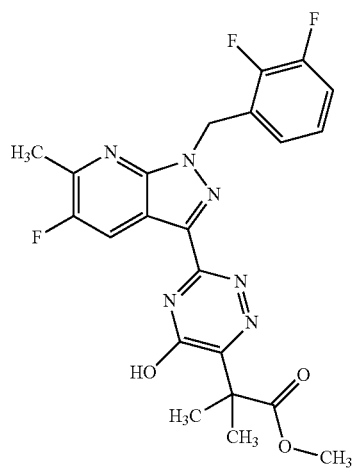 [SMILES: COC(=O)C(C)(C)c1nnc(-c2nn(Cc3cccc(F)c3F)c3nc(C)c(F)cc23)nc1O]

1.61 g (8.53 mmol) of dimethyl 2,2-dimethyl-3-oxobutanedioate (described in C. J. A. Daley et al. J. Am. Chem. Soc. 2002, 124(14), 3680-3691) were initially charged in 21 ml of ethanol and heated to reflux. A suspension of 0.95 g (2.84 mmol) of 1-(2,3-difluorobenzyl)-5-fluoro-6-methyl-1H-pyrazolo[3,4-b]pyridine-3-carboximidohydrazide from Example 7A in 21 ml of ethanol was added dropwise. The mixture was heated under reflux overnight. After cooling, a solid was filtered off with suction and washed with a little ethanol, and the filtrate was concentrated. Acetonitrile was added to the residue. This resulted in the precipitation of a solid. The latter was filtered off and dried. This gave 570 mg (42% of theory) of the title compound.

LC-MS (Method 1): $R_t$=1.14 min

MS (EIpos): m/z=473 [M+H]$^+$.

$^1$H NMR (400 MHz, DMSO-d$_6$): δ [ppm]=1.44 (s, 6H), 2.64 (d, 3H), 3.55 (s, 3H), 5.90 (s, 2H), 7.04-7.10 (m, 1H), 7.14-7.20 (m, 1H), 7.38-7.46 (m, 1H), 8.30 (d, 1H), 14.50 (br. s, 1H).

Example 9A

Methyl 2-{5-chloro-3-[1-(2,3-difluorobenzyl)-5-fluoro-6-methyl-1H-pyrazolo[3,4-b]pyridin-3-yl]-1,2,4-triazin-6-yl}-2-methylpropanoate

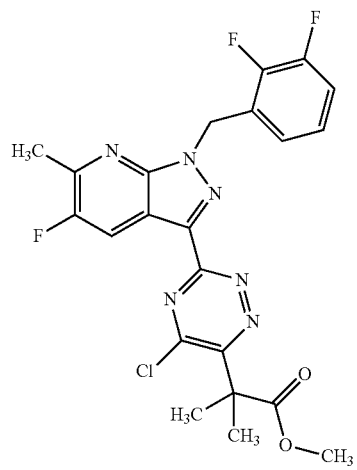 [SMILES: COC(=O)C(C)(C)c1nnc(-c2nn(Cc3cccc(F)c3F)c3nc(C)c(F)cc23)nc1Cl]

19.4 ml of phosphoryl chloride were added to 717 mg (1.52 mmol) of methyl 2-{3-[1-(2,3-difluorobenzyl)-5-fluoro-6-methyl-1H-pyrazolo[3,4-b]pyridin-3-yl]-5-hydroxy-1,2,4-triazin-6-yl}-2-methylpropanoate, the compound from Example 8A, and the mixture was stirred at RT for 5.5 h. The reaction mixture was used directly for the subsequent reaction.

LC-MS (Method 1): $R_t$=1.37 min

MS (EIpos): m/z=491 [M+H]$^+$.

Example 10A

3-Iodo-6-methyl-1H-pyrazolo[3,4-b]pyridine

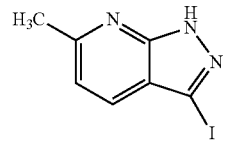

10 g (67.49 mmol) of 6-methyl-1H-pyrazolo[3,4-b]pyridine-3-amine were initially charged in 250 ml of THF, and the mixture was cooled to 0° C. 17.11 ml (134.98 mmol) of boron trifluoride/diethyl ether complex were then added slowly, and the reaction mixture was cooled to −10° C. A solution of 11.81 ml (87.74 mmol) of isopentyl nitrite in 50 ml of THF was then added slowly, and the mixture was stirred for a further 30 min. Cold diethyl ether (500 ml) was then added dropwise. The reaction mixture was allowed to warm to 10° C. and the resulting solid was filtered off with suction and washed with cold diethyl ether. A little at a time, the solid was added with foaming to a solution at 0° C. of 13.15 g (87.74 mmol) of sodium iodide in 300 ml of acetone, and the reaction mixture was stirred at RT for 30 min. The reaction mixture was poured into water and extracted three times with ethyl acetate. The organic phases were combined and the solid was filtered off with suction. The filtrate was dried over sodium sulphate, filtered and concentrated. Diethyl ether and a few drops of methanol were added to the residue. The solid was filtered off with suction, washed with diethyl ether and dried under high vacuum. This gave 11.67 g (67% of theory) of the title compound.

LC-MS (Method 1): $R_t$=0.78 min
MS (ESIpos): m/z=260 (M+H)$^+$

Example 11A 1-(2,3-Difluorobenzyl)-3-iodo-6-methyl-1H-pyrazolo[3,4-b]pyridine

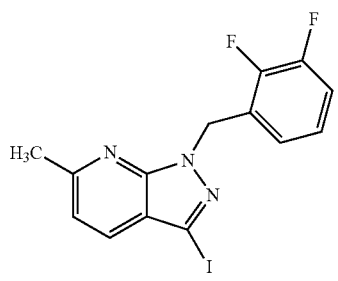 [SMILES: Cc1ccc2c(I)nn(Cc3cccc(F)c3F)c2n1]

1.76 g (6.78 mmol) of 3-iodo-6-methyl-1H-pyrazolo[3,4-b]pyridine from Example 10A were initially charged in 13.3 ml of DMF, and 3.31 g (10.17 mmol) of caesium carbonate and 1.68 g (8.14 mmol) of 1-(bromomethyl)-2,3-difluorobenzene were added. The mixture was stirred at RT for 7 h and then stored at 0° C. overnight. Water was then added to the reaction mixture. Ethyl acetate was added, the mixture was stirred briefly and the phases were separated. The organic phase was washed once with water and the aqueous phase was extracted with ethyl acetate. The combined organic phases were washed once with saturated aqueous sodium chloride solution, then dried over sodium sulphate and concentrated, and the residue was dried under high vacuum overnight. This gave 3.00 g (quantitative yield; purity about 87%) of the title compound.

LC-MS (Method 1): $R_t$=1.24 min
MS (ESIpos): m/z=386 (M+H)$^+$
$^1$H NMR (400 MHz, DMSO-d$_6$): δ [ppm]=2.65 (s, 3H), 5.73 (s, 2H), 7.02-6.95 (m, 1H), 7.13-7.20 (m, 1H), 7.22 (d, 1H), 7.35-7.44 (m, 1H), 7.84 (d, 1H).

Example 12A 1-(2,3-Difluorobenzyl)-6-methyl-1H-pyrazolo[3,4-b]pyridine-3-carbonitrile

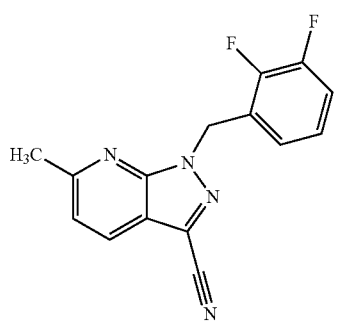 [SMILES: Cc1ccc2c(C#N)nn(Cc3cccc(F)c3F)c2n1]

3.00 g (6.78 mmol; purity about 87%) of 1-(2,3-difluorobenzyl)-3-iodo-6-methyl-1H-pyrazolo[3,4-b]pyridine (crude) from Example 11A and 0.768 g (8.58 mmol) of copper(I) cyanide were initially charged in 40 ml of abs. DMSO in a flask which had been dried by heating, and the mixture was stirred at 150° C. for 1.5 h. A mixture of saturated aqueous ammonium chloride solution, concentrated aqueous ammonia solution (3/1) and ethyl acetate was added to the cooled reaction solution, and the mixture was stirred at RT for 30 min and filtered off with suction through Celite®. The filter residue was washed with ethyl acetate and the organic phase was separated off and washed four times with a mixture of saturated aqueous ammonium chloride solution and concentrated aqueous ammonia solution (3/1). The organic phase was washed once with saturated aqueous sodium chloride solution, dried over sodium sulphate, concentrated and dried under high vacuum overnight. The title compound 2.55 g (quantitative, purity 84%) was used without further purification for the next step.

LC-MS (Method 1): $R_t$=1.16 min
MS (ESIpos): m/z=285 (M+H)$^+$
$^1$H NMR (400 MHz, DMSO-d$_6$): δ [ppm]=2.69 (s, 3H), 5.87 (s, 2H), 7.14-7.09 (m, 1H), 7.16-7.23 (m, 1H), 7.39-7.47 (m, 1H), 7.43 (d, 1H), 8.37 (d, 1H).

Example 13A 1-(2,3-Difluorobenzyl)-6-methyl-1H-pyrazolo[3,4-b]pyridine-3-carboximidamide acetate

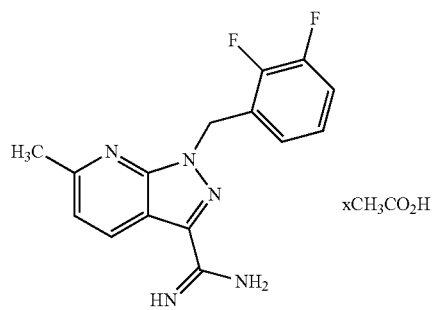 [SMILES: Cc1ccc2c(C(=N)N)nn(Cc3cccc(F)c3F)c2n1]

2.22 g (6.55 mmol; purity 84%) of 1-(2,3-difluorobenzyl)-6-methyl-1H-pyrazolo[3,4-b]pyridine-3-carbonitrile from Example 12A and 0.354 g (6.55 mmol) of sodium methoxide were initially charged in 20 ml of methanol, and the mixture was stirred at RT for 4.5 h. 0.421 g (7.86 mmol) of ammonium chloride and 1.46 ml (25.55 mmol) of acetic acid were added and the reaction mixture was stirred under reflux for 6 h. The reaction mixture was cooled, the solvent was concentrated under reduced pressure, 1 N aqueous sodium hydroxide solution was added to the residue (up to pH 9) and ethyl acetate was added. The mixture was stirred at 0° C. for 30 min. The precipitate was then filtered off, washed with ethyl acetate and dried under high vacuum overnight. This gave 1.14 g of the target compound (48% of theory).

LC-MS (Method 1): $R_t$=0.62 min
MS (ESIpos): m/z=302 (M+H)$^+$
$^1$H NMR (400 MHz, DMSO-d$_6$): δ [ppm]=1.82-1.86 (m, 3H), 2.63 (s, 3H), 5.78 (s, 2H), 6.90-6.96 (m, 1H), 7.11-7.18 (m, 1H), 7.25 (d, 1H), 7.34-7.43 (m, 1H), 8.50-7.54 (m, 2H).

Example 14A 1-(2,3-Difluorobenzyl)-6-methyl-1H-pyrazolo[3,4-b]pyridine-3-carboximidohydrazide

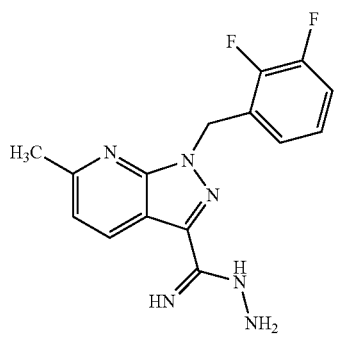 [SMILES: Cc1ccc2c(C(=N)NN)nn(Cc3cccc(F)c3F)c2n1]

1.14 g (3.16 mmol) of 1-(2,3-difluorobenzyl)-6-methyl-1H-pyrazolo[3,4-b]pyridine-3-carboximidamide acetate from Example 13A were initially charged in 15 ml of ethanol, and 1.76 ml (12.62 mmol) of triethylamine and 0.192 ml (3.16 mmol) of hydrazine hydrate (80%) were added at 0° C. The mixture was stirred initially at 0° C. for 10 min and then overnight at RT. The reaction mixture was added to 70 ml of a 10% strength aqueous sodium chloride solution and extracted twice with ethyl acetate. The combined organic phases were washed once with 10% strength aqueous sodium chloride solution, dried over sodium sulphate and concentrated on a rotary evaporator at RT. The residue was dried under high vacuum. This gave 0.96 g (94% of theory) of the title compound.

LC-MS (Method 1): $R_t$=0.62 min

MS (EIpos): m/z=317 [M+H]$^+$.

$^1$H NMR (400 MHz, DMSO-d$_6$): δ [ppm]=2.60 (s, 3H), 5.36 (br.s., 2H), 5.49 (br.s., 2H), 5.72 (s, 2H), 6.84-6.90 (m, 1H), 7.10-7.18 (m, 1H), 7.16 (d, 1H), 7.32-7.41 (m, 1H), 8.38 (d, 1H).

Example 15A

Methyl 2-{3-[1-(2,3-difluorobenzyl)-6-methyl-1H-pyrazolo[3,4-b]pyridin-3-yl]-5-hydroxy-1,2,4-triazin-6-yl}-2-methylpropanoate

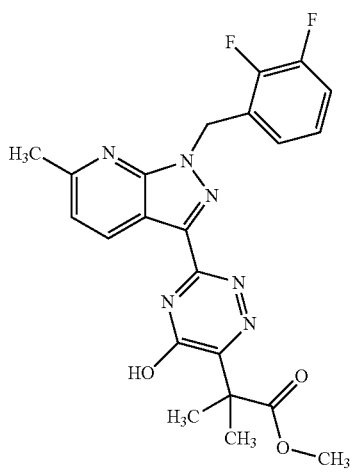 [SMILES: COC(=O)C(C)(C)c1nnc(-c2nn(Cc3cccc(F)c3F)c3nc(C)ccc23)nc1O]

0.860 g (4.57 mmol) of dimethyl 2,2-dimethyl-3-oxobutanedioate (described in C. J. A. Daley et al. J. Am. Chem. Soc. 2002, 124(14), 3680-3691) was initially charged in 10 ml of ethanol and heated to reflux. A suspension of 0.95 g (2.84 mmol) of 1-(2,3-difluorobenzyl)-6-methyl-1H-pyrazolo[3,4-b]pyridine-3-carboximidohydrazide from Example 14A in 25 ml of ethanol was added dropwise. The mixture was stirred under reflux for 12 h. After cooling, a precipitate was filtered off with suction and washed with a little ethanol, and the filtrate was concentrated and dried under high vacuum. This gave 1.36 g (68% of theory; purity 69%) of the title compound (crude) which was used for the subsequent step without further purification.

LC-MS (Method 1): $R_t$=1.09 min

MS (EIpos): m/z=455 [M+H]$^+$.

Example 16A

Methyl 2-{5-chloro-3-[1-(2,3-difluorobenzyl)-6-methyl-1H-pyrazolo[3,4-b]pyridin-3-yl]-1,2,4-triazin-6-yl}-2-methylpropanoate

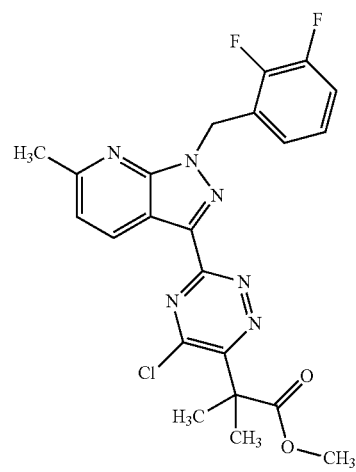 [SMILES: COC(=O)C(C)(C)c1nnc(-c2nn(Cc3cccc(F)c3F)c3nc(C)ccc23)nc1Cl]

9.0 ml of phosphoryl chloride were added to 1.36 g (2.99 mmol; purity 69%) of methyl 2-{3-[1-(2,3-difluorobenzyl)-6-methyl-1H-pyrazolo[3,4-b]pyridin-3-yl]-5-hydroxy-1,2,4-triazin-6-yl}-2-methylpropanoate from Example 15A, and the mixture was stirred at RT for 60 h. The reaction mixture was used without any further purification for the subsequent reaction.

LC-MS (Method 1): $R_t$=1.32 min

MS (EIpos): m/z=473 [M+H]$^+$.

Example 17A

5-Fluoro-3-iodo-1-(4-methoxybenzyl)-6-methyl-1H-pyrazolo[3,4-b]pyridine

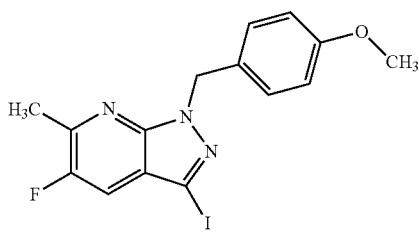

Under argon, 14.90 g (53.78 mmol) of 5-fluoro-3-iodo-6-methyl-1H-pyrazolo[3,4-b]pyridine from Example 2A were initially charged in 150 ml of abs. DMF, and 21.03 g (64.54 mmol) of caesium carbonate and 8.42 g (53.78 mmol) of 1-(chloromethyl)-4-methoxybenzene, dissolved in 50 ml of DMF, were then added. The mixture was stirred at RT overnight. The reaction mixture was then added to 1000 ml of water and extracted three times with ethyl acetate. The collected organic phases were dried over sodium sulphate, filtered and concentrated. The residue was purified by SFC chromatography [column: THAR SFC-Super Chrom Prep 200, 5 μm, 150×30 mm; mobile phase: 95% carbon dioxide+5% methanol; pressure: 150 bar; flow rate: 150 ml/min; temperature: 38° C.; wavelength: 210 nm]. This gave 12.95 g (61% of theory) of the title compound.

LC-MS (Method 5): $R_t$=2.77 min
MS (ESIpos): m/z=398 (M+H)$^+$
$^1$H NMR (400 MHz, DMSO-d$_6$): δ [ppm]=2.61 (d, 3H), 3.71 (s, 3H), 5.55 (s, 2H), 6.88 (d, 2H), 7.21 (d, 2H), 7.78 (d, 1H).

Example 18A

5-Fluoro-1-(4-methoxybenzyl)-6-methyl-1H-pyrazolo[3,4-b]pyridine-3-carbonitrile

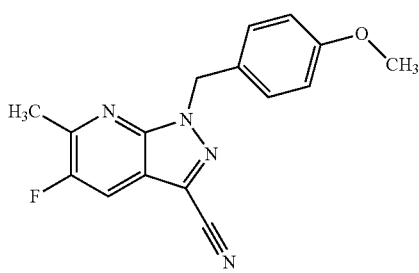

A mixture of 11.80 g (29.71 mmol) of 5-fluoro-3-iodo-1-(4-methoxybenzyl)-6-methyl-1H-pyrazolo[3,4-b]pyridine from Example 17A and 2.93 g (32.72 mmol) of copper(I) cyanide was initially charged in 94 ml of abs. DMSO in a flask which had been dried by heating, and the mixture was stirred at 150° C. for 2 h. The cooled reaction solution was filtered through Celite and the filter residue was washed with 1.2 l of THF/ethyl acetate (1/1). The filtrate was washed with 940 ml of a 25% strength aqueous ammonia solution, 830 ml of semiconcentrated aqueous ammonium chloride solution and 410 ml of saturated aqueous sodium chloride solution. The organic phase was dried over sodium sulphate, filtered and then concentrated under reduced pressure. The crude product was purified by silica gel chromatography (mobile phase: petroleum ether/ethyl acetate: 3/1; then dichloromethane/methanol gradient). This gave 7.50 g (85% of theory) of the target compound.

LC-MS (Method 1): $R_t$=1.18 min
MS (ESIpos): m/z=297 (M+H)$^+$
$^1$H NMR (400 MHz, DMSO-d$_6$): δ [ppm]=2.65 (d, 3H), 3.71 (s, 3H), 5.69 (s, 2H), 6.89 (d, 2H), 7.29 (d, 2H), 8.37 (d, 1H).

Example 19A

5-Fluoro-1-(4-methoxybenzyl)-6-methyl-1H-pyrazolo[3,4-b]pyridine-3-carboximidamide

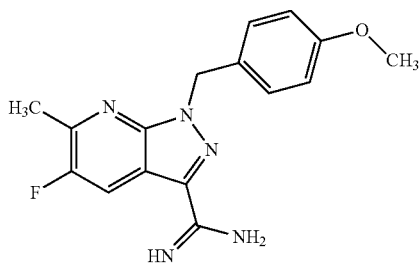

7.80 g (26.32 mmol) of 5-fluoro-1-(4-methoxybenzyl)-6-methyl-1H-pyrazolo[3,4-b]pyridine-3-carbonitrile from Example 18A were initially charged in 120 ml of methanol/THF/dichloromethane (1/1/1). 1.42 g (26.32 mmol) of sodium methoxide in 10 ml of methanol were added, and the mixture was stirred at RT for 2 h. 1.55 g (28.98 mmol) of ammonium chloride and 5.88 ml (102.74 mmol) of acetic acid were added and the reaction mixture was stirred under reflux for 2 h. Another 50 ml of methanol were added to the reaction mixture. The dichloromethane was distilled off and the mixture was stirred under reflux for 1 h. The solvent mixture was concentrated and the residue was stirred with about 160 ml of 1 N aqueous sodium hydroxide solution at room temperature for 1 h. The residue was then filtered off and washed with water. This gave 8.15 g of the target compound (99% of theory).

LC-MS (Method 1): $R_t$=0.68 min
MS (ESIpos): m/z=314 (M+H)$^+$
$^1$H NMR (400 MHz, DMSO-d$_6$): δ [ppm]=2.60 (d, 3H), 3.70 (s, 3H), 5.59 (s, 2H), 6.21 (br. s, 2H), 6.87 (d, 2H), 7.21 (d, 2H), 8.26 (d, 1H).

Example 20A

5-Fluoro-1-(4-methoxybenzyl)-6-methyl-1H-pyrazolo[3,4-b]pyridine-3-carboximidohydrazide

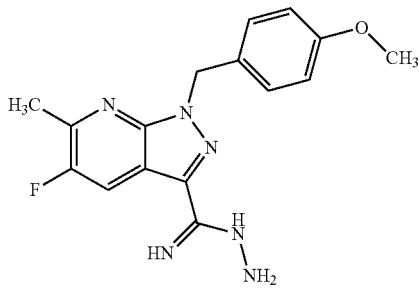

7.0 g (21.22 mmol) of 5-fluoro-1-(4-methoxybenzyl)-6-methyl-1H-pyrazolo[3,4-b]pyridine-3-carboximidamide from Example 19A were initially charged in 94 ml of ethanol, and 11.83 ml (84.88 mmol) of triethylamine and 1.29 ml (21.22 mmol) of hydrazine hydrate (80%) were added at 0° C. The mixture was stirred at RT overnight and then added to 260 ml of a 10% strength aqueous sodium chloride solution and extracted twice with ethyl acetate. The combined organic phases were washed with 10% strength aqueous sodium chloride solution, dried over sodium sulphate and concentrated on a rotary evaporator at RT. The residue was dried under high vacuum. This gave 7.33 g (96% of theory; purity about 91%) of the title compound.

LC-MS (Method 3): $R_t$=2.25 min
MS (EIpos): m/z=329 [M+H]$^+$.

Example 21A

Methyl 2-{3-[5-fluoro-1-(4-methoxybenzyl)-6-methyl-1H-pyrazolo[3,4-b]pyridin-3-yl]-5-hydroxy-1,2,4-triazin-6-yl}-2-methylpropanoate

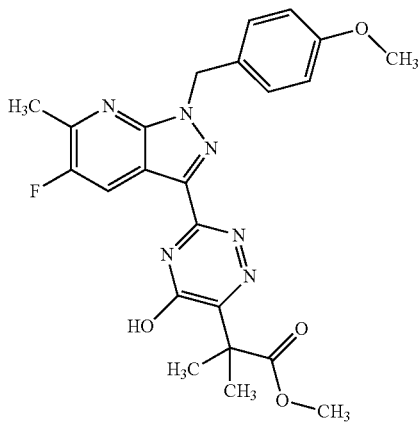

11.47 g (60.93 mmol) of dimethyl 2,2-dimethyl-3-oxobutanedioate (described in C. J. A. Daley et al. J. Am. Chem. Soc. 2002, 124(14), 3680-3691) were initially charged in 146 ml of ethanol and heated to reflux. A suspension of 7.33 g (20.31 mmol; purity about 91%) of 5-fluoro-1-(4-methoxybenzyl)-6-methyl-1H-pyrazolo[3,4-b]pyridine-3-carboximidohydrazide from Example 20A in 146 ml of ethanol was added dropwise. The mixture was heated under reflux overnight. After cooling, a solid was filtered off and washed with ethanol, and the filtrate was concentrated. About 30 ml of acetonitrile were added to the residue, and the mixture was stirred at RT for 1 h. The solid was filtered off and dried. This gave 5.58 g (50% of theory; purity about 85%) of the title compound.

LC-MS (Method 1): $R_t$=1.11 min
MS (EIpos): m/z=467 [M+H]$^+$.

$^1$H NMR (400 MHz, DMSO-d$_6$): δ [ppm]=1.44 (s, 6H), 2.65 (d, 3H), 3.55 (s, 3H), 3.71 (s, 3H), 5.73 (s, 2H), 6.89 (d, 2H), 7.30 (d, 2H), 8.28 (d, 1H), 14.52 (br. s, 1H).

Example 22A

Methyl 2-{5-chloro-3-[5-fluoro-1-(4-methoxybenzyl)-6-methyl-1H-pyrazolo[3,4-b]pyridin-3-yl]-1,2,4-triazin-6-yl}-2-methylpropanoate

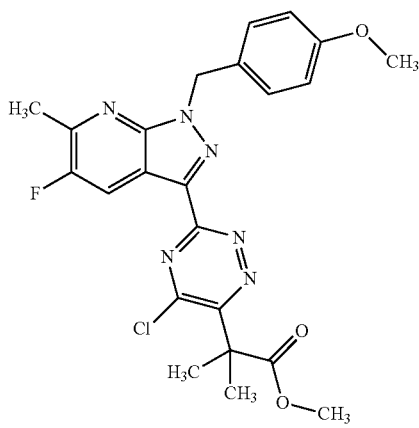

53.6 ml of phosphoryl chloride were added to 5.98 g (10.90 mmol; purity about 85%) of methyl 2-{3-[5-fluoro-1-(4-methoxybenzyl)-6-methyl-1H-pyrazolo[3,4-b]pyridin-3-yl]-5-hydroxy-1,2,4-triazin-6-yl}-2-methylpropanoate, the compound from Example 21A, and the mixture was stirred at RT overnight. Another 20 ml of phosphoryl chloride were then added, and the mixture was stirred at RT for 0.5 h. The reaction mixture was used directly for the subsequent reaction.

LC-MS (Method 1): $R_t$=1.35 min
MS (EIpos): m/z=485 [M+H]$^+$.

Example 23A

3-[5-Fluoro-1-(4-methoxybenzyl)-6-methyl-1H-pyrazolo[3,4-b]pyridin-3-yl]-7,7-dimethyl-5,7-dihydro-6H-pyrrolo[2,3-e][1,2,4]triazin-6-one

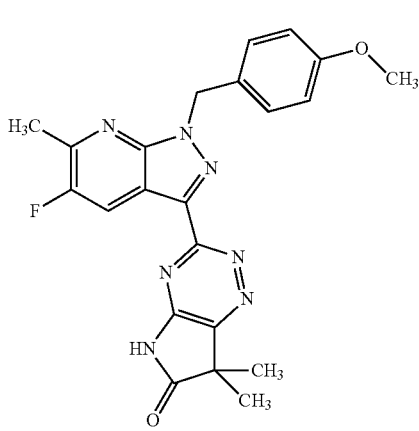

The reaction solution of methyl 2-{5-chloro-3-[5-fluoro-1-(4-methoxybenzyl)-6-methyl-1H-pyrazolo[3,4-b]pyridin-3-yl]-1,2,4-triazin-6-yl}-2-methylpropanoate from Example 22A was diluted with 500 ml of dry acetonitrile and then slowly added dropwise to 780 ml of a 33% strength aqueous ammonia solution (strongly exothermic). The reaction mixture was stirred at room temperature overnight. The organic phase of the reaction mixture was removed and the aqueous phase was extracted twice with dichloromethane. The organic phase was washed once with saturated aqueous sodium chloride solution and then dried over sodium sulphate, filtered and concentrated. This gave 5.27 g (89% of theory; purity 80%) of the target compound.

50 mg of this were purified by preparative HPLC (RP18 column, mobile phase: acetonitrile/water gradient with addition of 0.1% TFA). The product fractions obtained were taken up in dichloromethane and washed twice with saturated aqueous sodium bicarbonate solution. The combined organic phases were dried over sodium sulphate, filtered and concentrated. 35 mg of the target compound were obtained.

LC-MS (Method 1): $R_t$=1.09 min

MS (ESIpos): m/z=434 (M+H)$^+$ $^1$H NMR (500 MHz, DMSO-d$_6$): δ [ppm]=1.44 (s, 6H); 2.65 (d, 3H), 3.70 (s, 3H), 5.70 (s, 2H), 6.89 (d, 2H), 7.28 (d, 2H), 8.42 (d, 1H), 12.14 (br.s, 1H).

Example 24A 3-(5-Fluoro-6-methyl-1H-pyrazolo[3,4-b]pyridin-3-yl)-7,7-dimethyl-5,7-dihydro-6H-pyrrolo[2,3-e][1,2,4]triazin-6-one

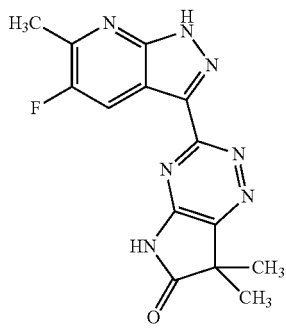

1.0 g (1.85 mmol, purity 80%) of 3-[5-fluoro-1-(4-methoxybenzyl)-6-methyl-1H-pyrazolo[3,4-b]pyridin-3-yl]-7,7-dimethyl-5,7-dihydro-6H-pyrrolo[2,3-e][1,2,4]triazin-6-one from Example 23A were initially charged in 40.5 ml of acetonitrile/water (2/1), 4.05 g (7.38 mmol) of ammoniumcerium(IV) nitrate were added and the mixture was stirred at room temperature for 3 h. 50 ml of water were added to the reaction mixture and the mixture was stirred at room temperature for 2 h and then filtered off, washed with water and dried under high vacuum. This gave 540 mg of the target compound (91% of theory).

LC-MS (Method 3): $R_t$=1.56 min

MS (ESIpos): m/z=314 (M+H)$^+$ $^1$H NMR (500 MHz, DMSO-d$_6$): δ [ppm]=1.46 (s, 6H); 2.61 (d, 3H), 8.40 (d, 1H), 12.15 (br.s, 1H), 14.24 (br. s, 1H).

Example 25A

3-Iodo-6-methyl-1-{[2-(trimethylsilyl)ethoxy]methyl}-1H-pyrazolo[3,4-b]pyridine

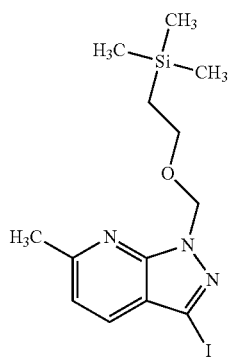 [SMILES: Cc1ccc2c(I)nn(COCC[Si](C)(C)C)c2n1]

19.8 g (76.35 mmol) of 3-iodo-6-methyl-1H-pyrazolo[3,4-b]pyridine from Example 10A were initially charged in 190 ml of dichloromethane, 246 mg (0.76 mmol) of tetrabutylammonium bromide and 96 ml of 50% strength aqueous potassium hydroxide solution were added at 0° C. and the mixture was stirred vigorously. 16.2 ml (91.62 mmol) of [2-(chloromethoxy)ethyl](trimethyl)silane were then added dropwise and the reaction mixture was stirred at 0° C. for 1 h and then at RT for 1 h. 2.7 ml (15.27 mmol) of [2-(chloromethoxy)ethyl](trimethyl)silane were then added dropwise at RT and the mixture was stirred at RT for 1 h. The reaction mixture was stored at −20° C. overnight. Another 4.04 ml (22.90 mmol) of [2-(chloromethoxy)ethyl](trimethyl)silane were then added dropwise at 0° C., and the reaction mixture was stirred at 0° C. for 1 h and at RT for 1 h. The organic phase was separated off and the aqueous phase was extracted twice with dichloromethane. The combined organic phases were washed twice with saturated aqueous sodium chloride solution and then dried over sodium sulphate and concentrated under reduced pressure. The residue was purified by flash chromatography (mobile phase: cyclohexane/dichloromethane gradient, then dichloromethane/ethyl acetate gradient). This gave 18.14 g (61% of theory) of the title compound.

LC-MS (Method 1): $R_t$=1.37 min

MS (ESIpos): m/z=390 (M+H)$^+$ $^1$H NMR (400 MHz, DMSO-d$_6$): δ [ppm]=−0.11 (s, 9H), 0.79-0.85 (m, 2H), 2.63 (s, 3H), 3.55-3.62 (m, 2H), 5.71 (s, 2H), 7.23 (d, 1H), 7.84 (d, 1H).

Example 26A

6-Methyl-1-{[2-(trimethylsilyl)ethoxy]methyl}-1H-pyrazolo[3,4-b]pyridine-3-carbonitrile

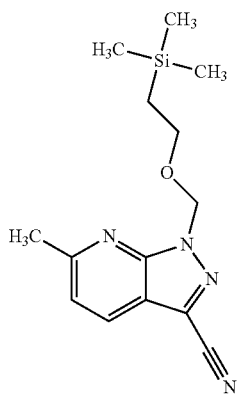 [SMILES: Cc1ccc2c(C#N)nn(COCC[Si](C)(C)C)c2n1]

A mixture of 1.00 g (2.57 mmol) of 3-iodo-6-methyl-1-{[2-(trimethylsilyl)ethoxy]methyl}-1H-pyrazolo[3,4-b]pyridine from Example 25A and 0.253 g (2.83 mmol) of copper(I) cyanide were initially charged in 10 ml of abs. dimethyl sulphoxide, and the mixture was stirred at 150° C. for 3 h. A mixture of saturated aqueous ammonium chloride solution, concentrated aqueous ammonia solution (3/1) and ethyl acetate was added to the cooled reaction solution, and the mixture was stirred at RT for 30 min and filtered off through Celite®. The filter residue was washed with ethyl acetate. The organic phase was separated off and washed three times with a mixture of saturated aqueous ammonium chloride solution and concentrated aqueous ammonia solution (3/1) until the aqueous phase was colourless. The organic phase was washed once with saturated aqueous sodium chloride solution and then dried over sodium sulphate, concentrated and dried under high vacuum overnight. The title compound 0.74 g (76% of theory; purity 76%) was used without further purification for the next step.

LC-MS (Method 1): $R_t$=1.29 min

MS (ESIpos): m/z=289 (M+H)$^+$

Example 27A

6-Methyl-1-{[2-(trimethylsilyl)ethoxy]methyl}-1H-pyrazolo[3,4-b]pyridine-3-carboximidamide acetate

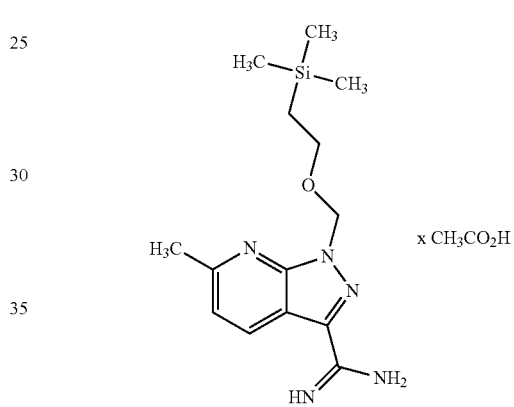

12.33 g (42.75 mmol; purity 76%) of 6-methyl-1-{[2-(trimethylsilyl)ethoxy]methyl}-1H-pyrazolo[3,4-b]pyridine-3-carbonitrile from Example 26A and 2.31 g (42.75 mmol) of sodium methoxide were initially charged in 200 ml of methanol, and the mixture was stirred at RT for 3 h. 2.74 g (51.30 mmol) of ammonium chloride and 9.5 ml (166.72 mmol) of acetic acid were added, and the mixture was stirred under reflux for 8 h. The reaction mixture was cooled, the solvent was concentrated under reduced pressure, 1 N aqueous sodium hydroxide solution was added to the residue (up to pH 9) and ethyl acetate was added. The mixture was stirred at RT for 30 min. The precipitate was then filtered off, washed with ethyl acetate and dried under high vacuum overnight. This gave 9.01 g of the target compound (48% of theory).

LC-MS (Method 1): $R_t$=0.74 min

MS (ESIpos): m/z=306 (M+H)$^+$ $^1$H NMR (400 MHz, DMSO-d$_6$): δ [ppm]=−0.10 (s, 9H), 0.81-0.88 (m, 2H), 1.84 (s, 3H), 2.64 (s, 3H), 3.58-3.67 (m, 2H), 5.79 (s, 2H), 7.29 (d, 1H), 8.49 (d, 1H), 8.87 (br.s., 3H).

Example 28A

6-Methyl-1-{[2-(trimethylsilyl)ethoxy]methyl}-1H-pyrazolo[3,4-b]pyridine-3-carboximidohydrazide

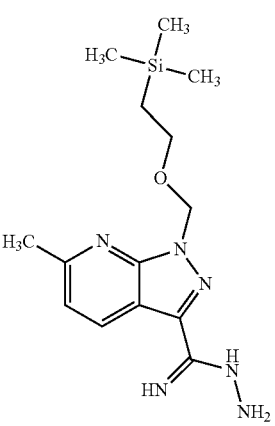 [SMILES: Cc1ccc2c(C(=N)NN)nn(COCC[Si](C)(C)C)c2n1]

9.33 g (25.52 mmol) of 6-methyl-1-{[2-(trimethylsilyl)ethoxy]methyl}-1H-pyrazolo[3,4-b]pyridine-3-carboximidamide acetate from Example 27A were initially charged in 120 ml of ethanol, and 14.3 ml (102.08 mmol) of triethylamine and 1.55 ml (25.52 mmol) of hydrazine hydrate (80%) were added at 0° C. The reaction mixture was stirred at 0° C. for 10 min and then overnight at RT. The reaction mixture was added to 550 ml of a 10% strength aqueous sodium chloride solution and extracted twice with ethyl acetate. The combined organic phases were washed once with 10% strength aqueous sodium chloride solution, dried over sodium sulphate and concentrated on a rotary evaporator at RT. The residue was dried under high vacuum. This gave 8.41 g (97% of theory; purity 94%) of the title compound.

LC-MS (Method 1): $R_t$=0.75 min
MS (ESIpos): m/z=321 (M+H)$^+$

Example 29A

Methyl 2-[5-hydroxy-3-(6-methyl-1-{[2-(trimethylsilyl)ethoxy]methyl}-1H-pyrazolo[3,4-b]pyridin-3-yl)-1,2,4-triazin-6-yl]-2-methylpropanoate

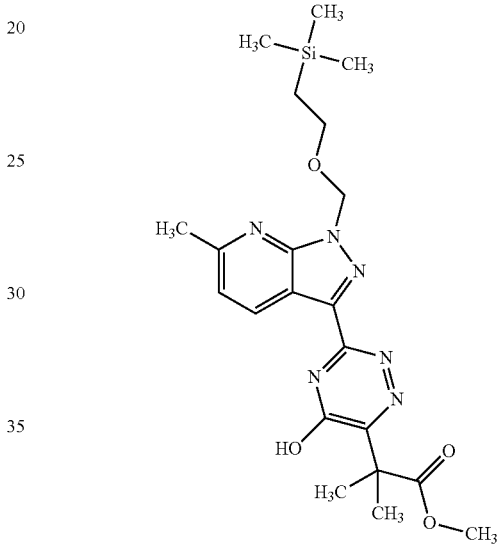

6.54 g (34.73 mmol) of dimethyl 2,2-dimethyl-3-oxobutanedioate (described in C. J. A. Daley et al. J. Am. Chem. Soc. 2002, 124(14), 3680-3691) were initially charged in 230 ml of ethanol and heated to reflux. 7.42 g (23.15 mmol) of 6-methyl-1-{[2-(trimethylsilyl)ethoxy]methyl}-1H-pyrazolo[3,4-b]pyridine-3-carboximidohydrazide from Example 28A were then added a little at a time. The reaction mixture was stirred under reflux overnight. After cooling, a precipitate was filtered off and washed with a little ethanol. The filtrate was concentrated and dried under high vacuum. This gave the title compound (crude) which was used in the next step without further purification.

LC-MS (Method 1): $R_t$=1.24 min
MS (ESIpos): m/z=459 (M+H)$^+$

Example 30A

Methyl 2-[5-chloro-3-(6-methyl-1-{[2-(trimethylsilyl)ethoxy]methyl}-1H-pyrazolo[3,4-b]pyridin-3-yl)-1,2,4-triazin-6-yl]-2-methylpropanoate

Example 31A 7,7-Dimethyl-3-(6-methyl-1-{[2-(trimethylsilyl)ethoxy]methyl}-1H-pyrazolo[3,4-b]pyridin-3-yl)-5,7-dihydro-6H-pyrrolo[2,3-e][1,2,4]triazin-6-one

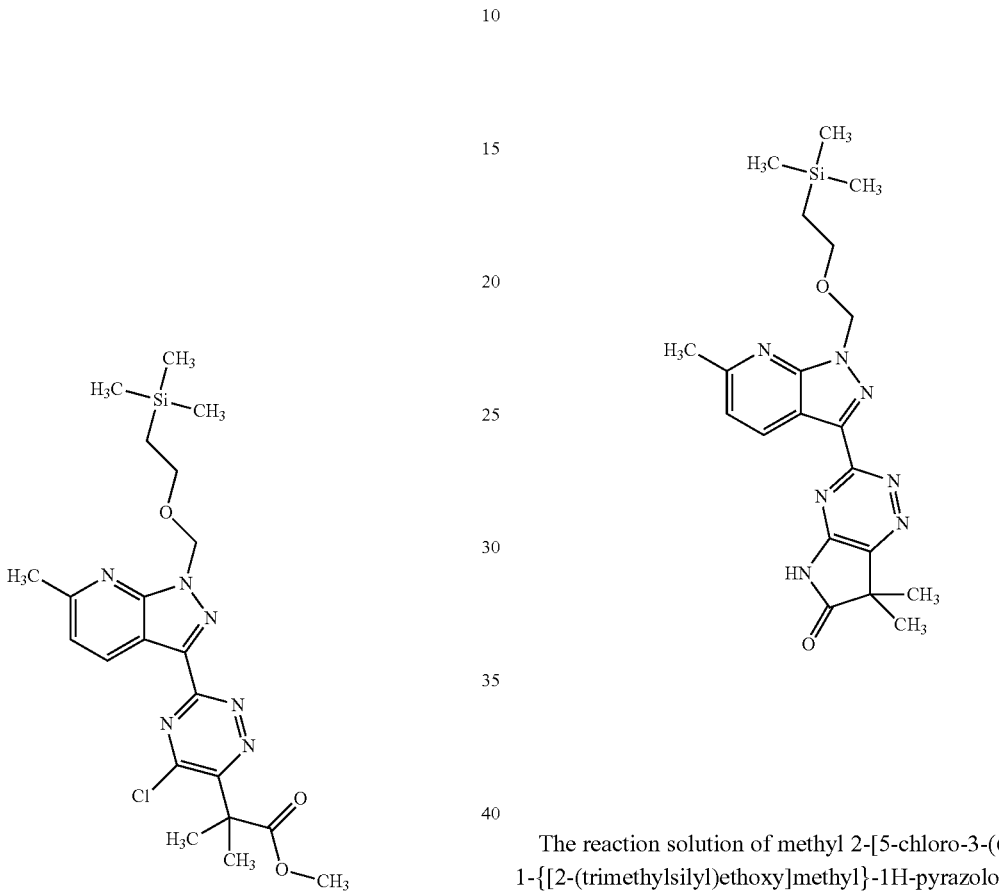

22 ml of tetrahydrothiophene 1,1-dioxide (sulpholane) and 11 ml of phosphorus oxytrichloride were added to 10.62 g (23.15 mmol) of methyl 2-[5-hydroxy-3-(6-methyl-1-{[2-(trimethylsilyl)ethoxy]methyl}-1H-pyrazolo[3,4-b]pyridin-3-yl)-1,2,4-triazin-6-yl]-2-methylpropanoate from Example 29A. The reaction mixture was kept at RT for 60 h and then used directly for the subsequent reaction.

LC-MS (Method 1): $R_t$=1.43 min
MS (EIpos): m/z=477 [M+H]$^+$.

The reaction solution of methyl 2-[5-chloro-3-(6-methyl-1-{[2-(trimethylsilyl)ethoxy]methyl}-1H-pyrazolo[3,4-b]pyridin-3-yl)-1,2,4-triazin-6-yl]-2-methylpropanoate from Example 30A was diluted with 78 ml of dry acetonitrile and then slowly added dropwise to a 33% strength aqueous ammonia solution (245 ml) cooled to 0° C., with the internal temperature being kept between 0-12° C. The mixture was then stirred at room temperature overnight. The two-phase reaction mixture was freed from the solvent on a rotary evaporator. The mixture was then extracted three times with ethyl acetate. The combined organic phases were concentrated, 800 ml of diethyl ether were added to the residue and the mixture was washed three times with water (200 ml, 400 ml, 200 ml) and once with aqueous sodium chloride solution, concentrated and dried under high vacuum. Dichloromethane was added to the residue and the mixture was filtered. The filtrate was applied to a silica gel column and purified by silica gel chromatography (mobile phase: dichloromethane/ethyl acetate gradient). This gave 4.05 g of the target compound (36% of theory; purity 88%).

LC-MS (Method 1): $R_t$=1.15 min
MS (EIpos): m/z=426 [M+H]$^+$.

Example 32A 7,7-Dimethyl-3-(6-methyl-1H-pyrazolo[3,4-b]pyridin-3-yl)-5,7-dihydro-6H-pyrrolo[2,3-e][1,2,4]triazin-6-one

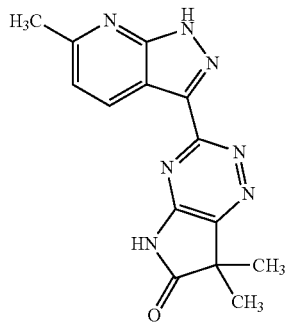

3.2 g (6.62 mmol; purity 88%) of 7,7-dimethyl-3-(6-methyl-1-{[2-(trimethylsilyl)ethoxy]methyl}-1H-pyrazolo[3,4-b]pyridin-3-yl)-5,7-dihydro-6H-pyrrolo[2,3-e][1,2,4]triazin-6-one from Example 31A were initially charged in 14 ml of dichloromethane and 14 ml of trifluoroacetic acid, and the mixture was stirred at RT for 30 min. The reaction mixture was concentrated under reduced pressure at 30° C. and the residue was dried under high vacuum. 33 ml of THF and 36.4 ml of a 2 N aqueous lithium hydroxide solution were then added, and the mixture was stirred at RT overnight. The reaction mixture was concentrated under reduced pressure at 50° C., 50 ml of water were added and the mixture was reconcentrated. The residue was dissolved in 70 ml of water and extracted three times with dichloromethane. The aqueous phase was acidified to pH 6 with concentrated aqueous hydrochloric acid and saturated with sodium chloride. The mixture was extracted five times with 2-methyltetrahydrofuran and the combined organic phases were concentrated on a rotary evaporator. The residue was extracted with two portions (100 ml and 50 ml) of methyl tert-butyl ether and filtered off. The filter residue was dried under high vacuum. This gave 1.20 g (55% of theory; purity about 90%) of the title compound.

LC-MS (Method 1): $R_t$=0.67 min

MS (ESIpos): m/z=296 (M+H)$^+$ $^1$H NMR (500 MHz, DMSO-d$_6$): δ [ppm]=1.46 (s, 6H); 2.63 (s, 3H), 7.27 (d, 1H), 8.68 (d, 1H), 12.17 (br.s, 1H), 14.05 (br. s, 1H).

Example 33A

Ethyl 1-formylcyclopropanecarboxylate

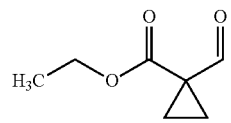

In a three-necked flask fitted with thermometer, dropping funnel and gas exhaust, 7.39 g (58.19 mmol) of oxalyl chloride were initially charged in 116 ml of abs. dichloromethane at −78° C. 9.08 g (116.38 mmol) of dimethyl sulphoxide, dissolved in 8 ml of abs. dichloromethane, were then slowly added dropwise (careful: intensive evolution of gas), with the internal temperature being kept between −70° C. and −78° C. The reaction mixture was stirred at −78° C. for another 5 min 7.63 g (52.90 mmol) of ethyl 1-(hydroxymethyl)cyclopropanecarboxylate (described in M. H. Parker et al. U.S. Pat. Appl. Publ., 20120053146), dissolved in 196 ml of abs. dichloromethane, were then slowly added dropwise, with the internal temperature being kept between −70° C. and −78° C. The reaction mixture was stirred at −78° C. for another 10 min 26.72 g (264.51 mmol) of triethylamine were then slowly added dropwise, with the internal temperature being kept between −70° C. and −78° C. The reaction mixture was stirred at −78° C. for another 10 min and then warmed to RT over 2 h. The mixture was diluted with 700 ml of methyl tert-butyl ether, the precipitate was filtered off and the filtrate was concentrated at 30° C. and 100 mbar. The residue was purified by flash chromatography (mobile phase: dichloromethane). This gave 7.30 g (97% of theory, purity about 95% according to NMR) of the title compound.

$^1$H NMR (500 MHz, CDCl$_3$): δ [ppm]=1.32 (t, 3H), 1.58-1.63 (m, 2H), 1.65-1.70 (m, 2H), 4.28 (q, 2H), 10.41 (s, 1H).

Example 34A

Ethyl 1-[cyano(hydroxy)methyl]cyclopropanecarboxylate

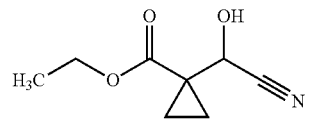

7.30 g (51.35 mmol) of ethyl 1-formylcyclopropanecarboxylate from Example 33A and 3.16 g (59.06 mmol) of ammonium chloride were initially charged in 9 ml of water and 9 ml of diethyl ether at 0° C. A solution of 2.52 g (51.35 mmol) of sodium cyanide in 6.4 ml of water was added dropwise at 0° C., with the temperature of the reaction mixture being kept below +10° C. at all times. The mixture was stirred at 0° C. for another 20 min and the phases were then separated. The aqueous phase was extracted three times with ethyl acetate. The combined organic phases were washed twice with saturated aqueous sodium chloride solution and dried over sodium sulphate and concentrated under reduced pressure at RT and 100 mbar. This gave 8.99 g (104% of theory; purity about 95% according to NMR) of the title compound, which were used for the next step without further purification.

$^1$H NMR (500 MHz, CDCl$_3$): δ [ppm]=1.04-1.11 (m, 1H), 1.15-1.22 (m, 1H), 1.29 (t, 3H), 1.39-1.46 (m, 1H), 1.47-1.53 (m, 1H), 4.16 (br. s, 1H), 4.24 (q, 2H).

Example 35A

Ethyl 1-(2-ethoxy-1-hydroxy-2-oxoethyl)cyclopropanecarboxylate

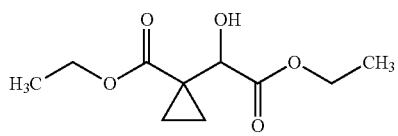

The reaction was carried out analogously to the method known from the literature (described in: A. de Meijere et al., Eur. J. Org. Chem. 2004, 3669-3678). Apparatus: three-necked flask with thermometer, septum with gas exhaust canula, gas inlet tube. A gentle stream of hydrogen chloride was passed through the apparatus. The reaction flask was cooled to −20° C. (bath temperature). 8.69 g (51.35 mmol) of ethyl 1-[cyano(hydroxy)methyl]cyclopropanecarboxylate from Example 34A were dissolved in 26 ml of dry ethanol and slowly added dropwise under a stream of hydrogen chloride. The temperature of the reaction mixture in the flask was kept below −10° C. at all times. After the addition had ended, the reaction mixture was saturated with hydrogen chloride at −20° C. (about 10 min), the cooling bath was removed and the mixture was then stirred at RT for 1 h. The reaction mixture was concentrated at RT (up to 7-8 mbar), 28 ml of ice-water were added to the residue (12.4 g of solid) at 0° C. and the mixture was stirred initially at 0° C. for 30 min and then at RT overnight. 70 ml of ethyl acetate were added, the reaction mixture was stirred at RT for 5 min and the phases were subsequently separated. The aqueous phase was extracted three times with ethyl acetate. The combined organic phases were washed twice with saturated aqueous sodium chloride solution and then dried over sodium sulphate and concentrated under reduced pressure at RT and 30 mbar. This gave 10.46 g (94% of theory; purity about 90% according to NMR) of the title compound, which were used for the next step without further purification.

$^1$H NMR (500 MHz, CDCl$_3$): δ [ppm]=1.00-1.07 (m, 1H), 1.10-1.18 (m, 1H), 1.18-1.33 (m, 6H), 1.33-1.44 (m, 2H), 3.42 (br. d, 1H), 3.57 (br. d, 1H), 4.07-4.20 (m, 2H), 4.20-4.34 (m, 2H).

Example 36A

Ethyl 1-[ethoxy(oxo)acetyl]cyclopropanecarboxylate

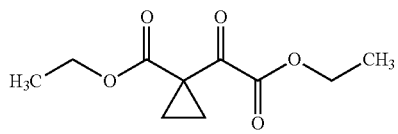

10.46 g (48.37 mmol) of ethyl 1-(2-ethoxy-1-hydroxy-2-oxoethyl)cyclopropanecarboxylate from Example 35A were initially charged in 300 ml of abs. diethyl ether, and 24.19 g (278.21 mmol) of activated manganese dioxide (Fluka) were added. The reaction mixture was stirred at RT for 2 h. The reaction mixture was then filtered with suction through Celite® and the filter residue was washed with diethyl ether. The filtrate was concentrated on a rotary evaporator at RT and 70 mbar. This gave 7.42 g (72% of theory; purity 95% according to NMR) of the title compound.

GC-MS (Method 8): R$_t$=3.87 min

MS (EIpos): m/z=141 (M-73)$^+$ $^1$H NMR (500 MHz, CDCl$_3$): δ [ppm]=1.25 (t, 3H), 1.39 (t, 3H), 1.62-1.67 (m, 2H), 1.68-1.73 (m, 2H), 4.20 (q, 2H), 4.36 (q, 2H).

Example 37A

Ethyl 1-{3-[5-fluoro-1-(4-methoxybenzyl)-6-methyl-1H-pyrazolo[3,4-b]pyridin-3-yl]-5-hydroxy-1,2,4-triazin-6-yl}cyclopropanecarboxylate

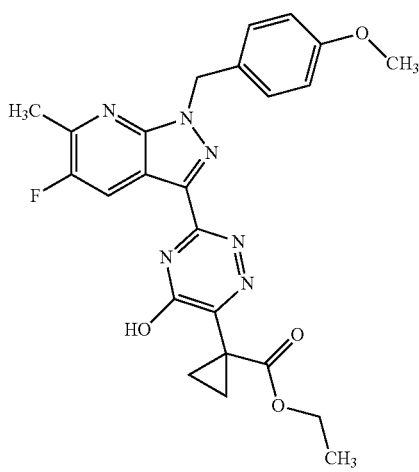

The reaction was carried out analogously to Example 41A.

Ethyl 1-[ethoxy(oxo)acetyl]cyclopropanecarboxylate (2.1 equivalents) from Example 36A is initially charged in ethanol (concentration about 0.2 molar) and heated to reflux. 5-Fluoro-1-(4-methoxybenzyl)-6-methyl-1H-pyrazolo[3,4-b]pyridine-3-carboximidohydrazide (1 equivalent) from Example 20A, suspended in a mixture of acetic acid/ethanol (1/4.6 ratio by volume; 20 equivalents of acetic acid; concentration of 5-fluoro-1-(4-methoxybenzyl)-6-methyl-1H-pyrazolo[3,4-b]pyridine-3-carboximidohydrazide about 0.2 molar) is then added a little at a time. The reaction mixture is stirred under reflux for 1 h. After cooling, the reaction mixture is concentrated on a rotary evaporator. The residue is purified by preparative HPLC (RP-C18, mobile phase: acetonitrile/water gradient with addition of 0.05% formic acid or 0.1% TFA).

Example 38A

Ethyl 1-{5-chloro-3-[5-fluoro-1-(4-methoxybenzyl)-6-methyl-1H-pyrazolo[3,4-b]pyridin-3-yl]-1,2,4-triazin-6-yl}cyclopropanecarboxylate

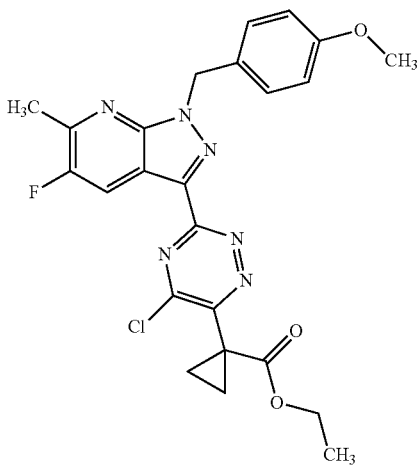

The reaction was carried out analogously to Example 42A.

At 0° C., tetrahydrothiophene 1,1-dioxide (sulpholane) (concentration about 0.1-0.2 molar) and phosphoryl chloride (50 equivalents) are added to ethyl 1-{3-[5-fluoro-1-(4-methoxybenzyl)-6-methyl-1H-pyrazolo[3,4-b]pyridin-3-yl]-5-hydroxy-1,2,4-triazin-6-yl}cyclopropanecarboxylate (1 equivalent) from Example 37A. The reaction mixture is treated with ultrasound until all starting materials are dissolved and then stirred at 0° C. for 5 min. The reaction mixture is then stirred at +10° C. for 2 h and used directly for the subsequent reaction.

Example 39A

3'-[5-Fluoro-1-(4-methoxybenzyl)-6-methyl-1H-pyrazolo[3,4-b]pyridin-3-yl]spiro[cyclopropane-1,7'-pyrrolo[2,3-e][1,2,4]triazin]-6'(5'H)-one

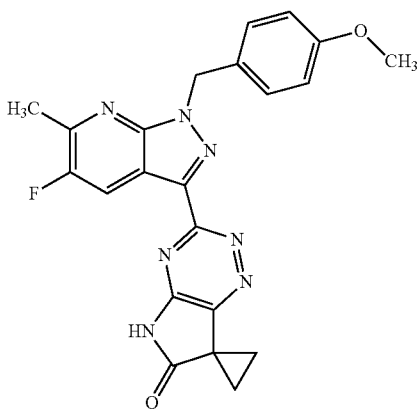

The reaction is carried out analogously to Example 43A. The reaction solution of ethyl 1-{5-chloro-3-[5-fluoro-1-(4-methoxybenzyl)-6-methyl-1H-pyrazolo[3,4-b]pyridin-3-yl]-1,2,4-triazin-6-yl}cyclopropanecarboxylate from Example 38A is diluted with dry acetonitrile (concentration about 0.01-0.05 molar) and then slowly added dropwise to a 33% strength aqueous ammonia solution cooled to 0° C. (72 ml of this ammonia solution per 1 mmol of ethyl 1-{5-chloro-3-[5-fluoro-1-(4-methoxybenzyl)-6-methyl-1H-pyrazolo[3,4-b]pyridin-3-yl]-1,2,4-triazin-6-yl}cyclopropanecarboxylate), with the internal temperature being kept between 0-12° C. (strongly exothermic). The mixture is then stirred at room temperature for about 48 h. The reaction mixture is concentrated on a rotary evaporator. Water is added to the residue and the mixture is extracted three times with dichloromethane. The combined organic phases are washed twice with water and once with saturated aqueous sodium chloride solution and then dried over sodium sulphate and concentrated under reduced pressure. The crude product is purified by preparative HPLC (RP18 column, mobile phase: acetonitrile/water gradient with addition of 0.05% formic acid or 0.1% TFA). The product fractions obtained are taken up in dichloromethane and washed twice with saturated aqueous sodium bicarbonate solution. The combined organic phases are dried over sodium sulphate, filtered and concentrated.

Example 40A

3'-(5-Fluoro-6-methyl-1H-pyrazolo[3,4-b]pyridin-3-yl)spiro[cyclopropane-1,7'-pyrrolo[2,3-e][1,2,4]triazin]-6'(5'H)-one

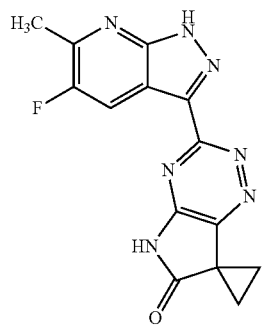 [SMILES: Cc1nc2[nH]nc(-c3nnc4c(n3)NC(=O)C43CC3)c2cc1F]

3'-[5-Fluoro-1-(4-methoxybenzyl)-6-methyl-1H-pyrazolo[3,4-b]pyridin-3-yl]spiro[cyclopropane-1,7'-pyrrolo[2,3-e][1,2,4]triazin]-6'(5'H)-one from Example 39A (1 equivalent) is initially charged in acetonitrile/water (2/1) (concentration about 0.05 molar), ammoniumcerium(IV) nitrate (4 equivalents) is added and the mixture is stirred at room temperature for 4 h. Water is added to the reaction mixture and the mixture is stirred at room temperature for 2 h and then filtered off, washed with water and dried under high vacuum.

Example 41A

Ethyl 1-[5-hydroxy-3-(6-methyl-1-{[2-(trimethylsilyl)ethoxy]methyl}-1H-pyrazolo[3,4-b]pyridin-3-yl)-1,2,4-triazin-6-yl]cyclopropanecarboxylate

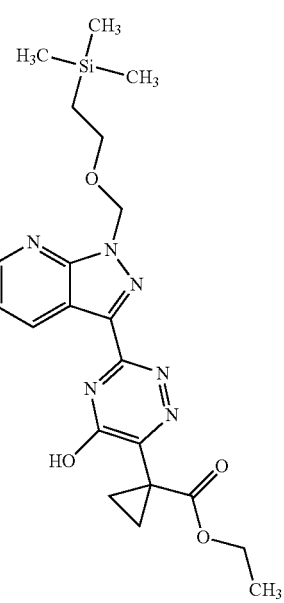

681 mg (3.18 mmol) of ethyl 1-[ethoxy(oxo)acetyl]cyclopropanecarboxylate from Example 36A in 16 ml of ethanol were heated to reflux. 485 mg (1.51 mmol) of 6-methyl-1-{[2-(trimethylsilyl)ethoxy]methyl}-1H-pyrazolo[3,4-b]pyridine-3-carboximidohydrazide from Example 28A, suspended in a mixture of 1.73 ml (30.27 mmol) of acetic acid and 8 ml of ethanol, were then added a little at a time. The reaction mixture was stirred under reflux for 1 h. After cooling, the reaction mixture was concentrated on a rotary evaporator. The residue was purified by preparative HPLC (RP-C18, mobile phase: acetonitrile/water gradient with addition of 0.05% formic acid). This gave 127 mg of the title compound (15% of theory; purity 86%).

LC-MS (Method 1): $R_t$=1.18 min

MS (ESIpos): m/z=471 (M+H)$^+$ $^1$H NMR (500 MHz, DMSO-d$_6$): δ [ppm]=−0.13-0.08 (m, 9H), 0.83-0.88 (m, 2H), 1.11 (t, 3H), 1.32 (br. s, 2H), 1.41-1.45 (m, 2H), 2.68 (s, 3H), 3.67 (t, 2H), 4.06 (q, 2H), 5.88 (s, 2H), 7.40 (d, 1H), 8.61 (d, 1H), 14.40 (br. s, 1H).

Example 42A

Ethyl 1-[5-chloro-3-(6-methyl-1-{[2-(trimethylsilyl)ethoxy]methyl}-1H-pyrazolo[3,4-b]pyridin-3-yl)-1,2,4-triazin-6-yl]cyclopropanecarboxylate

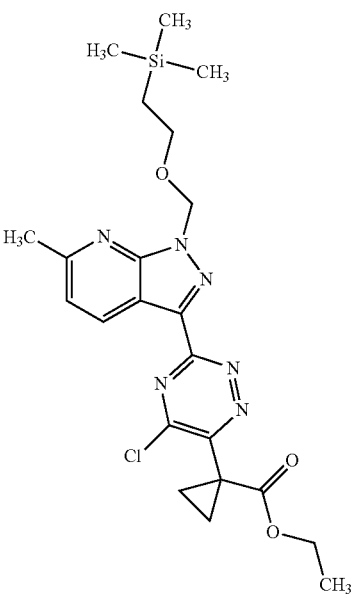 [SMILES: CCOC(=O)C1(c2nnc(-c3nn(COCC[Si](C)(C)C)c4nc(C)ccc34)nc2Cl)CC1]

At 0° C., 2.5 ml of tetrahydrothiophene 1,1-dioxide (sulpholane) and 1.27 ml of phosphoryl chloride were added to 127 mg (0.23 mmol, purity 86%) of ethyl 1-[5-hydroxy-3-(6-methyl-1-{[2-(trimethylsilyl)ethoxy]methyl}-1H-pyrazolo[3,4-b]pyridin-3-yl)-1,2,4-triazin-6-yl]cyclopropanecarboxylate from Example 41A. The reaction mixture was treated with ultrasound until all starting materials had been dissolved and then stirred at 0° C. for 5 min. The reaction mixture was then stirred at +10° C. for 90 min and used directly for the subsequent reaction.

LC-MS (Method 1): $R_t$=1.43 min

MS (ESIpos): m/z=489 (M+H)$^+$

Example 43A

3'-(6-Methyl-1-{[2-(trimethylsilyl)ethoxy]methyl}-1H-pyrazolo[3,4-b]pyridin-3-yl)spiro[cyclopropane-1,7'-pyrrolo[2,3-e][1,2,4]triazin]-6'(5'H)-one

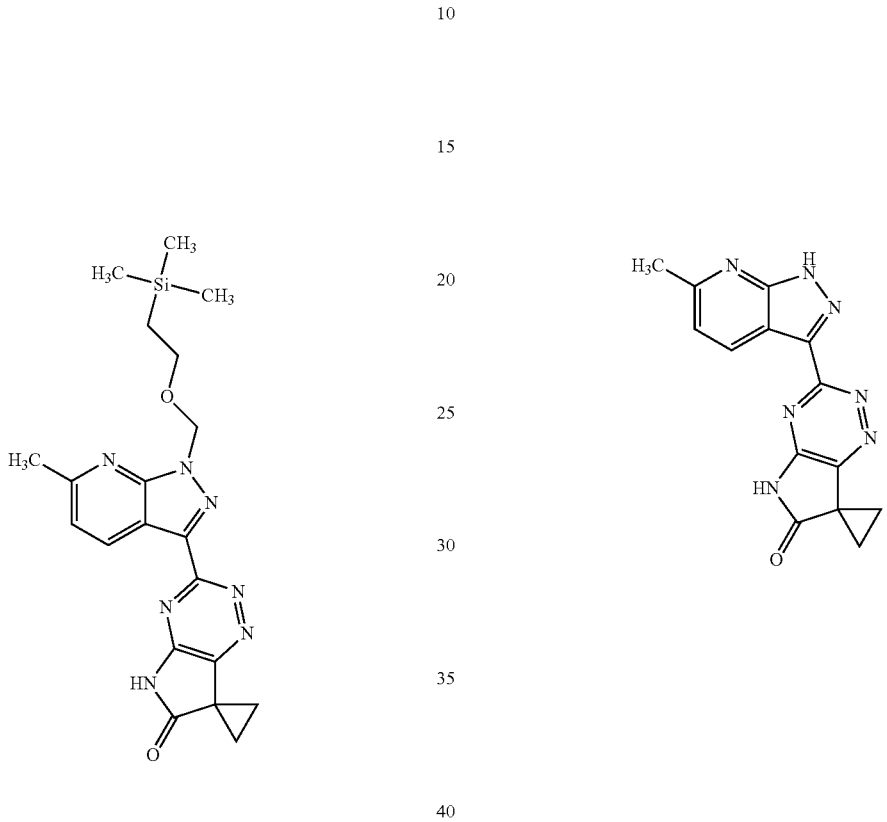

The reaction solution of ethyl 1-[5-chloro-3-(6-methyl-1-{[2-(trimethylsilyl)ethoxy]methyl}-1H-pyrazolo[3,4-b]pyridin-3-yl)-1,2,4-triazin-6-yl]cyclopropanecarboxylate from Example 42A was diluted with 30 ml of dry acetonitrile and then slowly added dropwise to a 33% strength aqueous ammonia solution (41 ml) cooled to 0° C., with the internal temperature being kept between 0-12° C. The mixture was then stirred at room temperature for about 48 h. The reaction mixture was concentrated on a rotary evaporator. Water was added to the residue and the mixture was extracted three times with methyl tert-butyl ether. The combined organic phases were washed twice with water and once with saturated aqueous sodium chloride solution and then dried over sodium sulphate and concentrated under reduced pressure. The crude product was used for the next step without further purification.

LC-MS (Method 4): $R_t$=3.42 min

MS (EIpos): m/z=424 [M+H]$^+$.

Example 44A

3'-(6-Methyl-1H-pyrazolo[3,4-b]pyridin-3-yl)spiro[cyclopropane-1,7'-pyrrolo[2,3-e][1,2,4]triazin]-6'(5'H)-one The crude product 3'-(6-methyl-1-{[2-(trimethylsilyl)ethoxy]methyl}-1H-pyrazolo[3,4-b]pyridin-3-yl)spiro[cyclopropane-1,7'-pyrrolo[2,3-e][1,2,4]triazin]-6'(5'H)-one from Example 43A was initially charged in 13 ml of dichloromethane and 13 ml of trifluoroacetic acid, and the mixture was stirred at RT for 30 min. The reaction mixture was concentrated under reduced pressure at 30° C. The residue was concentrated twice from dioxane and once from toluene under reduced pressure at 30° C. and then dried under high vacuum. 5 ml of THF and 5 ml of 5% strength aqueous ammonia solution were added, and the mixture was kept at RT for 5 min. The reaction mixture was concentrated under reduced pressure at 30° C. and the residue was concentrated twice from a mixture of 5 ml of THF and 5 ml of 5% strength aqueous ammonia solution under reduced pressure at 30° C. The residue was purified by preparative HPLC (RP-C18, mobile phase: acetonitrile/water gradient with addition of 0.05% formic acid). This gave 40 mg (46% of theory; purity about 90% according to NMR) of the title compound.

LC-MS (Method 1): $R_t$=0.65 min

MS (ESIpos): m/z=294 (M+H)$^+$ $^1$H NMR (500 MHz, DMSO-d$_6$): δ [ppm]=1.82-1.86 (m, 2H), 1.96-2.00 (m, 2H), 2.63 (s, 3H), 7.26 (d, 1H), 8.66 (d, 1H), 12.31 (br. s, 1H), 14.02 (br. s, 1H).

WORKING EXAMPLES

Example 1

3-[1-(2,3-Difluorobenzyl)-5-fluoro-6-methyl-1H-pyrazolo[3,4-b]pyridin-3-yl]-7,7-dimethyl-5,7-dihydro-6H-pyrrolo[2,3-e][1,2,4]triazin-6-one

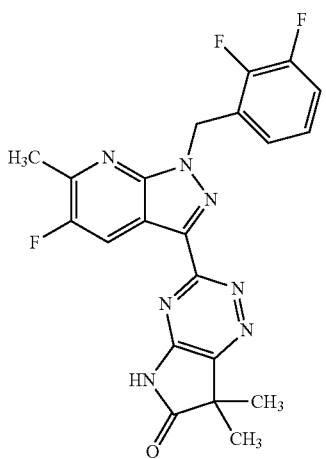 [SMILES: Cc1nc2c(cc1F)c(-c1nnc3c(n1)NC(=O)C3(C)C)nn2Cc1cccc(F)c1F]

The reaction solution of methyl 2-{5-chloro-3-[1-(2,3-difluorobenzyl)-5-fluoro-6-methyl-1H-pyrazolo[3,4-b]pyridin-3-yl]-1,2,4-triazin-6-yl}-2-methylpropanoate from Example 9A was diluted with 72 ml of dry acetonitrile and then slowly added dropwise at 0° C. to 109 ml of a 33% strength aqueous ammonia solution (strongly exothermic). The reaction mixture was stirred at room temperature overnight and then concentrated on a rotary evaporator at 50° C. 100 ml of water and 150 ml of dichloromethane were added to the residue and the mixture was vigorously stirred at room temperature for 30 min. The two phases were separated and the aqueous phase was extracted once with dichloromethane. The combined organic phases were dried over sodium sulphate, filtered and concentrated.

9.6 ml of abs. dioxane and 2.4 ml of acetic acid were added to the crude product, and the mixture was stirred in a microwave at 100° C. for 8 h. The mixture was concentrated and the residue was stirred with water for 30 min. The solid obtained was filtered off and dried under high vacuum. 5.5 ml of ethanol were added to the solid. The suspension was heated to 50° C. and 3.3 ml of dichloromethane were added such that a clear solution was obtained. After cooling to 0° C., a first product fraction of the target compound was filtered off as a solid (241 mg). The filtrate was concentrated, and 3 ml of ethanol were added. The suspension was heated to 50° C. and 1.5 ml of dichloromethane were added such that a clear solution was obtained. After cooling to RT, a second product fraction of the target compound was filtered off as a solid (127 mg). The two product fractions were combined and lyophilized. This gave 368 mg (52% of theory; purity 94%) of the title compound.

LC-MS (Method 2): $R_t$=3.35 min

MS (EIpos): m/z=440 [M+H]$^+$.

$^1$H NMR (500 MHz, DMSO-d$_6$): δ [ppm]=1.45 (s, 6H), 2.65 (d, 3H), 5.89 (s, 2H), 7.03-7.09 (m, 1H), 7.14-7.21 (m, 1H), 7.36-7.44 (m, 1H), 8.45 (d, 1H), 12.15 (br. s, 1H).

Example 2

Sodium 3-[1-(2,3-difluorobenzyl)-5-fluoro-6-methyl-1H-pyrazolo[3,4-b]pyridin-3-yl]-7,7-dimethyl-6-oxo-6,7-dihydropyrrolo[2,3-e][1,2,4]triazin-5-ide

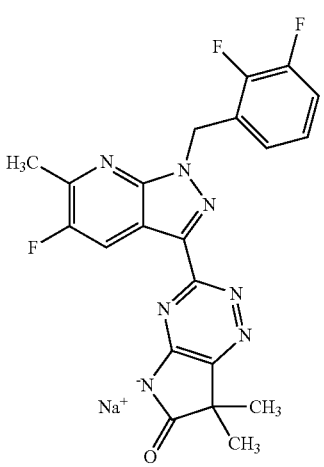

20 mg (0.046 mmol) of 3-[1-(2,3-difluorobenzyl)-5-fluoro-6-methyl-1H-pyrazolo[3,4-b]pyridin-3-yl]-7,7-dimethyl-5,7-dihydro-6H-pyrrolo[2,3-e][1,2,4]triazin-6-one from Example 1 were dissolved in 0.1 ml of THF (gently warmed and then briefly sonicated), and 0.046 ml of a 1 N sodium hydroxide solution was added. The reaction mixture was stirred at RT for 2 min and then at 50° C. for 5 min. The mixture was then concentrated and the product was dried under high vacuum. This gave 20 mg (91% of theory) of the title compound.

LC-MS (Method 1): $R_t$=1.09 min

MS (EIpos): m/z=440 [M-Na+2H]$^+$.

$^1$H NMR (500 MHz, DMSO-d$_6$): δ [ppm]=1.16 (s, 6H), 2.63 (d, 3H), 5.84 (s, 2H), 6.97-7.03 (m, 1H), 7.13-7.21 (m, 1H), 7.35-7.44 (m, 1H), 8.46 (d, 1H).

Example 3

3-[1-(2,3-Difluorobenzyl)-6-methyl-1H-pyrazolo[3,4-b]pyridin-3-yl]-7,7-dimethyl-5,7-dihydro-6H-pyrrolo[2,3-e][1,2,4]triazin-6-one

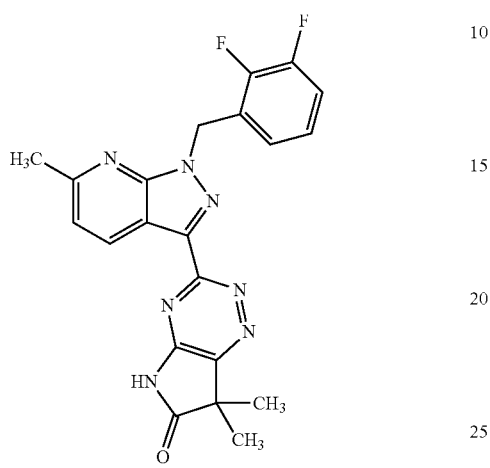

The reaction solution of methyl 2-{5-chloro-3-[1-(2,3-difluorobenzyl)-6-methyl-1H-pyrazolo[3,4-b]pyridin-3-yl]-1,2,4-triazin-6-yl}-2-methylpropanoate from Example 16A was diluted with 85 ml of dry acetonitrile and then slowly added dropwise to a 33% strength aqueous ammonia solution (78 ml) cooled to 0° C. (strongly exothermic; internal temperature: 0-12° C.). The reaction mixture was stirred at room temperature overnight. The organic phase was separated off and concentrated on a rotary evaporator to about 30 ml, and water was then added. The mixture was treated in an ultrasonic bath for 1.5 h. The solid was filtered off with suction, washed with water and a little acetonitrile and dried under high vacuum. The residue was dissolved in DMF (a few drops) and dichloromethane and purified by flash chromatography (mobile phase: cyclohexane/ethyl acetate gradient). The product fractions were concentrated and ethyl acetate and diisopropyl ether were added to the residue. The solid was filtered off with suction and dried under high vacuum. Since the product still contained a little DMF, it was purified further as follows: ethanol/water were added to the crude product, the mixture was stirred at 90° C. for 30 min and cooled in an ice bath and the product was washed with ethanol/water and dried under high vacuum. The solid was dissolved in 60 ml of ethanol under reflux, cooled and concentrated under reduced pressure to about 10 ml. The ethanol/water filtrate from the first extraction experiment and 100 ml of water were added. The mixture was then briefly cooled in an ice bath and the solid was filtered off with suction, washed with water and a little water/ethanol and dried under high vacuum overnight. This gave 290 mg of the target compound (23% of theory).

LC-MS (Method 1): $R_t$=1.05 min

MS (EIpos): m/z=422 [M+H]$^+$.

$^1$H NMR (500 MHz, DMSO-d$_6$): δ [ppm]=1.45 (s, 6H), 2.68 (s, 3H), 5.88 (s, 2H), 7.00-7.05 (m, 1H), 7.14-7.20 (m, 1H), 7.35-7.42 (m, 1H), 7.36 (d, 1H), 8.72 (d, 1H), 12.12 (br. s, 1H).

Example 4

Sodium 3-[1-(2,3-difluorobenzyl)-6-methyl-1H-pyrazolo[3,4-b]pyridin-3-yl]-7,7-dimethyl-6-oxo-6,7-dihydropyrrolo[2,3-e][1,2,4]triazin-5-ide

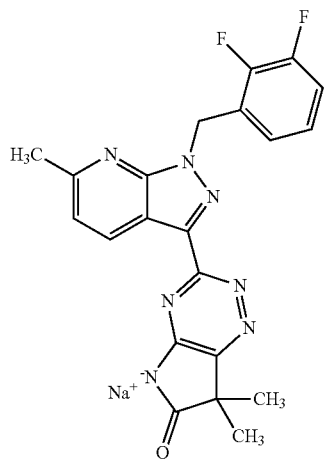

14.7 mg (0.035 mmol) of 3-[1-(2,3-difluorobenzyl)-6-methyl-1H-pyrazolo[3,4-b]pyridin-3-yl]-7,7-dimethyl-5,7-dihydro-6H-pyrrolo[2,3-e][1,2,4]triazin-6-one from Example 3 were dissolved in 0.2 ml of THF, and 0.035 ml of a 1 N aqueous sodium hydroxide solution was added. The reaction mixture was stirred at RT for 2 min and then at 50° C. for 5 min. The mixture was then concentrated and dried under high vacuum. This gave 15.4 mg (99.6% of theory) of the title compound.

LC-MS (Method 1): $R_t$=1.05 min

MS (EIpos): m/z=422 [M-Na+2H]$^+$.

$^1$H NMR (400 MHz, DMSO-d$_6$): δ [ppm]=1.15 (s, 6H), 2.65 (s, 3H), 5.82 (s, 2H), 6.91-6.98 (m, 1H), 7.11-7.19 (m, 1H), 7.26 (d, 1H), 7.33-7.43 (m, 1H), 8.71 (d, 1H).

Example 5

3-[5-Fluoro-1-(2-fluoro-4-methylbenzyl)-6-methyl-1H-pyrazolo[3,4-b]pyridin-3-yl]-7,7-dimethyl-5,7-dihydro-6H-pyrrolo[2,3-e][1,2,4]triazin-6-one

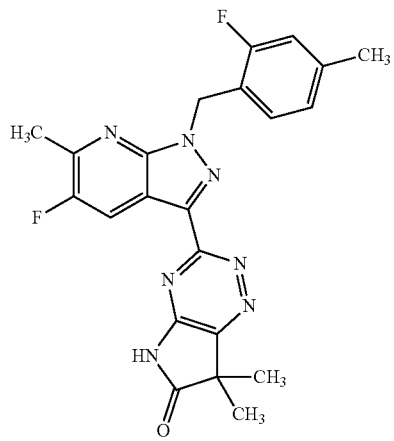

80 mg (0.255 mmol) of 3-(5-fluoro-6-methyl-1H-pyrazolo[3,4-b]pyridin-3-yl)-7,7-dimethyl-5,7-dihydro-6H-pyrrolo[2,3-e][1,2,4]triazin-6-one from Example 24A were initially charged in 2.7 ml of DMF and heated to 80° C. 333 mg (1.02 mmol) of caesium carbonate were added to the mixture. 40 mg (0.19 mmol) of 1-(bromomethyl)-2-fluoro-4-methylbenzene, dissolved in 0.27 ml of DMF, were then added in 10 portions over a period of 10 min to the reaction mixture at 80° C., with about 1 min of stirring at 80° C. between the individual additions. The mixture was then stirred at 80° C. for 10 min. The mixture was then diluted with ethyl acetate and washed twice with water. The organic phase was dried over sodium sulphate, filtered and concentrated. The crude product was dissolved in dichloromethane/methanol/1 N solution of ammonia in methanol (2/2/1) and purified by thick-layer chromatography (mobile phase: dichloromethane/methanol=40/1). This gave 7 mg of the target compound (6% of theory; purity 98%).

LC-MS (Method 1): $R_t$=1.17 min

MS (EIpos): m/z=436 [M+H]$^+$.

$^1$H NMR (500 MHz, DMSO-d$_6$): δ [ppm]=1.44 (s, 6H), 2.28 (s, 3H), 2.65 (d, 3H), 5.77 (s, 2H), 6.97 (d, 1H), 7.05 (d, 1H), 7.13 (t, 1H), 8.44 (d, 1H), 12.14 (br. s, 1H).

Example 6

3-[1-(2-Fluoro-4-methylbenzyl)-6-methyl-1H-pyrazolo[3,4-b]pyridin-3-yl]-7,7-dimethyl-5,7-dihydro-6H-pyrrolo[2,3-e][1,2,4]triazin-6-one

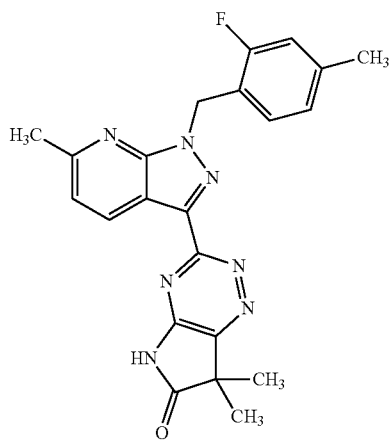

100 mg (0.31 mmol, purity 90%) of 7,7-dimethyl-3-(6-methyl-1H-pyrazolo[3,4-b]pyridin-3-yl)-5,7-dihydro-6H-pyrrolo[2,3-e][1,2,4]triazin-6-one from Example 32A were initially charged in 3.2 ml of DMF and heated to 80° C. 397 mg (1.22 mmol) of caesium carbonate were added to the mixture. 54 mg (0.26 mmol) of 1-(bromomethyl)-2-fluoro-4-methylbenzene, dissolved in 0.32 ml of DMF, were then added in 10 portions over a period of 10 min to the reaction mixture at 80° C., with about 1 min of stirring at 80° C. between the individual additions. The mixture was then stirred at 80° C. for 10 min. The mixture was then cooled, and water and 0.5 ml of formic acid were added. The resulting precipitate was filtered off and washed with acetonitrile and the filtrate was purified by preparative HPLC (RP-C18, mobile phase: acetonitrile/water gradient with addition of 0.05% formic acid). This gave 20 mg of the target compound (16% of theory).

LC-MS (Method 1): $R_t$=1.06 min

MS (EIpos): m/z=418 [M+H]$^+$.

$^1$H NMR (500 MHz, DMSO-d$_6$): δ [ppm]=1.45 (s, 6H), 2.28 (s, 3H), 2.67 (s, 3H), 5.77 (s, 2H), 6.96 (d, 1H), 7.05 (d, 1H), 7.07-7.13 (m, 1H), 7.34 (d, 1H), 8.70 (d, 1H), 12.13 (br. s, 1H).

Example 7

3-[1-(2,4-Difluorobenzyl)-5-fluoro-6-methyl-1H-pyrazolo[3,4-b]pyridin-3-yl]-7,7-dimethyl-5,7-dihydro-6H-pyrrolo[2,3-e][1,2,4]triazin-6-one

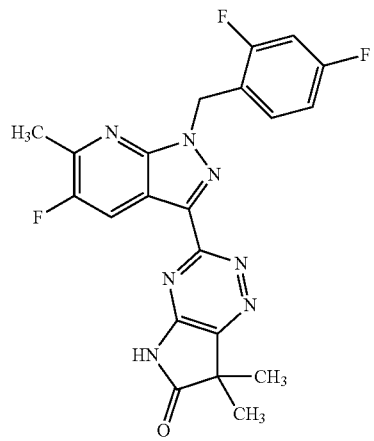 [SMILES: Cc1nc2c(cc1F)c(-c1nnc3c(n1)NC(=O)C3(C)C)nn2Cc1ccc(F)cc1F]

80 mg (0.255 mmol) of 3-(5-fluoro-6-methyl-1H-pyrazolo[3,4-b]pyridin-3-yl)-7,7-dimethyl-5,7-dihydro-6H-pyrrolo[2,3-e][1,2,4]triazin-6-one from Example 24A were initially charged in 2.7 ml of DMF and heated to 80° C. 333 mg (1.02 mmol) of caesium carbonate were added to the mixture. 40.5 mg (0.19 mmol) of 1-(bromomethyl)-2,4-difluorobenzene, dissolved in 0.27 ml of DMF, were then added in 10 portions over a period of 10 min to the reaction mixture at 80° C., with about 1 min of stirring at 80° C. between the individual additions. The mixture was then stirred at 80° C. for 10 min. The reaction mixture was diluted with ethyl acetate and washed twice with water. The organic phase was dried over sodium sulphate, filtered and concentrated. The crude product was dissolved in dichloromethane/methanol/1 N solution of ammonia in methanol (2/2/1) and purified by thick-layer chromatography (mobile phase: dichloromethane/methanol=40/1). This gave 17 mg of the target compound (15% of theory).

LC-MS (Method 1): $R_t$=1.13 min

MS (EIpos): m/z=440 [M+H]$^+$.

$^1$H NMR (500 MHz, DMSO-d$_6$): δ [ppm]=1.43 (s, 6H), 2.65 (d, 3H), 5.80 (s, 2H), 7.04-7.10 (m, 1H), 7.25-7.31 (m, 1H), 7.32-7.39 (m, 1H), 8.44 (d, 1H), 12.15 (br. s, 1H).

Example 8

3-[1-(2,4-Difluorobenzyl)-6-methyl-1H-pyrazolo[3,4-b]pyridin-3-yl]-7,7-dimethyl-5,7-dihydro-6H-pyrrolo[2,3-e][1,2,4]triazin-6-one

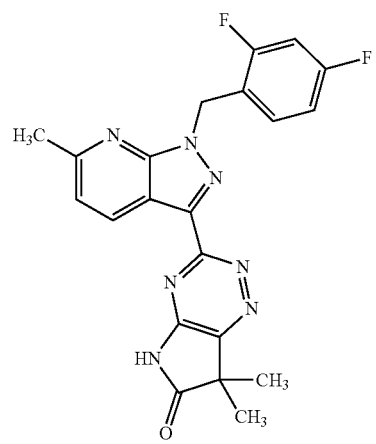 [SMILES: Cc1ccc2c(-c3nnc4c(n3)NC(=O)C4(C)C)nn(Cc3ccc(F)cc3F)c2n1]

100 mg (0.31 mmol, purity 90%) of 7,7-dimethyl-3-(6-methyl-1H-pyrazolo[3,4-b]pyridin-3-yl)-5,7-dihydro-6H-pyrrolo[2,3-e][1,2,4]triazin-6-one from Example 32A were initially charged in 3.2 ml of DMF and heated to 80° C. 397 mg (1.22 mmol) of caesium carbonate were added to the mixture. 55 mg (0.26 mmol) of 1-(bromomethyl)-2,4-difluorobenzene, dissolved in 0.32 ml of DMF, were then added in 10 portions over a period of 10 min to the reaction mixture at 80° C., with about 1 min of stirring at 80° C. between the individual additions. The mixture was then stirred at 80° C. for 10 min. The reaction mixture was cooled, and water and 0.5 ml of formic acid were added. The resulting precipitate was filtered off and washed with acetonitrile and the filtrate was purified by preparative HPLC (RP-C18, mobile phase: acetonitrile/water gradient with addition of 0.05% formic acid). This gave 29 mg of the target compound (22% of theory).

LC-MS (Method 1): $R_t$=1.02 min

MS (EIpos): m/z=422 [M+H]$^+$.

$^1$H NMR (500 MHz, DMSO-$d_6$): δ [ppm]=1.44 (s, 6H), 2.68 (s, 3H), 5.80 (s, 2H), 7.03-7.10 (m, 1H), 7.25-7.35 (m, 2H), 7.36 (d, 1H), 8.71 (d, 1H), 12.16 (br. s, 1H).

Example 9

3-[1-(4-Chloro-2-fluorobenzyl)-5-fluoro-6-methyl-1H-pyrazolo[3,4-b]pyridin-3-yl]-7,7-dimethyl-5,7-dihydro-6H-pyrrolo[2,3-e][1,2,4]triazin-6-one

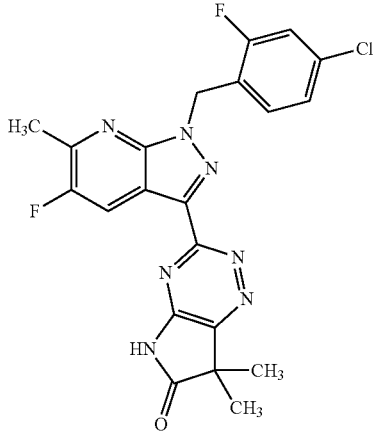 [SMILES: Cc1nc2c(cc1F)c(-c1nnc3c(n1)NC(=O)C3(C)C)nn2Cc1ccc(Cl)cc1F]

80 mg (0.255 mmol) of 3-(5-fluoro-6-methyl-1H-pyrazolo[3,4-b]pyridin-3-yl)-7,7-dimethyl-5,7-dihydro-6H-pyrrolo[2,3-e][1,2,4]triazin-6-one from Example 24A were initially charged in 2.7 ml of DMF and heated to 80° C. 333 mg (1.02 mmol) of caesium carbonate were added to the mixture. 44 mg (0.19 mmol) of 1-(bromomethyl)-4-chloro-2-fluorobenzene, dissolved in 0.27 ml of DMF, were then added in 10 portions over a period of 10 min to the reaction mixture at 80° C., with about 1 min of stirring at 80° C. between the individual additions. The mixture was then stirred at 80° C. for 10 min. The reaction mixture was diluted with ethyl acetate and washed twice with water. The organic phase was dried over sodium sulphate, filtered and concentrated. The crude product was dissolved in dichloromethane/methanol/1 N solution of ammonia in methanol (2/2/1) and purified by thick-layer chromatography (mobile phase: dichloromethane/methanol=40/1). This gave 24 mg of the target compound (21% of theory).

LC-MS (Method 1): $R_t$=1.19 min

MS (EIpos): m/z=456 [M+H]$^+$.

$^1$H NMR (500 MHz, DMSO-$d_6$): δ [ppm]=1.45 (s, 6H), 2.65 (d, 3H), 5.82 (s, 2H), 7.26-7.31 (m, 2H), 7.46-7.50 (m, 1H), 8.44 (d, 1H), 12.16 (br. s, 1H).

Example 10

3-[1-(4-Chloro-2-fluorobenzyl)-6-methyl-1H-pyrazolo[3,4-b]pyridin-3-yl]-7,7-dimethyl-5,7-dihydro-6H-pyrrolo[2,3-e][1,2,4]triazin-6-one

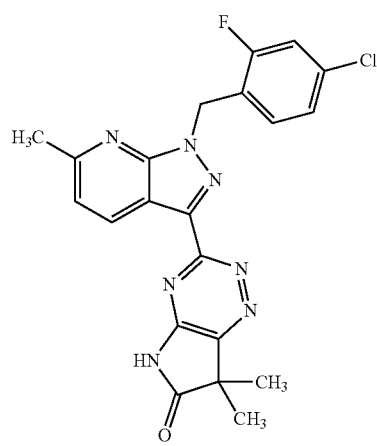 [SMILES: Cc1ccc2c(-c3nnc4c(n3)NC(=O)C4(C)C)nn(Cc3ccc(Cl)cc3F)c2n1]

100 mg (0.34 mmol; purity 90%) of 7,7-dimethyl-3-(6-methyl-1H-pyrazolo[3,4-b]pyridin-3-yl)-5,7-dihydro-6H-pyrrolo[2,3-e][1,2,4]triazin-6-one from Example 32A were initially charged in 3.2 ml of DMF and heated to 80° C. 441 mg (1.36 mmol) of caesium carbonate were added to the mixture. 64 mg (0.29 mmol) of 1-(bromomethyl)-4-chloro-2-fluorobenzene, dissolved in 0.32 ml of DMF, were then added in 10 portions over a period of 10 min to the reaction mixture at 80° C., with about 1 min of stirring at 80° C. between the individual additions. The mixture was then stirred at 80° C. for 10 min. The reaction mixture was cooled, and water and 0.5 ml of formic acid were added. The resulting precipitate was filtered off and washed with acetonitrile and the filtrate was purified by preparative HPLC (RP-C18, mobile phase: acetonitrile/water gradient with addition of 0.05% formic acid). This gave 30 mg of the target compound (21% of theory).

LC-MS (Method 1): $R_t$=1.08 min

MS (EIpos): m/z=438 [M+H]$^+$.

$^1$H NMR (500 MHz, DMSO-d$_6$): δ [ppm]=1.45 (s, 6H), 2.68 (s, 3H), 5.81 (s, 2H), 7.22-7.29 (m, 2H), 7.36 (d, 1H), 7.46-7.50 (m, 1H), 8.71 (d, 1H), 12.13 (br. s, 1H).

Example 11

3-[5-Fluoro-6-methyl-1-(2,3,6-trifluorobenzyl)-1H-pyrazolo[3,4-b]pyridin-3-yl]-7,7-dimethyl-5,7-dihydro-6H-pyrrolo[2,3-e][1,2,4]triazin-6-one

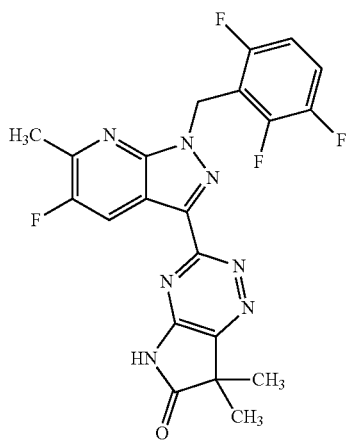 [SMILES: Cc1nc2c(cc1F)c(-c1nnc3c(n1)NC(=O)C3(C)C)nn2Cc1c(F)ccc(F)c1F]

80 mg (0.255 mmol) of 3-(5-fluoro-6-methyl-1H-pyrazolo[3,4-b]pyridin-3-yl)-7,7-dimethyl-5,7-dihydro-6H-pyrrolo[2,3-e][1,2,4]triazin-6-one from Example 24A were initially charged in 2.7 ml of DMF and heated to 80° C. 333 mg (1.02 mmol) of caesium carbonate were added to the mixture. 44.4 mg (0.19 mmol) of 2-(bromomethyl)-1,3,4-trifluorobenzene, dissolved in 0.27 ml of DMF, were then added in 10 portions over a period of 10 min to the reaction mixture at 80° C., with about 1 min of stirring at 80° C. between the individual additions. The mixture was then stirred at 80° C. for 10 min. The reaction mixture was diluted with ethyl acetate and washed twice with water. The organic phase was dried over sodium sulphate, filtered and concentrated. The crude product was purified by thick-layer chromatography (mobile phase: dichloromethane/methanol=40/1). This gave 33 mg of the target compound (28% of theory).

LC-MS (Method 1): $R_t$=1.09 min

MS (EIpos): m/z=458 [M+H]$^+$.

$^1$H NMR (500 MHz, DMSO-d$_6$): δ [ppm]=1.44 (s, 6H), 2.66 (d, 3H), 5.86 (s, 2H), 7.16-7.24 (m, 1H), 7.50-7.60 (m, 1H), 8.43 (d, 1H), 12.14 (br. s, 1H).

Example 12

7,7-Dimethyl-3-[6-methyl-1-(2,3,6-trifluorobenzyl)-1H-pyrazolo[3,4-b]pyridin-3-yl]-5,7-dihydro-6H-pyrrolo[2,3-e][1,2,4]triazin-6-one

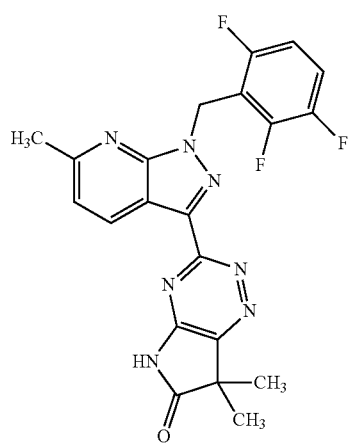 [SMILES: Cc1ccc2c(-c3nnc4c(n3)NC(=O)C4(C)C)nn(Cc3c(F)ccc(F)c3F)c2n1]

100 mg (0.27 mmol; purity 90%) of 7,7-dimethyl-3-(6-methyl-1H-pyrazolo[3,4-b]pyridin-3-yl)-5,7-dihydro-6H-pyrrolo[2,3-e][1,2,4]triazin-6-one from Example 32A were initially charged in 2.8 ml of DMF and heated to 80° C. 353 mg (1.08 mmol) of caesium carbonate were added to the mixture. 56 mg (0.24 mmol) of 2-(bromomethyl)-1,3,4-trifluorobenzene, dissolved in 0.28 ml of DMF, were then added in 10 portions over a period of 10 min to the reaction mixture at 80° C., with about 1 min of stirring at 80° C. between the individual additions. The mixture was then stirred at 80° C. for 10 min. The reaction mixture was cooled, water and 0.5 ml of formic acid were added and the product was purified by preparative HPLC (RP-C18, mobile phase: acetonitrile/water gradient with addition of 0.05% formic acid). This gave 38 mg of the target compound (32% of theory).

LC-MS (Method 1): $R_t$=1.02 min

MS (EIpos): m/z=440 [M+H]$^+$.

$^1$H NMR (500 MHz, DMSO-d$_6$): δ [ppm]=1.44 (s, 6H), 2.69 (s, 3H), 5.85 (s, 2H), 7.16-7.22 (m, 2H), 7.36 (d, 1H), 7.50-7.58 (m, 1H), 8.69 (d, 1H), 12.13 (br. s, 1H).

Example 13

3-[1-(3-Chloro-2-fluorobenzyl)-5-fluoro-6-methyl-1H-pyrazolo[3,4-b]pyridin-3-yl]-7,7-dimethyl-5,7-dihydro-6H-pyrrolo[2,3-e][1,2,4]triazin-6-one

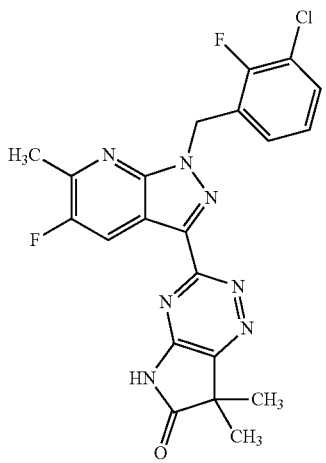 [SMILES: Cc1nc2c(cc1F)c(-c1nnc3c(n1)NC(=O)C3(C)C)nn2Cc1cccc(Cl)c1F]

80 mg (0.255 mmol) of 3-(5-fluoro-6-methyl-1H-pyrazolo[3,4-b]pyridin-3-yl)-7,7-dimethyl-5,7-dihydro-6H-pyrrolo[2,3-e][1,2,4]triazin-6-one from Example 24A were initially charged in 2.7 ml of DMF and heated to 80° C. 333 mg (1.02 mmol) of caesium carbonate were added to the mixture. 44.6 mg (0.19 mmol) of 1-(bromomethyl)-3-chloro-2-fluorobenzene, dissolved in 0.27 ml of DMF, were then added in 10 portions over a period of 10 min to the reaction mixture at 80° C., with about 1 min of stirring at 80° C. between the individual additions. The mixture was then stirred at 80° C. for 10 min. The reaction mixture was diluted with ethyl acetate and washed twice with water. The organic phase was dried over sodium sulphate, filtered and concentrated. The crude product was purified by thick-layer chromatography (mobile phase: dichloromethane/methanol=40/1). This gave 26 mg of the target compound (21% of theory).

LC-MS (Method 1): $R_t$=1.15 min

MS (EIpos): m/z=456 [M+H]$^+$.

$^1$H NMR (500 MHz, DMSO-d$_6$): δ [ppm]=1.44 (s, 6H), 2.65 (d, 3H), 5.88 (s, 2H), 7.18-7.26 (m, 2H), 7.53-7.58 (m, 1H), 8.45 (d, 1H), 12.14 (br. s, 1H).

Example 14

3-[1-(3-Chloro-2-fluorobenzyl)-6-methyl-1H-pyrazolo[3,4-b]pyridin-3-yl]-7,7-dimethyl-5,7-dihydro-6H-pyrrolo[2,3-e][1,2,4]triazin-6-one

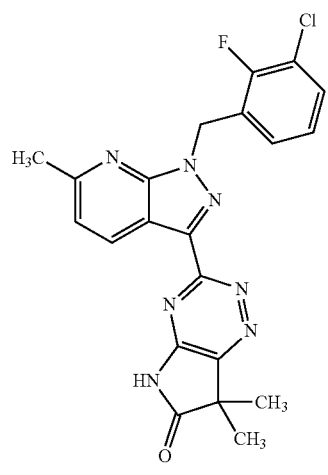 [SMILES: Cc1ccc2c(-c3nnc4c(n3)NC(=O)C4(C)C)nn(Cc3cccc(Cl)c3F)c2n1]

100 mg (0.31 mmol, purity 90%) of 7,7-dimethyl-3-(6-methyl-1H-pyrazolo[3,4-b]pyridin-3-yl)-5,7-dihydro-6H-pyrrolo[2,3-e][1,2,4]triazin-6-one from Example 32A were initially charged in 3.2 ml of DMF and heated to 80° C. 397 mg (1.22 mmol) of caesium carbonate were added to the mixture. 60 mg (0.26 mmol) of 1-(bromomethyl)-3-chloro-2-fluorobenzene, dissolved in 0.32 ml of DMF, were then added in 10 portions over a period of 10 min to the reaction mixture at 80° C., with about 1 min of stirring at 80° C. between the individual additions. The mixture was then stirred at 80° C. for 10 min. The reaction mixture was cooled, and water and 0.5 ml of formic acid were added. The resulting precipitate was filtered off and washed with acetonitrile and the filtrate was purified by preparative HPLC (RP-C18, mobile phase: acetonitrile/water gradient with addition of 0.05% formic acid). This gave 33 mg of the target compound (25% of theory).

LC-MS (Method 1): $R_t$=1.10 min

MS (EIpos): m/z=438 [M+H]$^+$.

$^1$H NMR (500 MHz, DMSO-d$_6$): δ [ppm]=1.44 (s, 6H), 2.68 (s, 3H), 5.87 (s, 2H), 7.16-7.23 (m, 2H), 7.37 (d, 1H), 7.52-7.59 (m, 1H), 8.72 (d, 1H), 12.16 (br. s, 1H).

Example 15

3-[1-(2,6-Difluorobenzyl)-5-fluoro-6-methyl-1H-pyrazolo[3,4-b]pyridin-3-yl]-7,7-dimethyl-5,7-dihydro-6H-pyrrolo[2,3-e][1,2,4]triazin-6-one

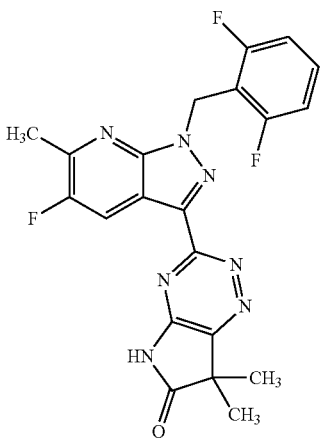 [SMILES: Cc1nc2c(cc1F)c(-c1nnc3c(n1)NC(=O)C3(C)C)nn2Cc1c(F)cccc1F]

50 mg (0.16 mmol) of 3-(5-fluoro-6-methyl-1H-pyrazolo[3,4-b]pyridin-3-yl)-7,7-dimethyl-5,7-dihydro-6H-pyrrolo[2,3-e][1,2,4]triazin-6-one from Example 24A were initially charged in 0.5 ml of DMF, 156 mg (0.48 mmol) of caesium carbonate and 25.5 mg (0.12 mmol) of 2,6-difluorobenzyl bromide were added and the mixture was stirred at room temperature for 1 h. Another 6.6 mg (0.032 mmol) of 2,6-difluorobenzyl bromide were added and the mixture was stirred at room temperature for 0.5 h. The reaction mixture was diluted with ethyl acetate and washed twice with water. The organic phase was dried over sodium sulphate, filtered and concentrated. The crude product was purified by thick-layer chromatography (mobile phase: dichloromethane/methanol=40/1). This gave 10.4 mg of the target compound (15% of theory).

LC-MS (Method 1): $R_t$=1.10 min

MS (EIpos): m/z=440 [M+H]$^+$.

$^1$H NMR (500 MHz, DMSO-d$_6$): δ [ppm]=1.44 (s, 6H), 2.67 (d, 3H), 5.82 (s, 2H), 7.12-7.19 (m, 2H), 7.44-7.52 (m, 1H), 8.41 (d, 1H), 12.14 (br. s, 1H).

Example 16

3-[1-(2,6-Difluorobenzyl)-6-methyl-1H-pyrazolo[3,4-b]pyridin-3-yl]-7,7-dimethyl-5,7-dihydro-6H-pyrrolo[2,3-e][1,2,4]triazin-6-one

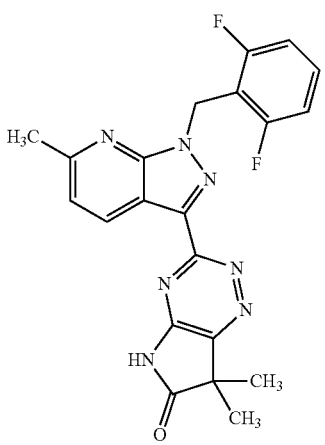 [SMILES: Cc1ccc2c(-c3nnc4c(n3)NC(=O)C4(C)C)nn(Cc3c(F)cccc3F)c2n1]

Example 17

3-[5-Fluoro-1-(3-fluoro-4-methylbenzyl)-6-methyl-1H-pyrazolo[3,4-b]pyridin-3-yl]-7,7-dimethyl-5,7-dihydro-6H-pyrrolo[2,3-e][1,2,4]triazin-6-one

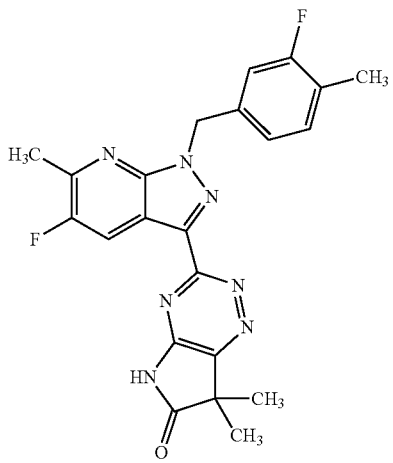

100 mg (0.34 mmol; purity 90%) of 7,7-dimethyl-3-(6-methyl-1H-pyrazolo[3,4-b]pyridin-3-yl)-5,7-dihydro-6H-pyrrolo[2,3-e][1,2,4]triazin-6-one from Example 32A were initially charged in 3.2 ml of DMF and heated to 80° C. 441 mg (1.36 mmol) of caesium carbonate were added to the mixture. 60 mg (0.29 mmol) of 2-(bromomethyl)-1,3-difluorobenzene, dissolved in 0.32 ml of DMF, were then added in 10 portions over a period of 10 min to the reaction mixture at 80° C., with about 1 min of stirring at 80° C. between the individual additions. The mixture was then stirred at 80° C. for 10 min. The reaction mixture was cooled, and water and 0.5 ml of formic acid were added. The resulting precipitate was filtered off and washed with acetonitrile and the filtrate was purified by preparative HPLC (RP-C18, mobile phase: acetonitrile/water gradient with addition of 0.05% formic acid). This gave 43 mg of the target compound (29% of theory).

LC-MS (Method 1): $R_t$=1.00 min

MS (EIpos): m/z=422 [M+H]$^+$.

$^1$H NMR (500 MHz, DMSO-d$_6$): δ [ppm]=1.43 (s, 6H), 2.69 (s, 3H), 5.81 (s, 2H), 7.10-7.18 (m, 2H), 7.34 (d, 1H), 7.43-7.51 (m, 1H), 8.69 (d, 1H), 12.12 (br. s, 1H).

80 mg (0.255 mmol) of 3-(5-fluoro-6-methyl-1H-pyrazolo[3,4-b]pyridin-3-yl)-7,7-dimethyl-5,7-dihydro-6H-pyrrolo[2,3-e][1,2,4]triazin-6-one from Example 24A were initially charged in 2.7 ml of DMF and heated to 80° C. 333 mg (1.02 mmol) of caesium carbonate were added to the mixture. 38.9 mg (0.19 mmol) of 4-(bromomethyl)-2-fluoro-1-methylbenzene, dissolved in 0.27 ml of DMF, were then added in 10 portions over a period of 10 min to the reaction mixture at 80° C., with about 1 min of stirring at 80° C. between the individual additions. The mixture was then stirred at 80° C. for 10 min. The reaction mixture was diluted with ethyl acetate and washed twice with water. The organic phase was dried over sodium sulphate, filtered and concentrated. The crude product was purified by thick-layer chromatography (mobile phase: dichloromethane/methanol=40/1). This gave 27 mg of the target compound (22% of theory, purity 92%).

LC-MS (Method 1): $R_t$=1.17 min

MS (EIpos): m/z=436 [M+H]$^+$.

$^1$H NMR (500 MHz, DMSO-d$_6$): δ [ppm]=1.45 (s, 6H), 2.16-2.20 (m, 3H), 2.65 (d, 3H), 5.76 (s, 2H), 6.99-7.03 (m, 1H), 7.04-7.09 (m, 1H), 7.23 (t, 1H), 8.44 (d, 1H), 12.14 (br. s, 1H).

Example 18

3-[1-(3-Fluoro-4-methylbenzyl)-6-methyl-1H-pyrazolo[3,4-b]pyridin-3-yl]-7,7-dimethyl-5,7-dihydro-6H-pyrrolo[2,3-e][1,2,4]triazin-6-one

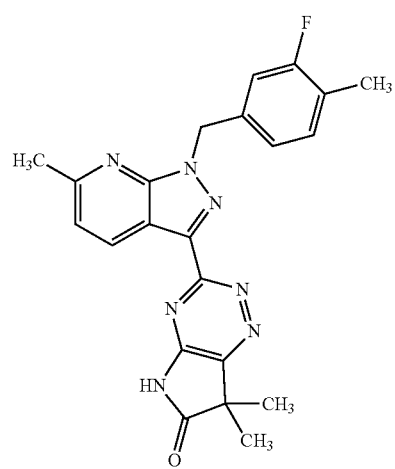

40 mg (0.135 mmol) of 7,7-dimethyl-3-(6-methyl-1H-pyrazolo[3,4-b]pyridin-3-yl)-5,7-dihydro-6H-pyrrolo[2,3-e][1,2,4]triazin-6-one from Example 32A were initially charged in 1.3 ml of DMF and heated to 80° C. 221 mg (0.677 mmol) of caesium carbonate were added to the mixture. 20.6 mg (0.102 mmol) of 4-(bromomethyl)-2-fluoro-1-methylbenzene, dissolved in 0.13 ml of DMF, were then added in 10 portions over a period of 10 min to the reaction mixture at 80° C., with about 1 min of stirring at 80° C. between the individual additions. The mixture was then stirred at 80° C. for 10 min. The reaction mixture was cooled, water and 0.3 ml of formic acid were added and the product was purified by preparative HPLC (RP-C18, mobile phase: acetonitrile/water gradient with addition of 0.05% formic acid). This gave 18.5 mg of the target compound (33% of theory).

LC-MS (Method 1): $R_t$=1.09 min

MS (EIpos): m/z=418 [M+H]$^+$.

$^1$H NMR (500 MHz, DMSO-d$_6$): δ [ppm]=1.45 (s, 6H), 2.16-2.19 (m, 3H), 2.67 (s, 3H), 5.75 (s, 2H), 6.98-7.02 (m, 1H), 7.03-7.08 (m, 1H), 7.21-7.25 (m, 1H), 7.35 (d, 1H), 8.71 (d, 1H), 12.14 (br. s, 1H).

Example 19

3-[1-(2,3-Difluoro-4-methylbenzyl)-5-fluoro-6-methyl-1H-pyrazolo[3,4-b]pyridin-3-yl]-7,7-dimethyl-5,7-dihydro-6H-pyrrolo[2,3-e][1,2,4]triazin-6-one

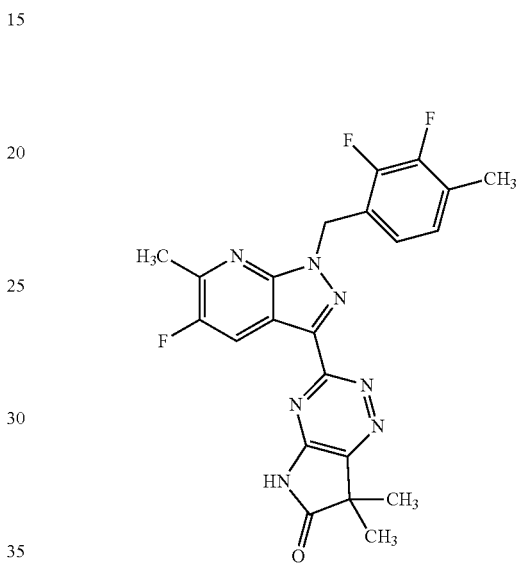

100 mg (0.319 mmol) of 3-(5-fluoro-6-methyl-1H-pyrazolo[3,4-b]pyridin-3-yl)-7,7-dimethyl-5,7-dihydro-6H-pyrrolo[2,3-e][1,2,4]triazin-6-one from Example 24A were initially charged in 3.4 ml of DMF and heated to 80° C. 416 mg (1.28 mmol) of caesium carbonate were added to the mixture. 53 mg (0.24 mmol) of 1-(bromomethyl)-2,3-difluoro-4-methylbenzene, dissolved in 0.34 ml of DMF, were then added in 10 portions over a period of 10 min to the reaction mixture at 80° C., with about 1 min of stirring at 80° C. between the individual additions. The mixture was then stirred at 80° C. for 10 min. The reaction mixture was diluted with ethyl acetate and washed twice with water. The organic phase was dried over sodium sulphate, filtered and concentrated. The crude product was purified by thick-layer chromatography (mobile phase: dichloromethane/methanol=40/1). This gave 22 mg of the target compound (14% of theory).

LC-MS (Method 1): $R_t$=1.20 min

MS (EIpos): m/z=454 [M+H]$^+$.

$^1$H NMR (500 MHz, DMSO-d$_6$): δ [ppm]=1.45 (s, 6H), 2.23-2.26 (m, 3H), 2.65 (d, 3H), 5.83 (s, 2H), 6.95-7.01 (m, 1H), 7.03-7.09 (m, 1H), 8.44 (d, 1H), 12.14 (br. s, 1H).

Example 20

3-[1-(2,3-Difluoro-4-methylbenzyl)-6-methyl-1H-pyrazolo[3,4-b]pyridin-3-yl]-7,7-dimethyl-5,7-dihydro-6H-pyrrolo[2,3-e][1,2,4]triazin-6-one

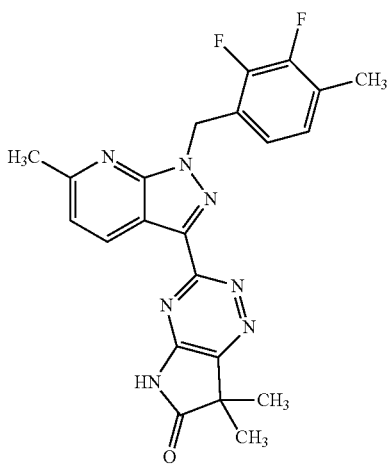

40 mg (0.135 mmol) of 7,7-dimethyl-3-(6-methyl-1H-pyrazolo[3,4-b]pyridin-3-yl)-5,7-dihydro-6H-pyrrolo[2,3-e][1,2,4]triazin-6-one from Example 32A were initially charged in 1.3 ml of DMF and heated to 80° C. 177 mg (0.542 mmol) of caesium carbonate were added to the mixture. 25.5 mg (0.115 mmol) of 1-(bromomethyl)-2,3-difluoro-4-methylbenzene, dissolved in 0.13 ml of DMF, were then added in 10 portions over a period of 10 min to the reaction mixture at 80° C., with about 1 min of stirring at 80° C. between the individual additions. The mixture was then stirred at 80° C. for 10 min. The reaction mixture was cooled, and water and 0.2 ml of formic acid were added. The resulting precipitate was filtered off with suction and washed with acetonitrile. The solid was dissolved in TFA/DMF and then purified by preparative HPLC (RP-C18, mobile phase: acetonitrile/water gradient with addition of 0.05% formic acid). This gave 16.7 mg of the target compound (28% of theory).

LC-MS (Method 1): $R_t$=1.08 min

MS (EIpos): m/z=436 [M+H]$^+$.

$^1$H NMR (500 MHz, DMSO-d$_6$): δ [ppm]=1.45 (s, 6H), 2.23-2.26 (m, 3H), 2.68 (s, 3H), 5.82 (s, 2H), 6.91-6.97 (m, 1H), 7.02-7.08 (m, 1H), 7.35 (d, 1H), 8.71 (d, 1H), 12.14 (br. s, 1H).

Example 21

3'-[5-Fluoro-1-(2-fluoro-4-methylbenzyl)-6-methyl-1H-pyrazolo[3,4-b]pyridin-3-yl]spiro[cyclopropane-1,7'-pyrrolo[2,3-e][1,2,4]triazin]-6'(5'H)-one

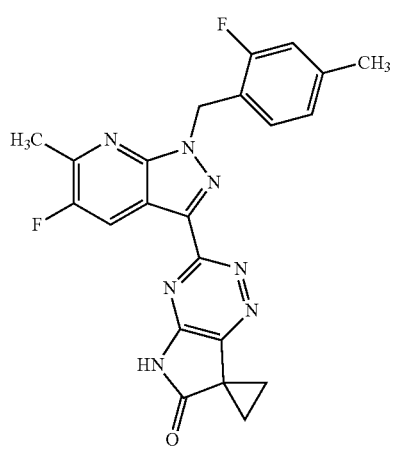

3'-(5-Fluoro-6-methyl-1H-pyrazolo[3,4-b]pyridin-3-yl)spiro[cyclopropane-1,7'-pyrrolo[2,3-e][1,2,4]triazin]-6'(5'H)-one (1 equivalent) from Example 40A is initially charged in DMF (concentration about 0.1 molar) and heated to 80° C. Caesium carbonate (4 equivalents) is added, and the mixture is stirred for 10 min 1-(Bromomethyl)-2-fluoro-4-methylbenzene (0.75 equivalent), dissolved in DMF (concentration about 0.7 molar), is then added in 10 portions over a period of 10 min to the reaction mixture at 80° C., with about 1 min of stirring at 80° C. between the individual additions. The mixture is then stirred at 80° C. for 10 min. The mixture is then diluted with ethyl acetate and washed twice with water. The organic phase is dried over sodium sulphate, filtered and concentrated. The crude product is dissolved in dichloromethane/methanol/1 N solution of ammonia in methanol (2/2/1) and purified by thick-layer chromatography (mobile phase: dichloromethane/methanol) or alternatively by preparative HPLC (RP-C18, mobile phase: acetonitrile/water gradient with addition of 0.1% TFA).

Example 22

3'-[1-(2-Fluoro-4-methylbenzyl)-6-methyl-1H-pyrazolo[3,4-b]pyridin-3-yl]spiro[cyclopropane-1,7'-pyrrolo[2,3-e][1,2,4]triazin]-6'(5'H)-one

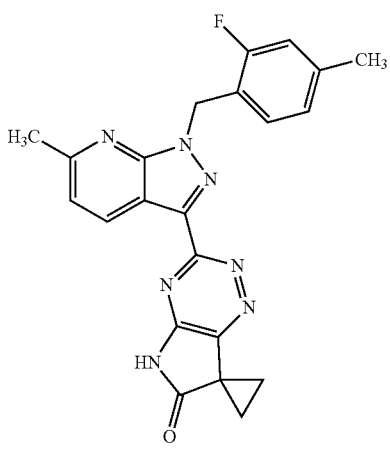

14.2 mg (0.044 mmol, purity 90%) of 3'46-methyl-1H-pyrazolo[3,4-b]pyridin-3-yl)spiro[cyclopropane-1,7'-pyrrolo[2,3-e][1,2,4]triazin]-6'(5'H)-one from Example 44A were initially charged in 500 µl of DMF, and 142 mg (0.436 mmol) of caesium carbonate were added. The mixture was heated to 80° C. and stirred for 10 min 7.1 mg (0.034 mmol) of 1-(bromomethyl)-2-fluoro-4-methylbenzene, dissolved in 50 µl of DMF, were then added in 10 portions over a period of 10 min to the reaction mixture at 80° C., with about 1 min of stirring at 80° C. between the individual additions. The mixture was then stirred at 80° C. for 10 min. The mixture was then cooled, and 0.1 ml of water and 0.9 ml of formic acid were added. The mixture was purified by preparative HPLC (RP-C18, mobile phase: acetonitrile/water gradient with addition of 0.1% formic acid). This gave 1.6 mg of the target compound (9% of theory).

LC-MS (Method 1): $R_t$=1.05 min

MS (EIpos): m/z=416 [M+H]$^+$.

$^1$H NMR (500 MHz, DMSO-d$_6$): δ [ppm]=1.80-1.86 (m, 2H), 1.93-2.00 (m, 2H), 2.28 (s, 3H), 2.67 (s, 3H), 5.76 (s, 2H), 6.96 (d, 1H), 7.06 (d, 1H), 7.12 (t, 1H), 7.33 (d, 1H), 8.68 (d, 1H), 12.32 (br. s, 1H).

Example 23

3'-[1-(2,3-Difluorobenzyl)-5-fluoro-6-methyl-1H-pyrazolo[3,4-b]pyridin-3-yl]spiro[cyclopropane-1,7'-pyrrolo[2,3-e][1,2,4]triazin]-6'(5'H)-one

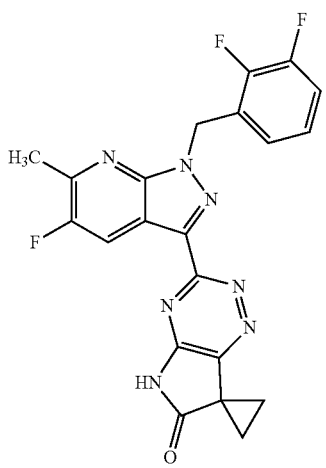 [SMILES: Cc1nc2c(cc1F)c(-c1nnc3c(n1)NC(=O)C31CC1)nn2Cc1cccc(F)c1F]

3'-(5-Fluoro-6-methyl-1H-pyrazolo[3,4-b]pyridin-3-yl)spiro[cyclopropane-1,7'-pyrrolo[2,3-e][1,2,4]triazin]-6'(5'H)-one (1 equivalent) from Example 40A is initially charged in DMF (concentration about 0.1 molar) and heated to 80° C. Caesium carbonate (4 equivalents) is added, and the mixture is then stirred for 10 min 1-(Bromomethyl)-2,3-difluorobenzene (0.75 equivalent), dissolved in DMF (concentration about 0.7 molar), is then added in 10 portions over a period of 10 min to the reaction mixture at 80° C., with about 1 min of stirring at 80° C. between the individual additions. The mixture is then stirred at 80° C. for 10 min. The mixture is then diluted with ethyl acetate and washed twice with water. The organic phase is dried over sodium sulphate, filtered and concentrated. The crude product is dissolved in dichloromethane/methanol/1 N solution of ammonia in methanol (2/2/1) and purified by thick-layer chromatography (mobile phase: dichloromethane/methanol) or alternatively by preparative HPLC (RP-C18, mobile phase: acetonitrile/water gradient with addition of 0.1% TFA).

Example 24

3'-[1-(2,3-Difluorobenzyl)-6-methyl-1H-pyrazolo[3,4-b]pyridin-3-yl]spiro[cyclopropane-1,7'-pyrrolo[2,3-e][1,2,4]triazin]-6'(5'H)-one

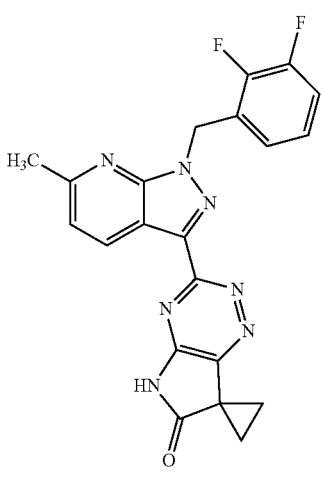 [SMILES: Cc1ccc2c(-c3nnc4c(n3)NC(=O)C43CC3)nn(Cc3cccc(F)c3F)c2n1]

10.0 mg (0.031 mmol, purity 90%) of 3'-(6-methyl-1H-pyrazolo[3,4-b]pyridin-3-yl)spiro[cyclopropane-1,7'-pyrrolo[2,3-e][1,2,4]triazin]-6'(5'H)-one from Example 44A were initially charged in 352 μl of DMF, and 100 mg (0.307 mmol) of caesium carbonate were added. The mixture was heated to 80° C. and stirred for 10 min 5.1 mg (0.024 mmol) of 1-(bromomethyl)-2,3-difluorobenzene, dissolved in 35 μl of DMF, were then added in 10 portions over a period of 10 min to the reaction mixture at 80° C., with about 1 min of stirring at 80° C. between the individual additions. The mixture was then stirred at 80° C. for 10 min. The mixture was then cooled, and 0.1 ml of water and 0.9 ml of formic acid were added. The mixture was purified by preparative HPLC (RP-C18, mobile phase: acetonitrile/water gradient with addition of 0.1% formic acid). This gave 2.6 mg of the target compound (20% of theory).

LC-MS (Method 1): $R_t$=1.00 min

MS (EIpos): m/z=420 [M+H]$^+$.

$^1$H NMR (500 MHz, DMSO-d$_6$): δ [ppm]=1.82-1.87 (m, 2H), 1.96-2.01 (m, 2H), 2.69 (s, 3H), 5.88 (s, 2H), 7.04-7.09 (m, 1H), 7.16-7.22 (m, 1H), 7.36 (d, 1H), 7.37-7.44 (m, 1H), 8.71 (d, 1H).

Example 25

3'-[1-(2,3-Difluoro-4-methylbenzyl)-5-fluoro-6-methyl-1H-pyrazolo[3,4-b]pyridin-3-yl]spiro[cyclopropane-1,7'-pyrrolo[2,3-e][1,2,4]triazin]-6'(5'H)-one

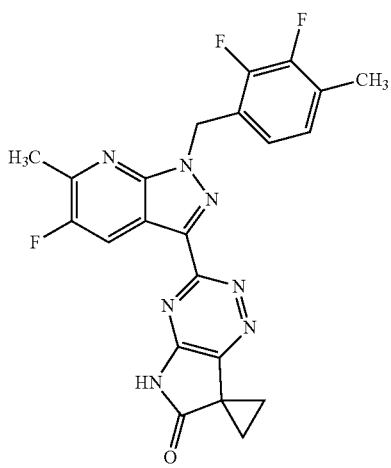

3'-(5-Fluoro-6-methyl-1H-pyrazolo[3,4-b]pyridin-3-yl)spiro[cyclopropane-1,7'-pyrrolo[2,3-e][1,2,4]triazin]-6'(5'H)-one (1 equivalent) from Example 40A is initially charged in DMF (concentration about 0.1 molar) and heated to 80° C. Caesium carbonate (4 equivalents) is added, and the mixture is stirred for 10 min 1-(Bromomethyl)-2,3-difluoro-4-methylbenzene (0.75 equivalent), dissolved in DMF (concentration about 0.7 molar), is then added in 10 portions over a period of 10 min to the reaction mixture at 80° C., with about 1 min of stirring at 80° C. between the individual additions. The mixture is then stirred at 80° C. for 10 min. The mixture is then diluted with ethyl acetate and washed twice with water. The organic phase is dried over sodium sulphate, filtered and concentrated. The crude product is dissolved in dichloromethane/methanol/1 N solution of ammonia in methanol (2/2/1) and purified by thick-layer chromatography (mobile phase: dichloromethane/methanol) or alternatively by preparative HPLC (RP-C18, mobile phase: acetonitrile/water gradient with addition of 0.1% TFA).

Example 26

3'-[1-(2,3-Difluoro-4-methylbenzyl)-6-methyl-1H-pyrazolo[3,4-b]pyridin-3-yl]spiro[cyclopropane-1,7'-pyrrolo[2,3-e][1,2,4]triazin]-6'(5'H)-one

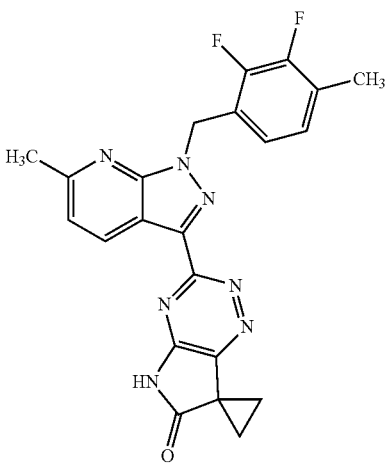

10.0 mg (0.031 mmol, purity 90%) of 3'-(6-methyl-1H-pyrazolo[3,4-b]pyridin-3-yl)spiro[cyclopropane-1,7'-pyrrolo[2,3-e][1,2,4]triazin]-6'(5'H)-one from Example 44A were initially charged in 352 µl of DMF, and 100 mg (0.307 mmol) of caesium carbonate were added. The mixture was heated to 80° C. and stirred for 10 min 5.4 mg (0.024 mmol) of 1-(bromomethyl)-2,3-difluoro-4-methylbenzene, dissolved in 35 µl of DMF, were then added in 10 portions over a period of 10 min to the reaction mixture at 80° C., with about 1 min of stirring at 80° C. between the individual additions. The mixture was then stirred at 80° C. for 10 min. The mixture was then cooled, and 0.1 ml of water and 0.9 ml of formic acid were added. The mixture was purified by preparative HPLC (RP-C18, mobile phase: acetonitrile/water gradient with addition of 0.1% formic acid). This gave 1.4 mg of the target compound (11% of theory).

LC-MS (Method 1): $R_t$=1.07 min

MS (EIpos): m/z=434 [M+H]$^+$.

$^1$H NMR (500 MHz, DMSO-d$_6$): δ [ppm]=1.81-1.85 (m, 2H), 1.95-1.98 (m, 2H), 2.25 (d, 3H), 2.67 (s, 3H), 5.81 (s, 2H), 6.94-6.99 (m, 1H), 7.03-7.08 (m, 1H), 7.34 (d, 1H), 8.69 (d, 1H), 12.32 (br. s, 1H).

B. ASSESSMENT OF PHARMACOLOGICAL EFFICACY

The pharmacological effect of the compounds according to the invention can be shown in the following assays:

B-1. Vasorelaxant Effect In Vitro

The determination of the relaxant activity of the compounds according to the invention on isolated vessels was carried out as described in J P Stasch et al., Br J Pharmacol. 2002; 135, 333-343. Rabbits are stunned by a blow to the neck and exsanguinated. The aorta is removed, freed from adhering tissue and divided into rings of a width of 1.5 mm. The rings are placed individually under an initial tension in 5 ml organ baths with Krebs-Henseleit solution which is at 37° C., is gassed with carbogen and has the following composition (in each case mM): sodium chloride: 119; potassium chloride: 4.8; calcium chloride dihydrate: 1; magnesium sulphate heptahydrate: 1.4; potassium dihydrogenphosphate: 1.2; sodium bicarbonate: 25; glucose: 10. The contractile force is determined with Statham UC2 cells, amplified and digitalized using A/D transducers (DAS-1802 HC, Keithley Instruments Munich), and recorded in parallel on linear recorders.

To produce a contraction, phenylephrine is added to the bath cumulatively in increasing concentration. After several control cycles, the substance to be investigated is added in each further run in increasing dosage in each case, and the height of the contraction achieved is compared with the height of the contraction reached in the last preceding run. This is used to calculate the concentration needed to reduce the magnitude of the control value by 50% (IC$_{50}$ value). The standard administration volume is 5 µl; the DMSO content in the bath solution corresponds to 0.1%.

B-2. Effect on a Recombinant Guanylate Cyclase Reporter Cell Line

The cellular activity of the compounds according to the invention is determined using a recombinant guanylate cyclase reporter cell line, as described in F. Wunder et al., Anal. Biochem. 339, 104-112 (2005).

Representative values (MEC=minimum effective concentration) for the compounds according to the invention are shown in the table below (Table 1; in some cases as means of individual determinations):

TABLE 1

| Example No. | MEC [nM] |
|---|---|
| 1 | 30 |
| 2 | 30 |
| 5 | 100 |
| 6 | 200 |
| 7 | 100 |
| 8 | 300 |
| 9 | 300 |
| 10 | 300 |
| 11 | 30 |
| 12 | 300 |
| 13 | 100 |
| 14 | 300 |
| 15 | 65 |
| 16 | 300 |
| 17 | 300 |
| 18 | 1000 |
| 19 | 300 |
| 20 | 300 |
| 24 | 300 |
| 26 | 300 |

B-3. Inhibition of Human Phosphodiesterase 5 (PDE 5)

PDE 5 preparations are obtained from human platelets by disruption (Microfluidizer®, 800 bar, 3 passes), followed by centrifugation (75000 g, 60 min, 4° C.) and ion exchange chromatography of the supernatant on a Mono Q 10/10 column (linear sodium chloride gradient, elution with a 0.2-0.3M solution of sodium chloride in buffer (20 mM Hepes pH 7.2, 2 mM magnesium chloride). Fractions having PDE 5 activity are combined (PDE 5 preparation) and stored at –80° C.

To determine their in vitro action on human PDE 5, the test substances are dissolved in 100% DMSO and serially diluted. Typically, dilution series (1:3) from 200 µM to 0.091 µM are prepared (resulting final concentrations in the test: 4 µM to 0.0018 µM). In each case 2 µl of the diluted substance solutions are placed into the wells of microtitre plates (Isoplate-96/200W; Perkin Elmer). Subsequently, 50 µl of a dilution of the above-described PDE 5 preparation are added. The dilution of the PDE 5 preparation is chosen such that during the later incubation less than 70% of the substrate are converted (typical dilution: 1:100; dilution buffer: 50 mM tris/hydrochloric acid pH 7.5, 8.3 mM magnesium chloride, 1.7 mM EDTA, 0.2% BSA). The substrate, [8-$^3$H] cyclic guanosine-3',5'-monophosphate (1 µCi/µl; Perkin Elmer) is diluted 1:2000 with assay buffer (50 mM tris/hydrochloric acid pH 7.5, 8.3 mM magnesium chloride, 1.7 mM EDTA) to a concentration of 0.0005 µCi/µl. By addition of 50 µl (0.025 µCi) of the diluted substrate, the enzyme reaction is finally started. The test mixtures are incubated at room temperature for 60 min and the reaction is stopped by adding 25 µl of a suspension of 18 mg/ml yttrium scintillation proximity beads in water (phosphodiesterase beads for SPA assays, RPNQ 0150, Perkin Elmer). The microtitre plates are sealed with a film and left to stand at room temperature for 60 min. Subsequently, the plates are analysed for 30 s per well in a Microbeta scintillation counter (Perkin Elmer). $IC_{50}$ values are determined using the graphic plot of the substance concentration against percentage PDE 5 inhibition.

Representative $IC_{50}$ values for the compounds according to the invention are shown in the table below (Table 2; in some cases as means of individual determinations):

TABLE 2

| Example No. | $IC_{50}$ [nM] |
| --- | --- |
| 1 | 5 |
| 2 | 5 |
| 5 | 1.5 |
| 6 | 2 |
| 7 | 21 |
| 8 | 34 |
| 9 | 6 |
| 10 | 4.5 |
| 11 | 27 |
| 12 | 21 |
| 13 | 42 |
| 14 | 63 |
| 15 | 67 |
| 16 | 24 |
| 17 | 8 |
| 18 | 10 |
| 19 | 0.25 |
| 20 | 0.65 |
| 22 | 16 |
| 24 | 21 |
| 26 | 4 |

B-4. Radiotelemetric Measurement of Blood Pressure on Conscious Spontaneously Hypertensive Rats A commercially available telemetry system from DATA SCIENCES INTERNATIONAL DSI, USA, is employed for the blood pressure measurement on conscious rats described below.

The system consists of 3 main components:
implantable transmitters (Physiotel® telemetry transmitter)
receivers (Physiotel® receiver) which are linked via a multiplexer (DSI Data Exchange Matrix) to a
data acquisition computer.

The telemetry system makes it possible to continuously record blood pressure, heart rate and body motion of conscious animals in their usual habitat.

Animal Material

The investigations are carried out on adult female spontaneously hypertensive rats (SHR Okamoto) with a body weight of >200 g. SHR/NCrl from the Okamoto Kyoto School of Medicine, 1963 were a cross of male Wistar Kyoto rats with highly elevated blood pressure and female rats having a slightly elevated blood pressure and at F13 handed over to the U.S. National Institutes of Health.

After transmitter implantation, the experimental animals are housed singly in type 3 Makrolon cages. They have free access to standard feed and water.

The day/night rhythm in the experimental laboratory is changed by the room lighting at 6:00 am and at 7:00 pm.

Transmitter Implantation

The telemetry transmitters TA11 PA-C40 used are surgically implanted under aseptic conditions in the experimental animals at least 14 days before the first experimental use. The animals instrumented in this way can be employed repeatedly after the wound has healed and the implant has settled.

For the implantation, the fasted animals are anaesthetized with pentobarbital (Nembutal, Sanofi: 50 mg/kg i.p.) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (VetBonD™, 3M). The transmitter housing is fixed intraperitoneally to the abdominal wall muscle, and layered closure of the wound is performed.

An antibiotic (Tardomyocel COMP, Bayer, 1 ml/kg s.c.) is administered postoperatively for prophylaxis of infection.

Substances and Solutions

Unless stated otherwise, the substances to be studied are administered orally by gavage to a group of animals in each case (n=6). In accordance with an administration volume of 5 ml/kg of body weight, the test substances are dissolved in suitable solvent mixtures or suspended in 0.5% tylose.

A solvent-treated group of animals is employed as control.

Test Procedure

The telemetry measuring unit present is configured for 24 animals Each experiment is recorded under an experiment number (Vyear month day).

Each of the instrumented rats living in the system is assigned a separate receiving antenna (1010 Receiver, DSI).

The implanted transmitters can be activated externally by means of an incorporated magnetic switch. They are switched to transmission in the run-up to the experiment. The signals emitted can be detected online by a data acquisition system (Dataquest™ A.R.T. for WINDOWS, DSI) and processed accordingly. The data are stored in each case in a file created for this purpose and bearing the experiment number.

In the standard procedure, the following are measured for 10-second periods in each case:
systolic blood pressure (SBP)
diastolic blood pressure (DBP)
mean arterial pressure (MAP)
heart rate (HR)
activity (ACT).

The acquisition of measurements is repeated under computer control at 5-minute intervals. The source data obtained as absolute value are corrected in the diagram with the currently measured barometric pressure (Ambient Pressure Reference Monitor; APR-1) and stored as individual data. Further technical details are given in the extensive documentation from the manufacturing company (DSI).

Unless indicated otherwise, the test substances are administered at 9.00 am on the day of the experiment. Following the administration, the parameters described above are measured over 24 hours.

Evaluation

After the end of the experiment, the acquired individual data are sorted using the analysis software (DATAQUEST™ A.R.T.™ ANALYSIS). The blank value is assumed to be the time 2 hours before administration, and so the selected data set encompasses the period from 7.00 am on the day of the experiment to 9.00 am the following day.

The data are smoothed over a presettable time by determination of the average (15-minute average) and transferred as a text file to a storage medium. The measured values presorted and compressed in this way are transferred into Excel templates and tabulated. For each day of the experiment, the data obtained are stored in a dedicated file bearing the number of the experiment. Results and test protocols are filed in paper form sorted by numbers.

Literature

Klaus Witte, Kai Hu, Johanna Swiatek, Claudia Müssig, Georg Ertl and Björn Lemmer: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured With Radio-Telemetry. Physiology & Behavior 55(4): 783-787, 1994

B-5. Determination of Organ-Protective Effects in a Long-Term Experiment on Rats The organ-protective effects of the compounds according to the invention are shown in a therapeutically relevant "low nitric oxide (NO)/high renin" hypertension model in rats. The study was carried out analogously to the recently published article (Sharkovska Y, et al. J Hypertension 2010; 28: 1666-1675). This involves treating renin-transgenic rats (TGR(mRen2)27) to which the NO synthase inhibitor L-NAME had been administered via drinking water simultaneously with the compound according to the invention or vehicle over several weeks. Haemodynamic and renal parameters are determined during the treatment period. At the end of the long-term study, organ protection (kidney, lung, heart, aorta) is shown by histopathological studies, biomarkers, expression analyses and cardiovascular plasma parameters.

B-6. Measurements of the Pulmonary Artery Pressure (PAP) in Conscious Dogs Under Hypoxia Conditions A telemetry system from DATA SCIENCES INTERNATIONAL DSI, USA, for example, is employed for the blood pressure measurement on conscious dogs described below. The system consists of implantable pressure transmitters, receiver and a data acquisition computer. The telemetry system makes it possible to continuously monitor blood pressures and heart rate of conscious animals. The telemetry transmitters used are surgically implanted under aseptic conditions in the experimental animals before the first experimental use. The animals instrumented in this way can be employed repeatedly after the wound has healed and the implant has settled. The tests are carried out using adult male beagles. Technical details can be found in the documentation from the manufacturing company (DSI).

Substances and Solutions

The substances to be tested are each administered to a group of dogs (n=3-6), orally via a gelatine capsule or intravenously in suitable solvent mixtures. A vehicle-treated group of animals is employed as control.

Test Procedure

For the measurements under hypoxia conditions, the animals are transferred to a chamber with a hypoxic atmosphere (oxygen content about 10%). This is established using commercially available hypoxia generators (from Hoehenbalance, Cologne, Germany) In a standard experiment, for example, one hour and five hours after substance administration the dogs are kept in the hypoxia chamber for 30 min. About 10 min before and after entering the hypoxia chamber, as well as during the stay in the hypoxia chamber, pressures and heart rate are measured by telemetry.

Evaluation

In healthy dogs, under hypoxia there is a rapid increase in PAP. By substance administration, this increase can be reduced. To quantify the PAP increase and the differences in heart rate and systemic blood pressure, the data before and during the hypoxia period, smoothed by determination of means, are compared. The courses of the measured parameters are presented graphically using the Prism software (GraphPad, USA).

B-7. Determination of Pharmacokinetic Parameters Following Intravenous and Oral Administration The pharmacokinetic parameters of the compounds according to the invention are determined in male CD-1 mice, male Wistar rats, female beagles and female cynomolgus monkeys. Intravenous administration in the case of mice and rats is effected by means of a species-specific plasma/DMSO formulation, and in the case of dogs and monkeys by means of a water/PEG400/ethanol formulation. In all species, oral administration of the dissolved substance is performed via gavage, based on a water/PEG400/ethanol formulation. The removal of blood from rats is simplified by inserting a silicone catheter into the right Vena jugularis externa prior to substance administration. The operation is effected at least one day prior to the experiment with isofluran anaesthesia and administration of an analgesic (atropine/rimadyl (3/1) 0.1 ml s.c.). The blood is taken (generally more than 10 time points) within a time window including terminal time points of at least 24 to a maximum of 72 hours after substance administration. The blood is removed into heparinized tubes. The blood plasma is then obtained by centrifugation; if required, it can be stored at $-20°$ C. until further processing.

An internal standard (which may also be a chemically unrelated substance) is added to the samples of the compounds according to the invention, calibration samples and qualifiers, and there follows protein precipitation by means of acetonitrile in excess. Addition of a buffer solution matched to the LC conditions, and subsequent vortexing, is followed by centrifugation at 1000 g. The supernatant is analysed by LC-MS(/MS) using C18 reversed-phase columns and variable mobile phase mixtures. The substances are quantified via the peak heights or areas from extracted ion chromatograms of specific selected ion monitoring experiments or high-resolution LC-MS experiments.

The plasma concentration/time plots determined are used to calculate the pharmacokinetic parameters such as AUC, $C_{max}$, F (bioavailability), $t_{1/2}$ (terminal half life), MRT (mean residence time) and CL (clearance), using a validated pharmacokinetic calculation program.

Since the substance quantification is performed in plasma, it is necessary to determine the blood/plasma distribution of the substance in order to be able to adjust the pharmacokinetic parameters correspondingly. For this purpose, a defined amount of substance is incubated in heparinized whole blood of the species in question in a rocking roller mixer for 20 min. Plasma is obtained by centrifugation at 1000 g. After measurement of the concentrations in plasma and blood (by LC-MS(/MS); see above), the $C_{blood}/C_{plasma}$ value is determined by quotient formation.

B-8. Metabolic Study

To determine the metabolic profile of the compounds according to the invention, they are incubated with recombinant human cytochrome P450 (CYP) enzymes, liver microsomes or primary fresh hepatocytes from various animal species (e.g. rats, dogs), and also of human origin, in order to obtain and to compare information about a very substantially complete hepatic phase I and phase II metabolism, and about the enzymes involved in the metabolism.

The compounds according to the invention were incubated with a concentration of about 0.1-10 µM. To this end, stock solutions of the compounds according to the invention having a concentration of 0.01-1 mM in acetonitrile were prepared, and then pipetted with 1:100 dilution into the incubation mixture. Liver microsomes and recombinant enzymes were incubated at 37° C. in 50 mM potassium phosphate buffer pH 7.4 with and without NADPH-generating system consisting of 1 mM $NADP^+$, 10 mM glucose-6-phosphate and 1 unit glucose-6-phosphate dehydrogenase. Primary hepatocytes were incubated in suspension in Williams E medium, likewise at 37° C. After an incubation time of 0-4 h, the incubation mixtures were stopped with acetonitrile (final concentration about 30%) and the protein was centrifuged off at about 15000×g. The samples thus stopped were either analysed directly or stored at −20° C. until analysis.

The analysis is carried out by high-performance liquid chromatography with ultraviolet and mass spectrometry detection (HPLC-UV-MS/MS). To this end, the supernatants of the incubation samples are chromatographed with suitable C18 reversed-phase columns and variable mobile phase mixtures of acetonitrile and 10 mM aqueous ammonium formate solution or 0.05% formic acid. The UV chromatograms in conjunction with mass spectrometry data serve for identification, structural elucidation and quantitative estimation of the metabolites, and for quantitative metabolic assessment of the compound according to the invention in the incubation mixtures.

C. WORKING EXAMPLES OF PHARMACEUTICAL COMPOSITIONS

The compounds according to the invention can be converted to pharmaceutical formulations as follows:
Tablet:
Composition:

100 mg of the compound according to the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg, diameter 8 mm, radius of curvature 12 mm.
Production:

The mixture of compound according to the invention, lactose and starch is granulated with a 5% solution (w/w) of the PVP in water. The granules are dried and mixed with the magnesium stearate for 5 minutes. This mixture is pressed with a conventional tableting press (for tablet dimensions see above). The guide value used for the pressing is a pressing force of 15 kN.
Suspension which can be Administered Orally:
Composition:

1000 mg of the compound according to the invention, 1000 mg of ethanol (96%), 400 mg of Rhodigel® (xanthan gum from FMC, Pennsylvania, USA) and 99 g of water.

A single dose of 100 mg of the compound according to the invention corresponds to 10 ml of oral suspension.

Production:

The Rhodigel is suspended in ethanol and the compound according to the invention is added to the suspension. The water is added while stirring. The mixture is stirred for about 6 h until swelling of the Rhodigel is complete.
Solution which can be Administered Orally:
Composition:

500 mg of the compound according to the invention, 2.5 g of polysorbate and 97 g of polyethylene glycol 400. A single dose of 100 mg of the compound according to the invention corresponds to 20 g of oral solution.
Production:

The compound according to the invention is suspended in the mixture of polyethylene glycol and polysorbate while stirring. The stirring operation is continued until dissolution of the compound according to the invention is complete.
i.v. Solution:

The compound according to the invention is dissolved in a concentration below the saturation solubility in a physiologically acceptable solvent (e.g. isotonic saline, glucose solution 5% and/or PEG 400 solution 30%). The solution is subjected to sterile filtration and dispensed into sterile and pyrogen-free injection vessels.

The invention claimed is:
1. A compound of the formula (I):

in which
$R^1$ represents hydrogen or fluorine,
$R^2$ represents hydrogen or fluorine,
$R^3$ represents hydrogen, chlorine or fluorine,
$R^4$ represents hydrogen, chlorine, fluorine or methyl, with the proviso that at least two of the radicals $R^1$, $R^2$, $R^3$ or $R^4$ are different from hydrogen,
$R^5$ represents hydrogen or fluorine,
$R^6$ represents methyl,
$R^7$ represents methyl,
or
$R^6$ and $R^7$ together with the carbon atom to which they are attached form a cyclopropyl ring,
and the N-oxides, salts, solvates, salts of the N-oxides and solvates of the N-oxides or salts thereof.
2. A compound having the systematic name 3-[1-(2,3-difluorobenzyl)-5-fluoro-6-methyl-1H-pyrazolo[3,4-b]pyridin-3-yl]-7,7-dimethyl-5,7-dihydro-6H-pyrrolo[2,3-e][1,2,4]triazin-6-one and the structural formula (I-A):

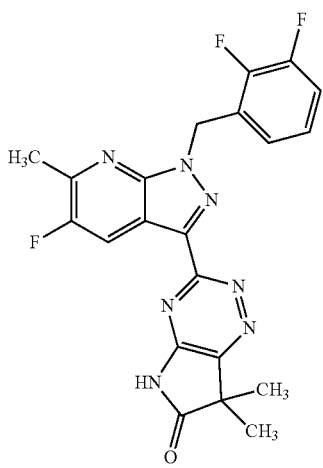

(I-A)

and the N-oxides, salts, solvates, salts of the N-oxides and solvates of the N-oxides or salts thereof.

3. A compound having the systematic name 3-[1-(2,3-difluorobenzyl)-6-methyl-1H-pyrazolo[3,4-b]pyridin-3-yl]-7,7-dimethyl-5,7-dihydro-6H-pyrrolo[2,3-e][1,2,4]triazin-6-one and the structural formula (I-B):

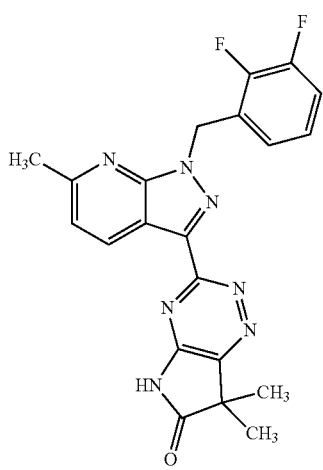

(I-B)

and the N-oxides, salts, solvates, salts of the N-oxides and solvates of the N-oxides or salts thereof.

4. A compound having the systematic name 3-[5-fluoro-1-(2-fluoro-4-methylbenzyl)-6-methyl-1H-pyrazolo[3,4-b]pyridin-3-yl]-7,7-dimethyl-5,7-dihydro-6H-pyrrolo[2,3-e][1,2,4]triazin-6-one and the structural formula (I-C):

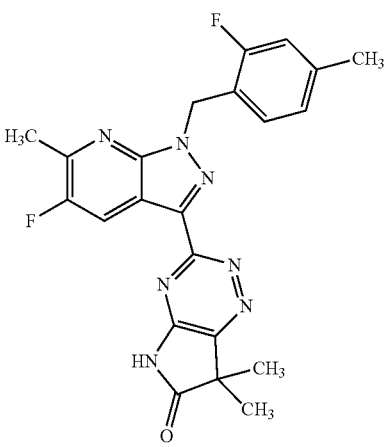

(I-C)

and the N-oxides, salts, solvates, salts of the N-oxides and solvates of the N-oxides or salts thereof.

5. A compound having the systematic name 3-[5-fluoro-6-methyl-1-(2,3,6-trifluorobenzyl)-1H-pyrazolo[3,4-b]pyridin-3-yl]-7,7-dimethyl-5,7-dihydro-6H-pyrrolo[2,3-e][1,2,4]triazin-6-one and the structural formula (I-I):

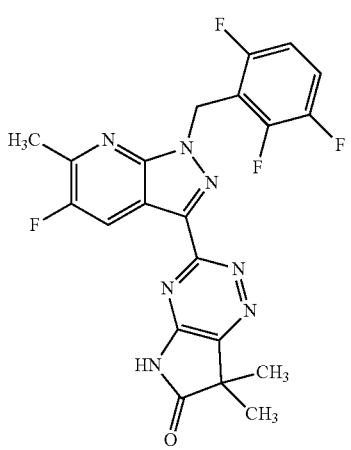

(I-I)

and the N-oxides, salts, solvates, salts of the N-oxides and solvates of the N-oxides or salts thereof.

6. A compound having the systematic name 3-[1-(2,3-difluoro-4-methylbenzyl)-5-fluoro-6-methyl-1H-pyrazolo[3,4-b]pyridin-3-yl]-7,7-dimethyl-5,7-dihydro-6H-pyrrolo[2,3-e][1,2,4]triazin-6-one and the structural formula (I-Q):

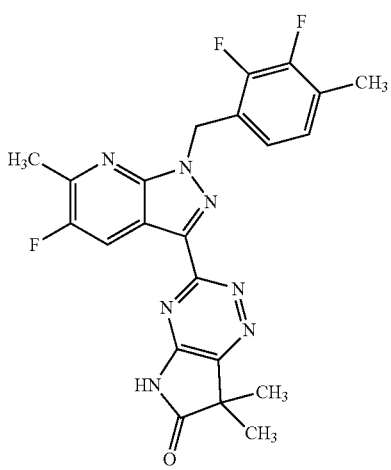

(I-Q)

and the N-oxides, salts, solvates, salts of the N-oxides and solvates of the N-oxides or salts thereof.

7. A medicament comprising the compound of claim 1 in combination with an inert, non-toxic, pharmaceutically suitable auxiliary.

8. A medicament comprising the compound of claim 1 in combination with a further active compound selected from the group consisting of organic nitrates, NO donors, cGMP-PDE inhibitors, agents having antithrombotic activity, agents lowering blood pressure, and agents altering lipid metabolism.

9. A method for treatment of heart failure, angina pectoris, hypertension, pulmonary hypertension, ischemias, arteriosclerosis, and erectile dysfunction in a human in need thereof, comprising administering an effective amount of compound of claim 1 to the human in need thereof.

10. A medicament comprising the compound of claim 2 in combination with an inert, non-toxic, pharmaceutically suitable auxiliary.

11. A medicament comprising the compound of claim 3 in combination with an inert, non-toxic, pharmaceutically suitable auxiliary.

12. A medicament comprising the compound of claim 4 in combination with an inert, non-toxic, pharmaceutically suitable auxiliary.

13. A medicament comprising the compound of claim 5 in combination with an inert, non-toxic, pharmaceutically suitable auxiliary.

14. A medicament comprising the compound of claim 6 in combination with an inert, non-toxic, pharmaceutically suitable auxiliary.

15. A medicament comprising the compound of claim 2 in combination with a further active compound selected from the group consisting of organic nitrates, NO donors, cGMP-PDE inhibitors, agents having antithrombotic activity, agents lowering blood pressure, and agents altering lipid metabolism.

16. A medicament comprising the compound of claim 3 in combination with a further active compound selected from the group consisting of organic nitrates, NO donors, cGMP-PDE inhibitors, agents having antithrombotic activity, agents lowering blood pressure, and agents altering lipid metabolism.

17. A medicament comprising the compound of claim 4 in combination with a further active compound selected from the group consisting of organic nitrates, NO donors, cGMP-PDE inhibitors, agents having antithrombotic activity, agents lowering blood pressure, and agents altering lipid metabolism.

18. A medicament comprising the compound of claim 5 in combination with a further active compound selected from the group consisting of organic nitrates, NO donors, cGMP-PDE inhibitors, agents having antithrombotic activity, agents lowering blood pressure, and agents altering lipid metabolism.

19. A medicament comprising the compound of claim 6 in combination with a further active compound selected from the group consisting of organic nitrates, NO donors, cGMP-PDE inhibitors, agents having antithrombotic activity, agents lowering blood pressure, and agents altering lipid metabolism.

20. A method for treatment of heart failure, angina pectoris, hypertension, pulmonary hypertension, ischemias, arteriosclerosis, and erectile dysfunction in a human in need thereof, comprising administering an effective amount of compound of claim 2 to the human in need thereof.

21. A method for treatment of heart failure, angina pectoris, hypertension, pulmonary hypertension, ischemias, arteriosclerosis, and erectile dysfunction in a human in need thereof, comprising administering an effective amount of compound of claim 3 to the human in need thereof.

22. A method for treatment of heart failure, angina pectoris, hypertension, pulmonary hypertension, ischemias, arteriosclerosis, and erectile dysfunction in a human in need thereof, comprising administering an effective amount of compound of claim 4 to the human in need thereof.

23. A method for treatment of heart failure, angina pectoris, hypertension, pulmonary hypertension, ischemias, arteriosclerosis, and erectile dysfunction in a human in need thereof, comprising administering an effective amount of compound of claim 5 to the human in need thereof.

24. A method for treatment of heart failure, angina pectoris, hypertension, pulmonary hypertension, ischemias, arteriosclerosis, and erectile dysfunction in a human in need thereof, comprising administering an effective amount of compound of claim 6 to the human in need thereof.

* * * * *